United States Patent
Wong et al.

(10) Patent No.: US 7,122,332 B2
(45) Date of Patent: Oct. 17, 2006

(54) MODULATORS OF LEUKOCYTE ACTIVATION, COMPOSITIONS AND METHODS OF USE

(75) Inventors: Brian Wong, Los Altos, CA (US); Chong Alan Fu, Union City, CA (US); Helena Mancebo, Fremont, CA (US); Xiulan X. Z. Zhou, Palo Alto, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 404 days.

(21) Appl. No.: 10/039,761

(22) Filed: Oct. 19, 2001

(65) Prior Publication Data

US 2003/0036107 A1    Feb. 20, 2003

Related U.S. Application Data

(60) Provisional application No. 60/280,698, filed on Mar. 29, 2001.

(51) Int. Cl.
| | |
|---|---|
| *G01N 33/53* | (2006.01) |
| *C12N 15/63* | (2006.01) |
| *C12N 15/00* | (2006.01) |
| *C12N 15/12* | (2006.01) |

(52) U.S. Cl. .................... 435/7.8; 435/320.1; 435/325; 435/69.1

(58) Field of Classification Search ................ 435/7.8, 435/320.1, 325, 69.1
See application file for complete search history.

(56) References Cited

U.S. PATENT DOCUMENTS 5,391,490 A    2/1995    Varshavsky et al.
5,494,818 A    2/1996    Baker et al.

FOREIGN PATENT DOCUMENTS

| WO | WO 00/79267 A2 | 12/2000 |
|---|---|---|
| WO | WO 0078934 | * 12/2000 |

OTHER PUBLICATIONS

Baek et al., "Molecular Cloning of a Novel Ubiquitin-specific Protease, UBP41, with Isopeptidase Activity in Chick Skeletal Muscle", *The Journal of Biological Chemistry* 272:41: 25560-25565 (1997).

Gong et al., "Differential Regulation of Sentrinized Proteins by a Novel Sentrin-specific Protease", *The Journal of Biological Chemistry* 275:5: 3355-3359 (2000).

Gong et al., "Identification of a Novel Isopeptidase with Dual Specificity for Ubiquitin- and NEDD8-conjugated Proteins", *The Journal of Biological Chemistry* 275:19: 14212-14216 (2000).

* cited by examiner

*Primary Examiner*—Joseph Murphy
(74) *Attorney, Agent, or Firm*—Townsend and Townsend and Crew LLP

(57) ABSTRACT

The present invention provides compositions and methods for modulating leukocyte activation. Nucleic acids encoding proteins and proteins so encoded which are capable of modulating leukocyte activation are provided. Compositions and methods for the treatment of disorders related to leukocyte dysfunction or dysregulation are also provided. Prophylactics and methods for the prevention of such disorders are also provided. Also provided are compositions and methods for diagnostic and prognostic determination of such disorders. Further provided are assays for the identification of bioactive agents capable of modulating leukocyte activation.

8 Claims, 25 Drawing Sheets

```
   1 CGGCAGCAAAGGAACGTGCGAACGCGTGACGCCGCCCGACTGGCTCGCGCTCTCCCGTGC
  61 CCCGGCGTCCTCCGCCCGCTCATGGCCCGGGCCGCCGCGGACGAGCGGCGCTGAGGCGGG
 121 CCGCGTGGAGACGTGAGGCGGCCGCCGTGGCCCTCACAGTCGGCGTTTCGCCGCCTGCCC
 181 GCGGTGCCCGCGCACGCCTGCCGCCATCGCCTTCGCGCCTGGCTGGCGGGGCGCTGTCC
 241 TCCCAGGCCGTCCGCGCCGCTCCCTGGAGCTCGGCGGAGCGCGGCAGCCAGGGCCGGCGG
 301 AGGCGCGAGGAGCCGGGCGCCACCGCCGCCGCCGCCGCCGCCGCCGCGGGGGCCATGACC
 361 GTGGAGCAGAACGTGCTGCAGCAGAGCGCGGCGCAGAAGCACCAGCAGACGTTTTTGAAT
 421 CAACTGAGAGAAATTACGGGGATTAATGACACCCAGATACTACAGCAAGCCTTGAAGGAT
 481 AGTAATGGAAACTTGGAATTAGCAGTGGCTTTCCTTACTGCGAAGAATGCTAAGACCCCT
 541 CAGCAGGAGGAGACAACTTACTACCAAACAGCACTTCCTGGCAATGATAGATACATCAGT
 601 GTGGGAAGCCAAGCAGATACAAATGTGATTGATCTCACTGGAGATGATAAAGATGATCTT
 661 CAGAGAACAATTGCCTTGAGTTTGGCCGAATCAAACAGGGCATTCAGGGAGACTGGAATA
 721 ACTGATGAGGAACAAGCCATTAGCAGAGTTCTTGAAGCCAGTATAGCAGAGAATAAAGCA
 781 TGTTTGAAGAGGACACCTACAGAAGTTTGGAGGGATTCTCGAAACCCTTATGATAGAAAA
 841 AGACAGGACAAAGCTCCCGTTGGGCTAAAGAATGTTGGCAATACTTGTTGGTTTAGTGCT
 901 GTTATTCAGTCATTATTTAATCTTTTGGAATTTAGAAGATTAGTTCTGAATTACAAGCCT
 961 CCATCAAATGCTCAAGATTTACCCCGAAACCAAAAGGAACATCGGAATTTGCCTTTTATG
1021 CGTGAGCTGAGGTATCTATTTGCACTTCTTGTTGGTACCAAAAGGAAGTATGTTGATCCA
1081 TCAAGAGCAGTTGAAATTCTTAAGGATGCTTTCAAATCAAATGACTCACAGCAGCAAGAT
1141 GTGAGTGAGTTTACACACAAATTATTAGATTGGTTAGAAGATGCCTTCCAAATGAAAGCT
1201 GAAGAGGAGACGGATGAAGAGAAGCCAAAGAACCCCATGGTAGAGTTGTTCTATGGCAGA
1261 TTCCTGGCTGTGGGAGTACTTGAAGGTAAAAAATTTGAAAACACTGAAATGTTTGGTCAG
1321 TACCCACTTCAGGTCAATGGGTTCAAAGATCTGCATGAGTGCCTAGAAGCTGCAATGATT
1381 GAAGGAGAAATTGAGTCTTTACATTCAGAGAATTCAGGAAAATCAGGCCAAGAGCATTGG
1441 TTTACTGGATTACCACCTGTGTTAACATTTGANTTGTCAAGATTTGAATTTAATCAGGCA
1501 TTGGGAAGACCAGAAAAAATTCACAACAAATTAGAATTTCCCCAAGTTTTATATTTGGAC
1561 AGATACATGCACAGAAACAGAGAAATAACAAGAATTAAGAGGGAAGAGATCAAGAGACTG
1621 AAAGATTACCTCACGGTATTACAACAAAGGCTAGAAAGATATTTAAGCTATGGTTCCGGT
1681 CCCAAACGATTCCCCTTGGTAGATGTTCTTCAGTATGCATTGGAATTTGCCTCAAGTAAA
1741 CCTGTTTGCACTTCTCCTGTTGACGATATTGACGCTAGTTCCCCACCTAGTGGTTCCATA
1801 CCATCACAGACATTACCAAGCACAACAGAACAACAGGGAGCCCTATCTTCAGAACTGCCA
1861 AGCACATCACCTTCATCAGTTGCTGCCATTTCATCGAGATCAGTAATACACAAACCATTT
1921 ACTCAGTCCCGGATACCTCCAGATTTGCCCATGCATCCGGCACCAAGGCACATAACGGAG
1981 GAAGAACTTTCTGTGCTGGAAAGTTGTTTACATCGCTGGAGGACAGAAATAGAAAATGAC
2041 ACCAGAGATTTGCAGGAAAGCATATCCAGAATCCATCGAACAATTGAATTAATGTACTCT
2101 GACAAATCTATGATACAAGTTCCTTATCGATTACATGCCGTTTTAGTTCACGAAGGCCAA
2161 GCTAATGCTGGGCACTACTGGGCATATATTTTTGATCATCGTGAAAGCAGATGGATGAAG
2221 TACAATGATATTGCTGTGACAAAATCATCATGGGAAGAGCTAGTGAGGGACTCTTTTGGT
2281 GGTTATAGAAATGCCAGTGCATACTGTTTAATGTACATAAATGATAAGGCACAGTTCCTA
2341 ATACAAGAGGAGTTTAATAAAGAAACTGGGCAGCCCCTTGTTGGTATAGAAACATTACCA
2401 CCGGATTTGAGAGATTTTGTTGAGGAAGACAACCAACGATTTGAAAAGAACTAGAAGAA
2461 TGGGATGCACAACTTGCCCAGAAAGCTTTGCAGGAAAGCTTTTAGCGTCTCAGAAATTG
2521 AGAGAGTCAGAGACTTCTGTGACAACAGCACAAGCAGCAGGAGACCCAGAATATCTAGAG
2581 CAGCCATCAAGAAGTGATTTCTCAAAGCACTTGAAAGAAGAAACTATTCAAATAATTACC
2641 AAGGCATCACATGAGCATGAAGATAAAAGTCCTGAAACAGTTTTGCAGTCGGCAATTAAG
2701 TTGGAATATGCAAGGTTGGTTAAGTTGGCCCAAGAAGACACCCCACCAGAAACCGATTAT
2761 CGTTTACATCATGTAGTGGTCTACTTTATCCAGAACCAGGCACCAAAGAAAATTATTGAG
2821 AAAACATTACTAGAACAATTTGGAGATAGAAATTTGAGTTTTGATGAAAGGTGTCACAAC
2881 ATAATGAAAGTTGCTCAAGCCAAACTGGAAATGATAAAACCTGAAGAAGTAAACTTGGAG
2941 GAATATGAGGAGTGGCATCAGGATTATAGGAAATTCAGGGAAACAACTATGTATCTCATA
```

*FIG._1A*

```
3001 ATTGGGCTAGAAAATTTTCAAAGAGAAAGTTATATAGATTCCTTGCTGTTCCTCATCTGT
3061 GCTTATCAGAATAACAAAGAACTCTTGTCTAAAGGCTTATACAGAGGACATGATGAAGAA
3121 TTGATATCACATTATAGAAGAGAATGTTTGCTAAAATTAAATGAGCAAGCCGCAGAACTC
3181 TTCGAATCTGGAGAGGATCGAGAAGTAAACAATGGTTTGATTATCATGAATGAGTTTATT
3241 GTCCCATTTTTGCCATTATTACTGGTGGATGAAATGGAAGAAAAGGATATACTAGCTGTA
3301 GAAGATATGAGAAATCGATGGTGTTCCTACCTTGGTCAAGAAATGGAACCACACCTCCAA
3361 GAAAAGCTGACAGATTTTTTGCCAAAACTGCTTGATTGTTCTATGGAGATTAAAAGTTTC
3421 CATGAGCCACCGAAGTTACCTTCATATTCCACGCATGAACTCTGTGAGCGATTTGCCCGA
3481 ATCATGTTGTCCCTCAGTCGAACTCCTGCTGATGGAAGATAAACTGCACACTTTCCCTGA
3541 ACACACTGTATAAACTCTTTTTAGTTCTTAACCCTTGCCTTCCTGTCACAGGGTTTGCTT
3601 GTTGCTGCTATAGTTTTTAACTTTTTTTTATTTTAATAACTGCAAAAGACAAAATGACTA
3661 TACAGACTTTAGTCAGACTGCAGACAATAAAGCTGAAAATCGCATGGCGCTCAGACATTT
3721 TAACCGGAACTGATGTATAATCACAAATCTAATTGATTTTATTATGGCAAAACTATGCTT
3781 TTGCCACCTTCCTGTTGCAGTATTACTTTGCTTTTATCTTTTCTTTCTCAACAGCTTTCC
3841 ATTCAGTCTGGATCCTTCCATGACTACAGCCATTTAAGTGTTCAGCACTGTGTACGATAC
3901 ATAATATTTGGTAGCTTGTAAATGAAATAAAGAATAAAGTTTTATTTATGGCTAC
```

FIG._1B

```
   1 MTVEQNVLQQSAAQKHQQTFLNQLREITGINDTQILQQALKDSNGNLELAVAFLTAKNAK
  61 TPQQEETTYYQTALPGNDRYISVGSQADTNVIDLTGDDKDDLQRTIALSLAESNRAFRET
 121 GITDEEQAISRVLEASIAENKACLKRTPTEVWRDSRNPYDRKRQDKAPVGLKNVGNTCWF
 181 SAVIQSLFNLLEFRRLVLNYKPPSNAQDLPRNQKEHRNLPFMRELRYLFALLVGTKRKYV
 241 DPSRAVEILKDAFKSNDSQQQDVSEFTHKLLDWLEDAFQMKAEEETDEEKPKNPMVELFY
 301 GRFLAVGVLEGKKFENTEMFGQYPLQVNGFKDLHECLEAAMIEGEIESLHSENSGKSGQE
 361 HWFTGLPPVLTFXLSRFEFNQALGRPEKIHNKLEFPQVLYLDRYMHRNREITRIKREEIK
 421 RLKDYLTVLQQRLERYLSYGSGPKRFPLVDVLQYALEFASSKPVCTSPVDDIDASSPPSG
 481 SIPSQTLPSTTEQQGALSSELPSTSPSSVAAISSRSVIHKPFTQSRIPPDLPMHPAPRHI
 541 TEEELSVLESCLHRWRTEIENDTRDLQESISRIHRTIELMYSDKSMIQVPYRLHAVLVHE
 601 GQANAGHYWAYIFDHRESRWMKYNDIAVTKSSWEELVRDSFGGYRNASAYCLMYINDKAQ
 661 FLIQEEFNKETGQPLVGIETLPPDLRDFVEEDNQRFEKELEEWDAQLAQKALQEKLLASQ
 721 KLRESETSVTTAQAAGDPEYLEQPSRSDFSKHLKEETIQIITKASHEHEDKSPETVLQSA
 781 IKLEYARLVKLAQEDTPPETDYRLHHVVVYFIQNQAPKKIIEKTLLEQFGDRNLSFDERC
 841 HNIMKVAQAKLEMIKPEEVNLEEYEEWHQDYRKFRETTMYLIIGLENFQRESYIDSLLFL
 901 ICAYQNNKELLSKGLYRGHDEELISHYRRECLLKLNEQAAELFESGEDREVNNGLIIMNE
 961 FIVPFLPLLLVDEMEEKDILAVEDMRNRWCSYLGQEMEPHLQEKLTDFLPKLLDCSMEIK
1021 SFHEPPKLPSYSTHELCERFARIMLSLSRTPADGR
```

FIG._2

```
   1 CGGCAGCAAAGGAACGTGCGAACGCGTGACGCCGCCCGACTGGCTCGCGCTCTCCCGTGC
  61 CCCGGCGTCCTCCGCCCGCTCATGGCCCGGGCCGCCGCGGACGAGCGGCGCTGAGGCGGG
 121 CCGCGTGGAGACGTGAGGCGGCCGCCGTGGCCCTCACAGTCGGCGTTTCGCCGCCTGCCC
 181 GCGGTGCCCGCGCACGCCTGCCGCCATCGCCTTCGCGCCTGGCTGGCGGGGCGCTGTCC
 241 TCCCAGGCCGTCCGCGCCGCTCCCTGGAGCTCGGCGGAGCGCGGCAGCCAGGGCCGGCGG
 301 AGGCGCGAGGAGCCGGGCGCCACCGCCGCCGCCGCCGCCGCCGCGGGGGCCATGACC
 361 GTGGAGCAGAACGTGCTGCAGCAGAGCGCGGCGCAGAAGCACCAGCAGACGTTTTTGAAT
 421 CAACTGAGAGAAATTACGGGGATTAATGACACCCAGATACTACAGCAAGCCTTGAAGGAT
 481 AGTAATGGAAACTTGGAATTAGCAGTGGCTTTCCTTACTGCGAAGAATGCTAAGACCCCT
 541 CAGCAGGAGGAGACAACTTACTACCAAACAGCACTTCCTGGCAATGATAGATACATCAGT
 601 GTGGGAAGCCAAGCAGATACAAATGTGATTGATCTCACTGGAGATGATAAAGATGATCTT
 661 CAGAGAACAATTGCCTTGAGTTTGGCCGAATCAAACAGGGCATTCAGGGAGACTGGAATA
 721 ACTGATGAGGAACAAGCCATTAGCAGAGTTCTTGAAGCCAGTATAGCAGAGAATAAAGCA
 781 TGTTTGAAGAGGACACCTACAGAAGTTTGGAGGGATTCTCGAAACCCTTATGATAGAAAA
 841 AGACAGGACAAAGCTCCCGTTGGGCTAAAGAATGTTGGCAATACTTGTTGGTTTAGTGCT
 901 GTTATTCAGTCATTATTTAATCTTTTGGAATTTAGAAGATTAGTTCTGAATTACAAGCCT
 961 CCATCAAATGCTCAAGATTTACCCCGAAACCAAAAGGAACATCGGAATTTGCCTTTTATG
1021 CGTGAGCTGAGGTATCTATTTGCACTTCTTGTTGGTACCAAAAGGAAGTATGTTGATCCA
1081 TCAAGAGCAGTTGAAATTCTTAAGGATGCTTTCAAATCAAATGACTCACAGCAGCAAGAT
1141 GTGAGTGAGTTTACACACAAATTATTAGATTGGTTAGAAGATGCCTTCCAAATGAAAGCT
1201 GAAGAGGAGACGGATGAAGAGAAGCCAAAGAACCCCATGGTAGAGTTGTTCTATGGCAGA
1261 TTCCTGGCTGTGGGAGTACTTGAAGGTAAAAATTTGAAAACACTGAAATGTTTGGTCAG
1321 TACCCACTTCAGGTCAATGGGTTCAAAGATCTGCATGAGTGCCTAGAAGCTGCAATGATT
1381 GAAGGAGAAATTGAGTCTTTACATTCAGAGAATTCAGGAAAATCAGGCCAAGAGCATTGG
1441 TTTACTGGATTACCACCTGTGTTAACATTTGANTTGTCAAGATTTGAATTTAATCAGGCA
1501 TTGGGAAGACCAGAAAAAATTCACAACAAATTAGAATTTCCCCAAGTTTTATATTTGGAC
1561 AGATACATGCACAGAAACAGAGAAATAACAAGAATTAAGAGGGAAGAGATCAAGAGACTG
1621 AAAGATTACCTCACGGTATTACAACAAAGGCTAGAAAGATATTTAAGCTATGGTTCCGGT
1681 CCCAAACGATTCCCCTTGGTAGATGTTCTTCAGTATGCATTGGAATTTGCCTCAAGTAAA
1741 CCTGTTTGCACTTCTCCTGTTGACGATATTGACGCTAGTTCCCCACCTAGTGGTTCCATA
1801 CCATCACAGACATTACCAAGCACAACAGAACAACAGGGAGCCCTATCTTCAGAACTGCCA
1861 AGCACATCACCTTCATCAGTTGCTGCCATTTCATCGAGATCAGTAATACACAAACCATTT
1921 ACTCAGTCCCGGATACCTCCAGATTTGCCCATGCATCCGGCACCAAGGCACATAACGGAG
1981 GAAGAACTTTCTGTGCTGGAAAGTTGTTTACATCGCTGGAGGACAGAAATAGAAAATGAC
2041 ACCAGAGATTTGCAGGAAAGCATATCCAGAATCCATCGAACAATTGAATTAATGTACTCT
2101 GACAAATCTATGATACAAGTTCCTTATCGATTACATGCCGTTTTAGTTCACGAAGGCCAA
2161 GCTAATGCTGGGCACTACTGGGCATATATTTTTGATCATCGTGAAAGCAGATGGATGAAG
2221 TACAATGATATTGCTGTGACAAAATCATCATGGAAGAGCTAGTGAGGGACTCTTTTGGT
2281 GGTTATAGAAATGCCAGTGCATACTGTTTAATGTACATAAATGATAAGGCACAGTTCCTA
2341 ATACAAGAGGAGTTTAATAAAGAAACTGGGCAGCCCCTTGTTGGTATAGAAACATTACCA
2401 CCGGATTTGAGAGATTTTGTTGAGGAAGACAACCAACGATTTGAAAAAGAACTAGAAGAA
2461 TGGGATGCACAACTTGCCCAGAAAGCTTTGCAGGAAAAGCTTTTAGCGTCTCAGAAATTG
2521 AGAGAGTCAGAGACTTCTGTGACAACAGCACAAGCAGCAGGAGACCCAGAATATCTAGAG
2581 CAGCCATCAAGAAGTGATTTCTCAAAGCACTTGAAAGAAGAAACTATTCAAATAATTACC
2641 AAGGCATCACATGAGCATGAAGATAAAGTCCTGAAACAGTTTTGCAGTCGGCAATTAAG
2701 TTGAATATGCAAGGTTGGTTAAGTTGGCCCAAGAAGACACCCCACCAGAAACCGATTAT
2761 CGTTTACATCATGTAGTGGTCTACTTTATCCAGAACCAGGCACCAAAGAAAATTATTGAG
2821 AAAACATTACTAGAACAATTTGGAGATAGAAATTTGAGTTTTGATGAAAGGTGTCACAAC
2881 ATAATGAAAGTTGCTCAAGCCAAACTGGAAATGATAAAACCTGAAGAAGTAAACTTGGAG
2941 GAATATGAGGAGTGGCATCAGGATTATAGGAAATTCAGGGAAACAACTATGTATCTCATA
```

FIG._3A

```
3001 ATTGGGCTAGAAAATTTTCAAAGAGAAAGTTATATAGATTCCTTGCTGTTCCTCATCTGT
3061 GCTTATCAGAATAACAAAGAACTCTTGTCTAAAGGCTTATACAGAGGACATGATGAAGAA
3121 TTGATATCACATTATAGAAGAGAATGTTTGCTAATCCTTAATTTAAAAAGGAAACAAAAA
3181 CCTATTCTTTTTTTTTTCCTGCATTGCATTAAGAAATTAAATGAGCAAGCCGCAGAACTC
3241 TTCGAATCTGGAGAGGATCGAGAAGTAAACAATGGTTTGATTATCATGAATGAGTTTATT
3301 GTCCCATTTTTGCCATTATTACTGGTGGATGAAATGGAAGAAAAGGATATACTAGCTGTA
3361 GAAGATATGAGAAATCGATGGTGTTCCTACCTTGGTCAAGAAATGGAACCACACCTCCAA
3421 GAAAAGCTGACAGATTTTTTGCCAAAACTGCTTGATTGTTCTATGGAGATTAAAAGTTTC
3481 CATGAGCCACCGAAGTTACCTTCATATTCCACGCATGAACTCTGTGAGCGATTTGCCCGA
3541 ATCATGTTGTCCCTCAGTCGAACTCCTGCTGATGGAAGA<u>TAA</u>ACTGCACACTTTCCCTGA
3601 ACACACTGTATAAACTCTTTTTAGTTCTTAACCCTTGCCTTCCTGTCACAGGGTTTGCTT
3661 GTTGCTGCTATAGTTTTTAACTTTTTTTTATTTTAATAACTGCAAAAGACAAAATGACTA
3721 TACAGACTTTAGTCAGACTGCAGACAATAAAGCTGAAAATCGCATGGCGCTCAGACATTT
3781 TAACCGGAACTGATGTATAATCACAAATCTAATTGATTTTATTATGGCAAAACTATGCTT
3841 TTGCCACCTTCCTGTTGCAGTATTACTTTGCTTTTATCTTTTCTTTCTCAACAGCTTTCC
3901 ATTCAGTCTGGATCCTTCCATGACTACAGCCATTTAAGTGTTCAGCACTGTGTACGATAC
3961 ATAATATTTGGTAGCTTGTAAATGAAATAAAGAATAAAGTTTTATTTATGGCTAC
```

FIG._3B

```
   1 MTVEQNVLQQSAAQKHQQTFLNQLREITGINDTQILQQALKDSNGNLELAVAFLTAKNAK
  61 TPQQEETTYYQTALPGNDRYISVGSQADTNVIDLTGDDKDDLQRTIALSLAESNRAFRET
 121 GITDEEQAISRVLEASIAENKACLKRTPTEVWRDSRNPYDRKRQDKAPVGLKNVGNTCWF
 181 SAVIQSLFNLLEFRRLVLNYKPPSNAQDLPRNQKEHRNLPFMRELRYLFALLVGTKRKYV
 241 DPSRAVEILKDAFKSNDSQQQDVSEFTHKLLDWLEDAFQMKAEEETDEEKPKNPMVELFY
 301 GRFLAVGVLEGKKFENTEMFGQYPLQVNGFKDLHECLEAAMIEGEIESLHSENSGKSGQE
 361 HWFTGLPPVLTFXLSRFEFNQALGRPEKIHNKLEFPQVLYLDRYMHRNREITRIKREEIK
 421 RLKDYLTVLQQRLERYLSYGSGPKRFPLVDVLQYALEFASSKPVCTSPVDDIDASSPPSG
 481 SIPSQTLPSTTEQQGALSSELPSTSPSSVAAISSRSVIHKPFTQSRIPPDLPMHPAPRHI
 541 TEEELSVLESCLHRWRTEIENDTRDLQESISRIHRTIELMYSDKSMIQVPYRLHAVLVHE
 601 GQANAGHYWAYIFDHRESRWMKYNDIAVTKSSWEELVRDSFGGYRNASAYCLMYINDKAQ
 661 FLIQEEFNKETGQPLVGIETLPPDLRDFVEEDNQRFEKELEEWDAQLAQKALQEKLLASQ
 721 KLRESETSVTTAQAAGDPEYLEQPSRSDFSKHLKEETIQIITKASHEHEDKSPETVLQSA
 781 IKLEYARLVKLAQEDTPPETDYRLHHVVVYFIQNQAPKKIIEKTLLEQFGDRNLSFDERC
 841 HNIMKVAQAKLEMIKPEEVNLEEYEEWHQDYRKFRETTMYLIIGLENFQRESYIDSLLFL
 901 ICAYQNNKELLSKGLYRGHDEELISHYRRECLLILNLKRKQKPILFFFLHCIKKLNEQAA
 961 ELFESGEDREVNNGLIIMNEFIVPFLPLLLVDEMEEKDILAVEDMRNRWCSYLGQEMEPH
1021 LQEKLTDFLPKLLDCSMEIKSFHEPPKLPSYSTHELCERFARIMLSLSRTPADGR
```

FIG._4

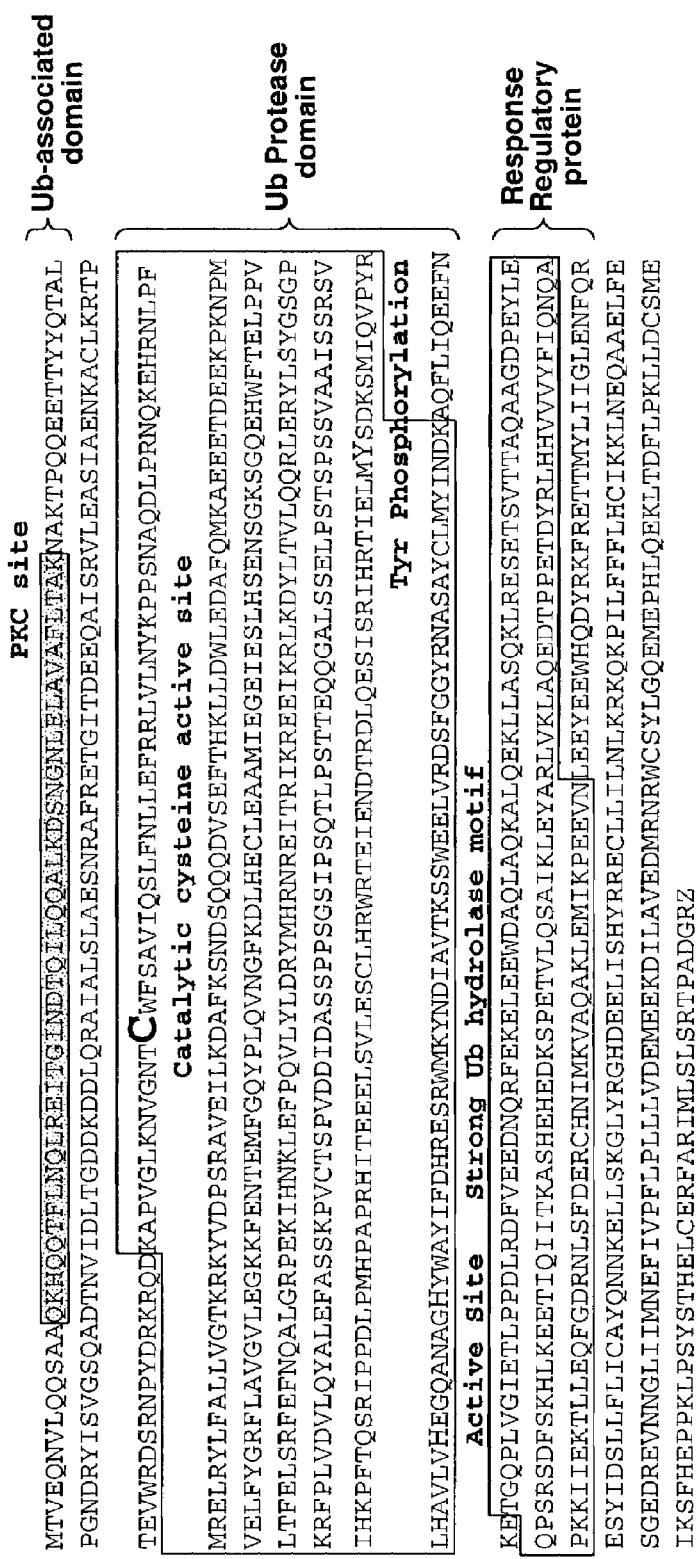
FIG._5 mtSUP Suppresses α-IgM Induced NFAT-Luciferase Activity as a Dominant-negative Mutant
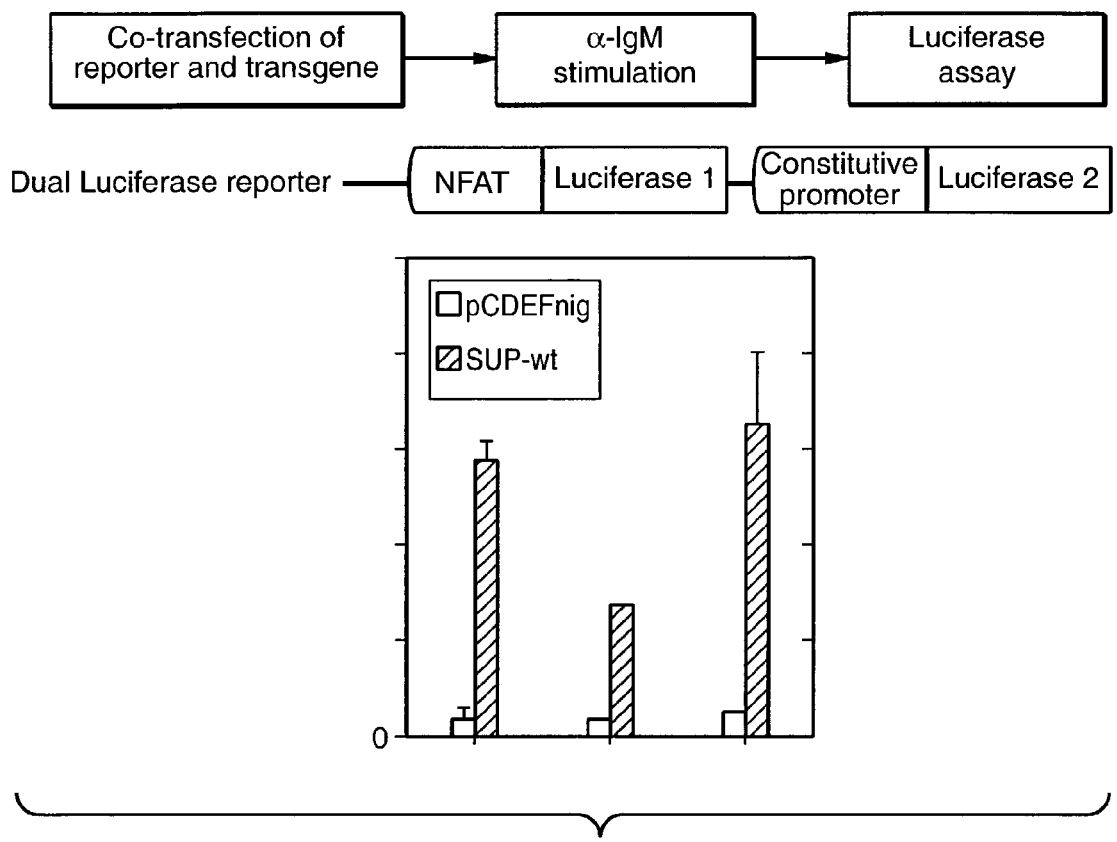
FIG._6
Model: SUP Regulates BCR Signaling by Stabilizing Syk
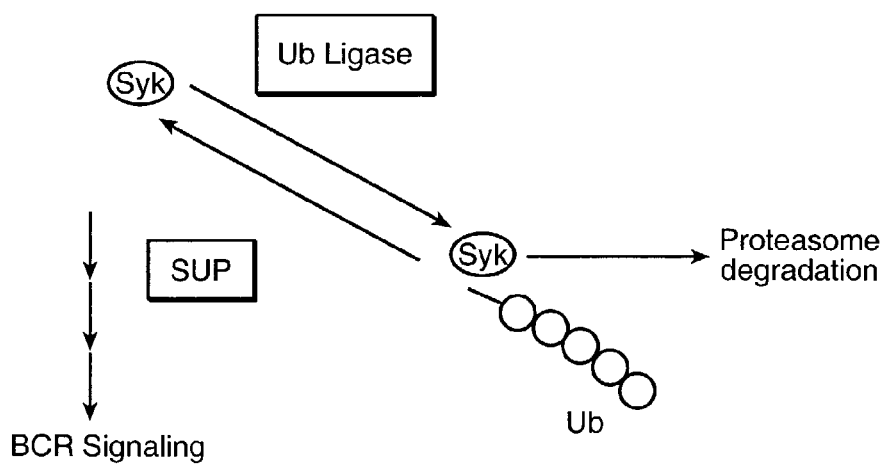
FIG._7

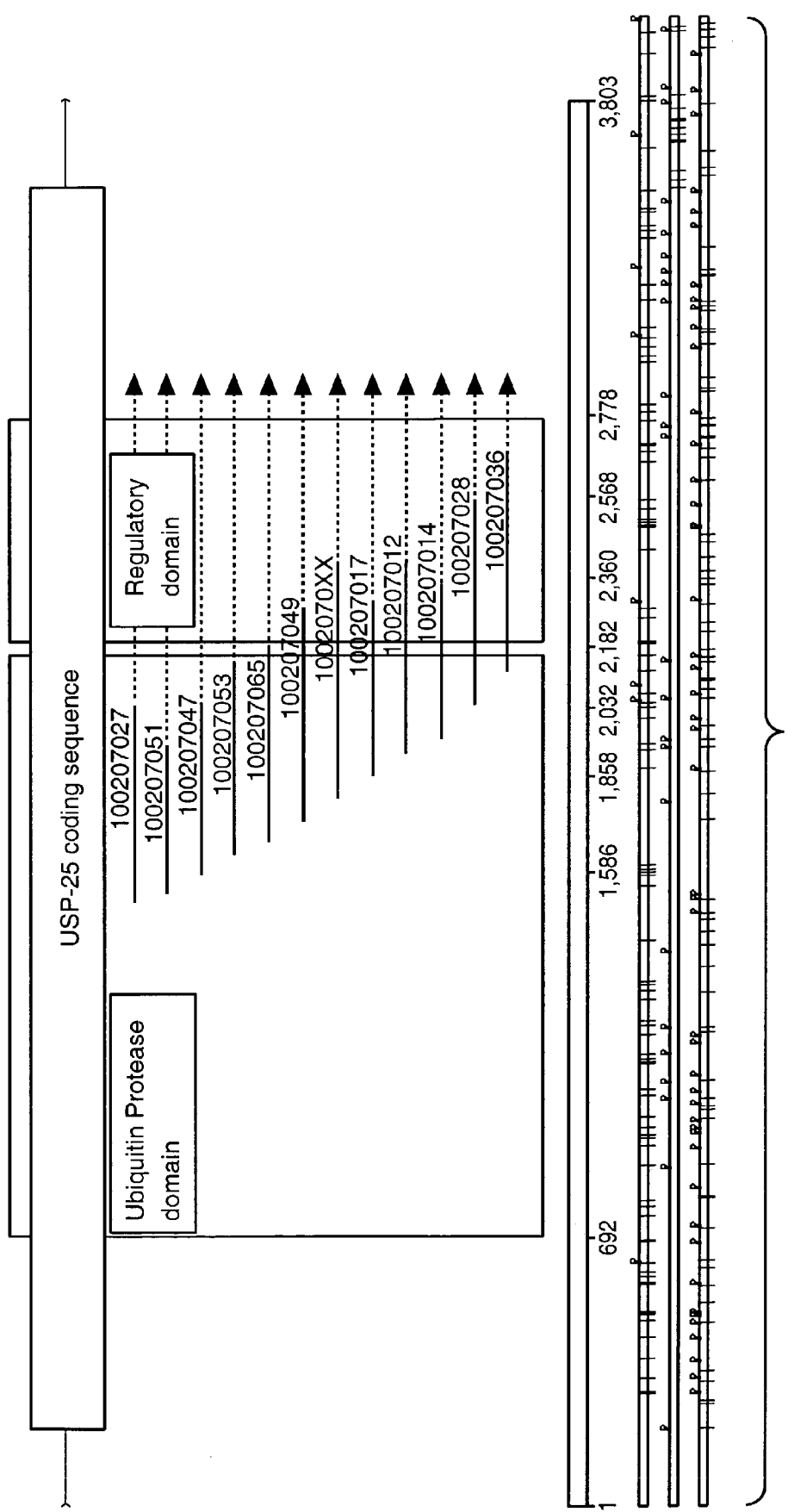
FIG._8

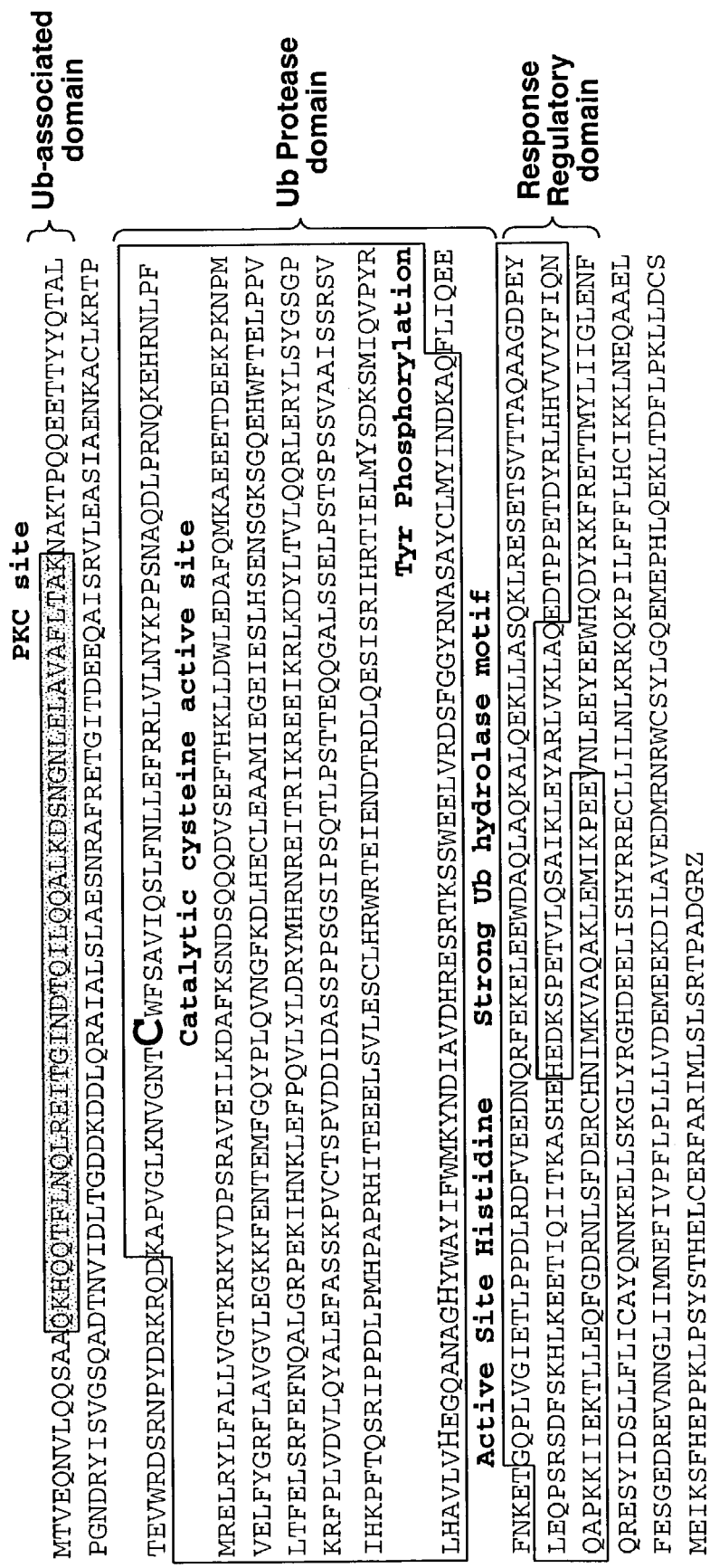
FIG._9A

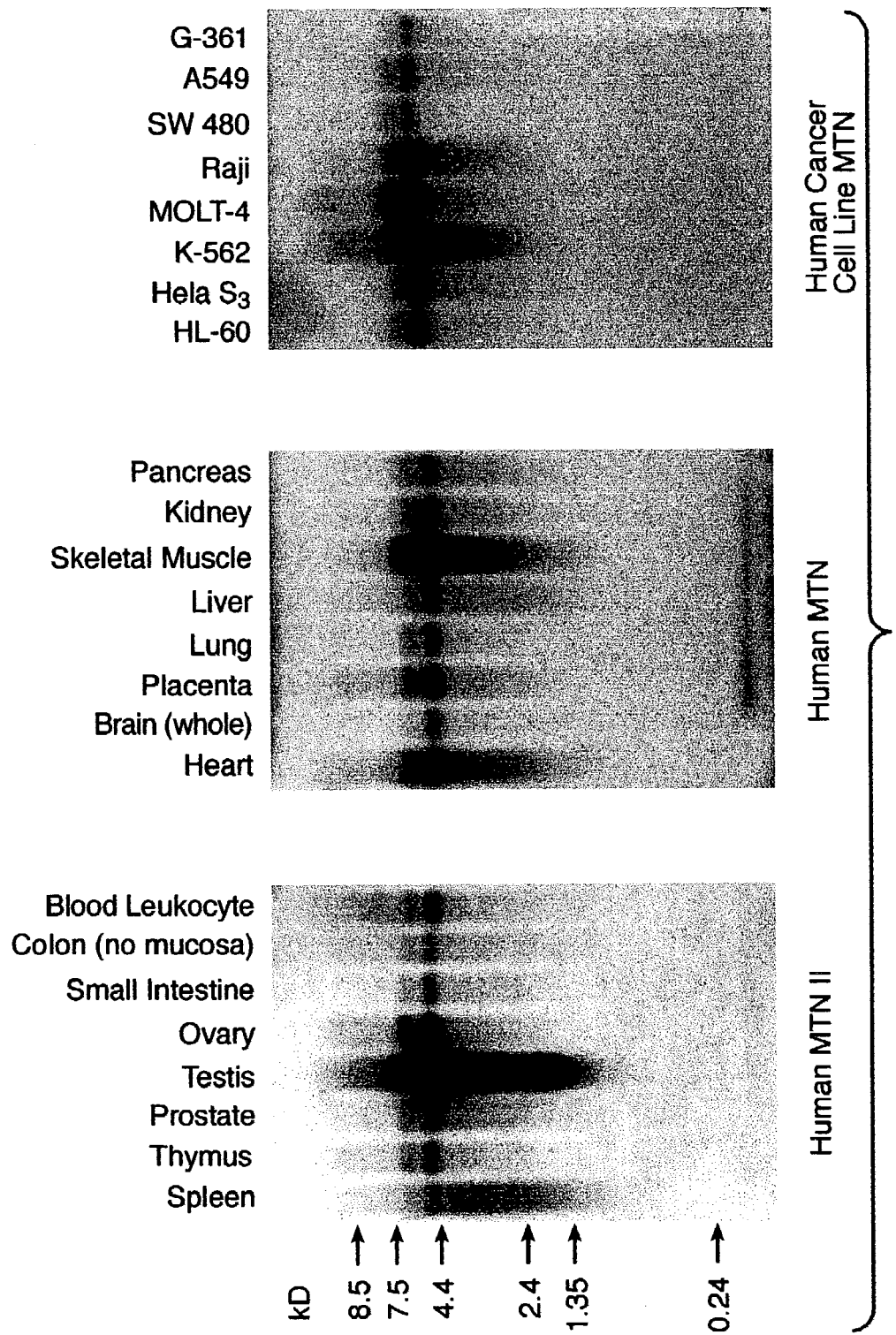
FIG._9B

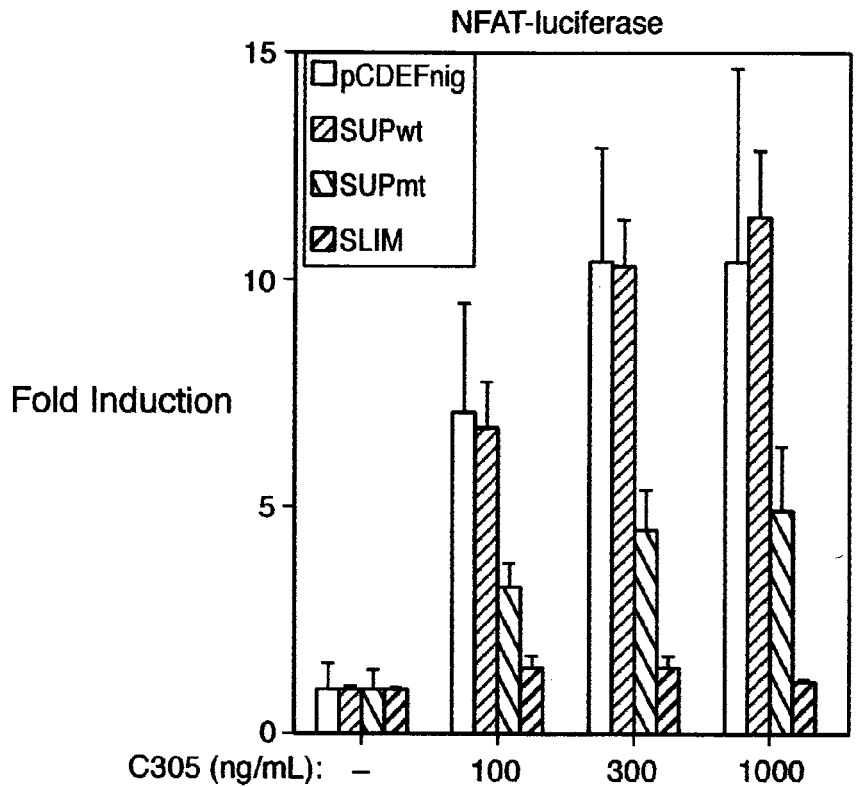
FIG._10A
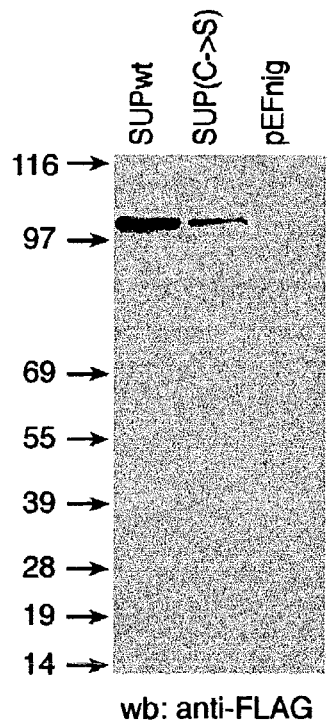
FIG._10B

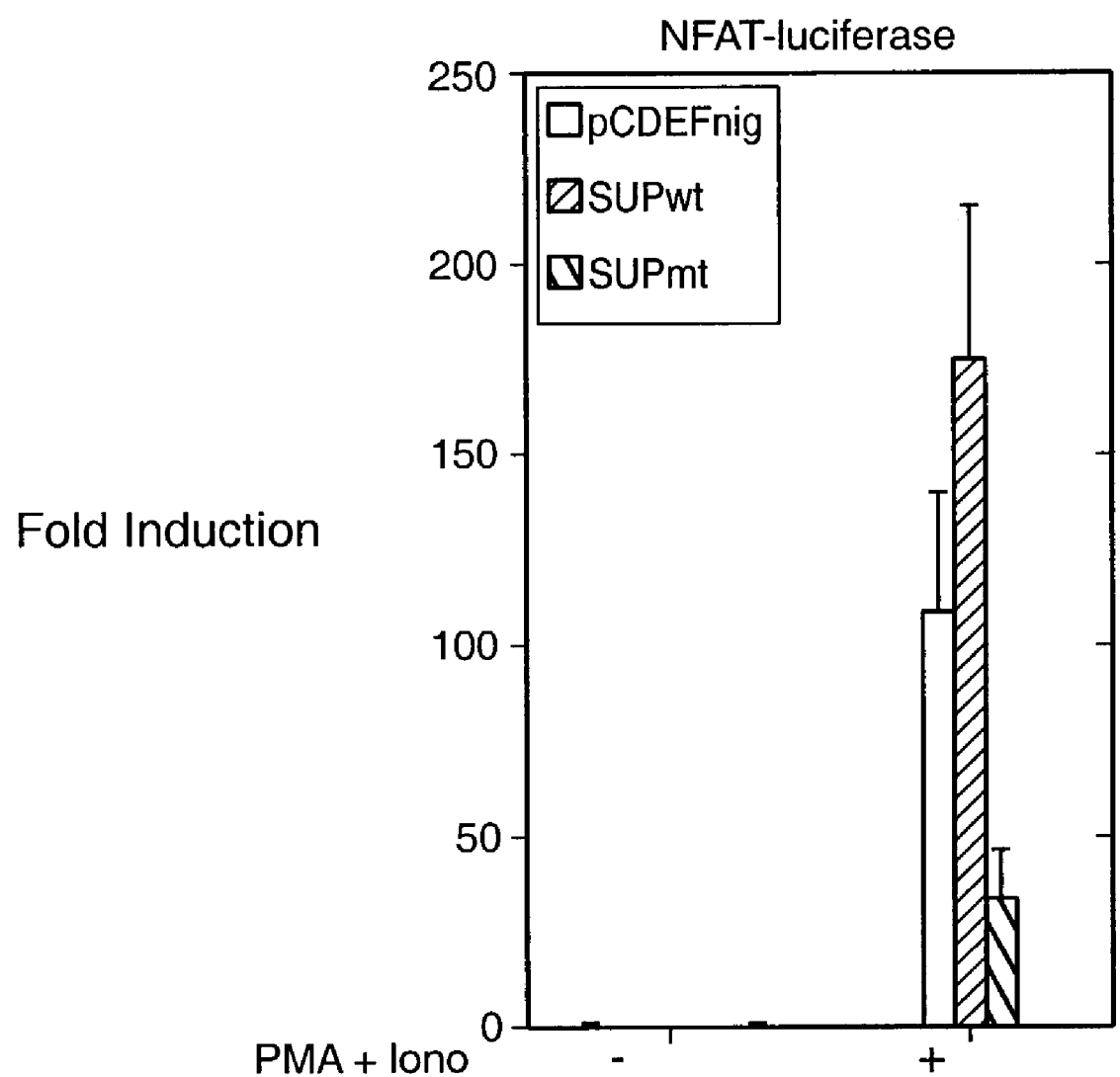
FIG._10C

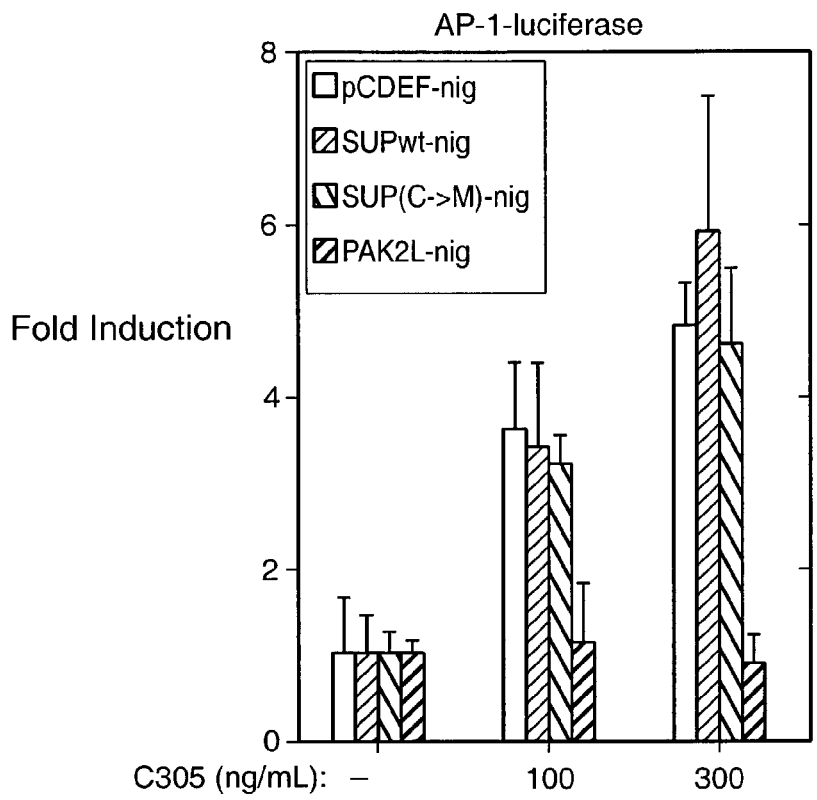
FIG._11A
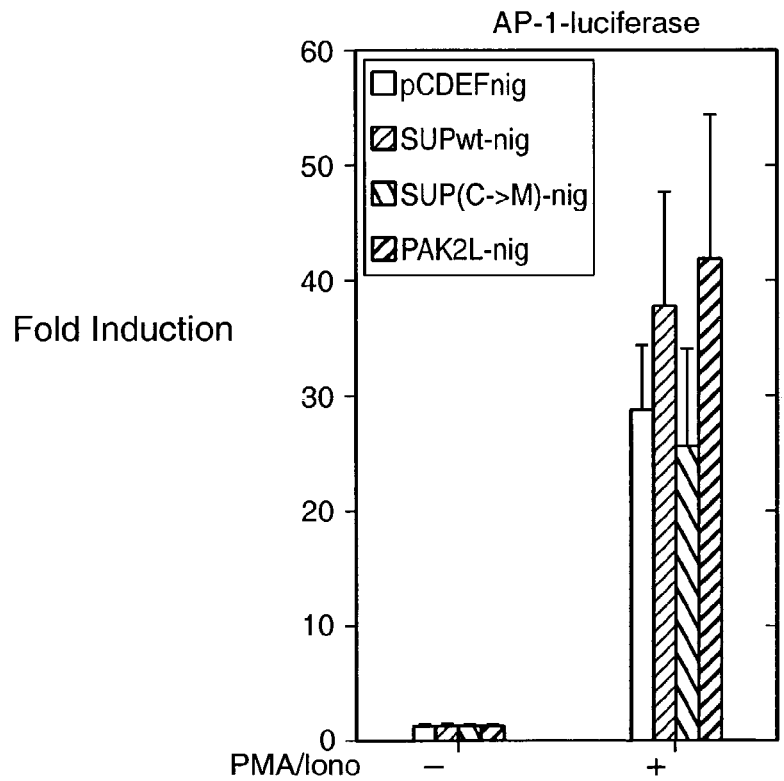
FIG._11B

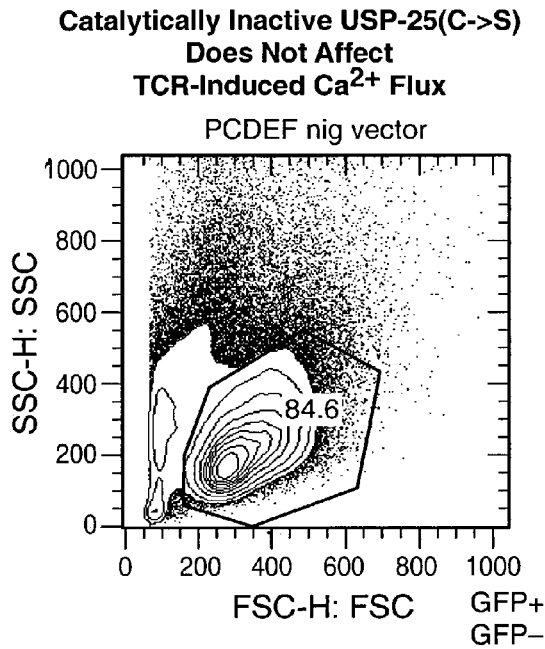
FIG._11C
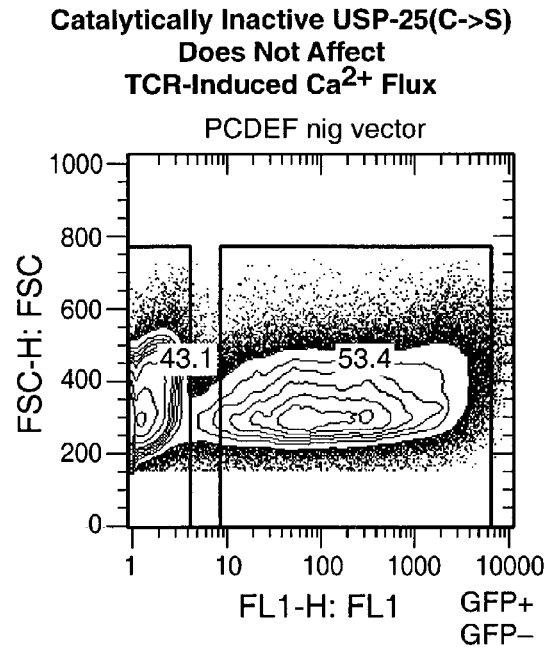
FIG._11D
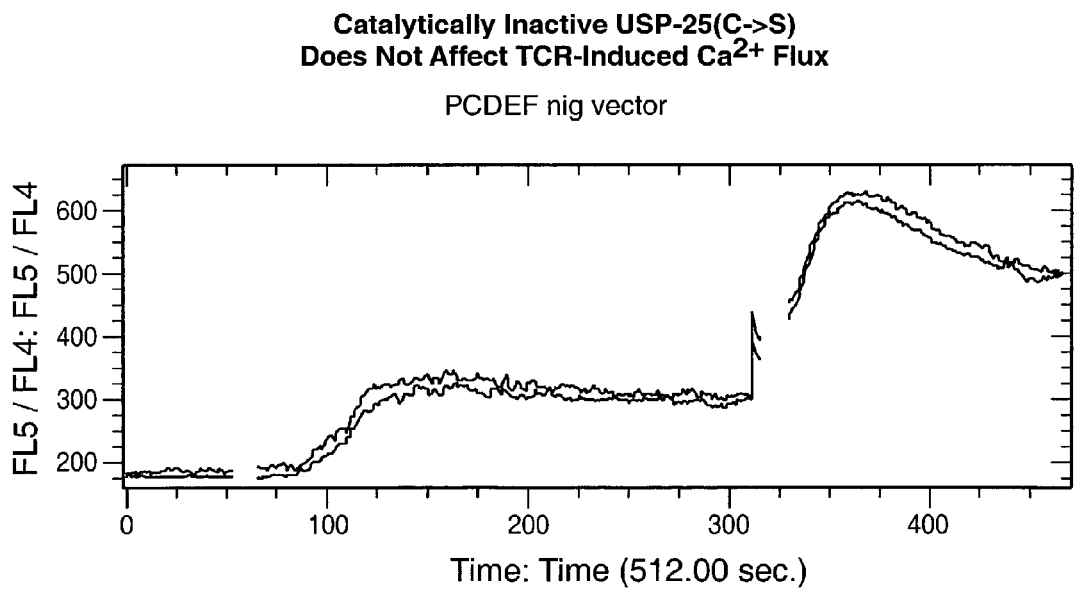
FIG._11E

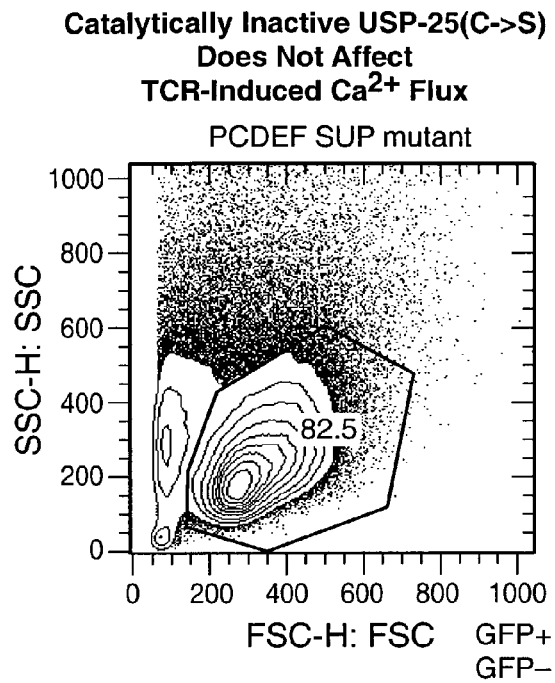
FIG._11F
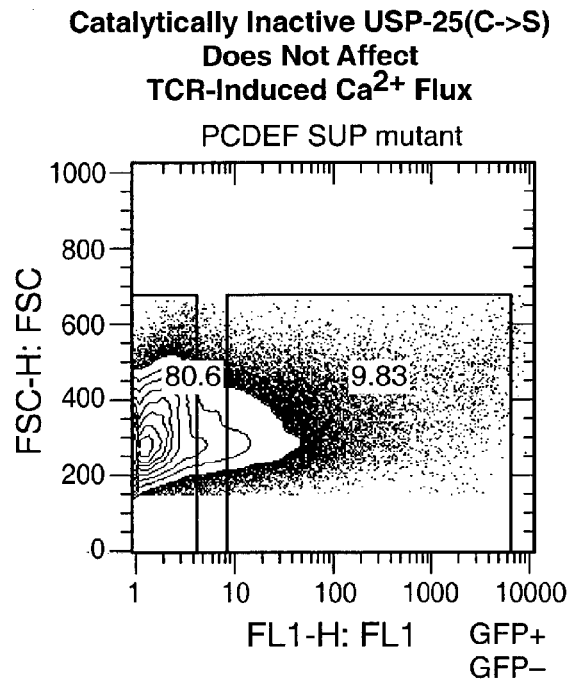
FIG._11G
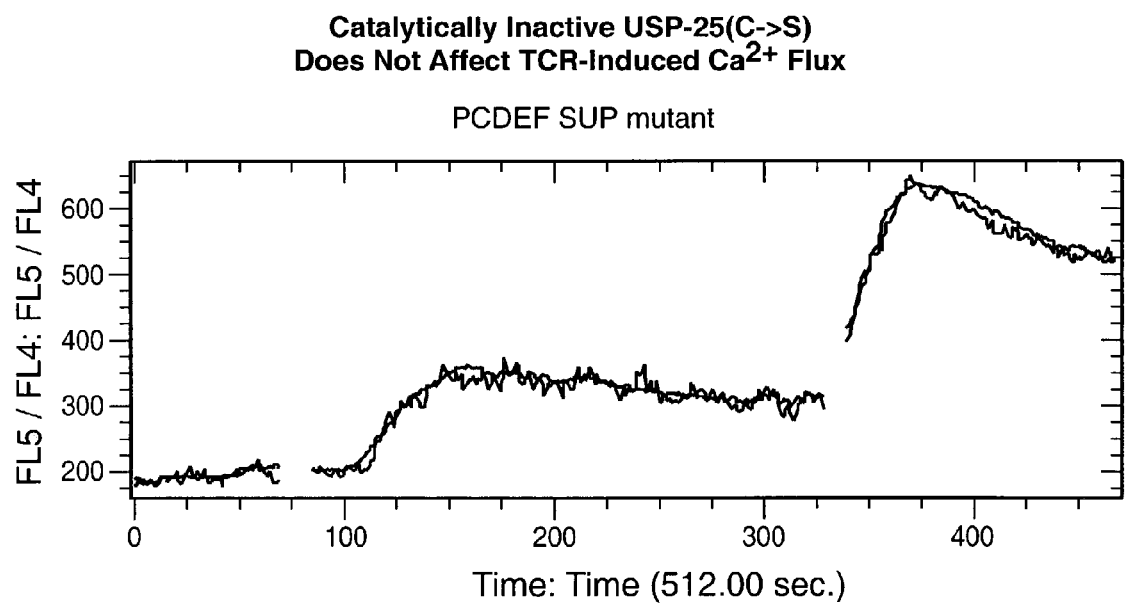
FIG._11H

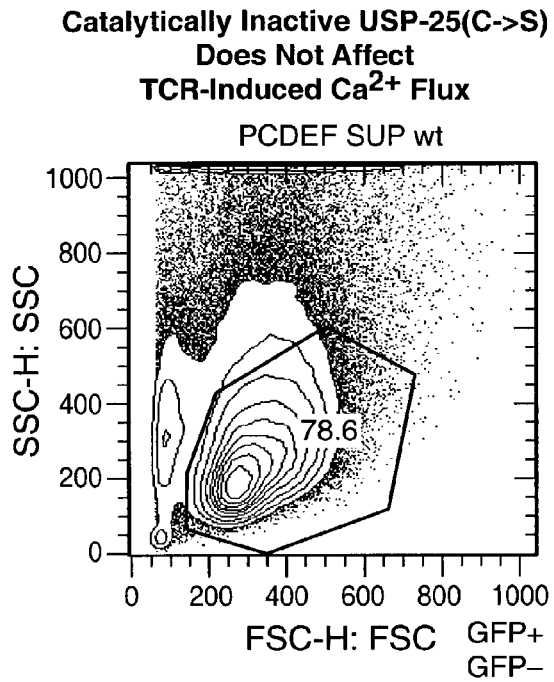
FIG._11I
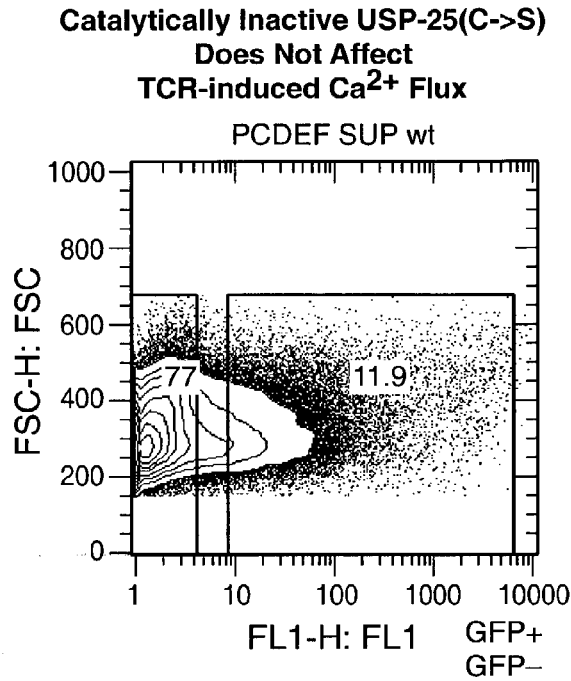
FIG._11J
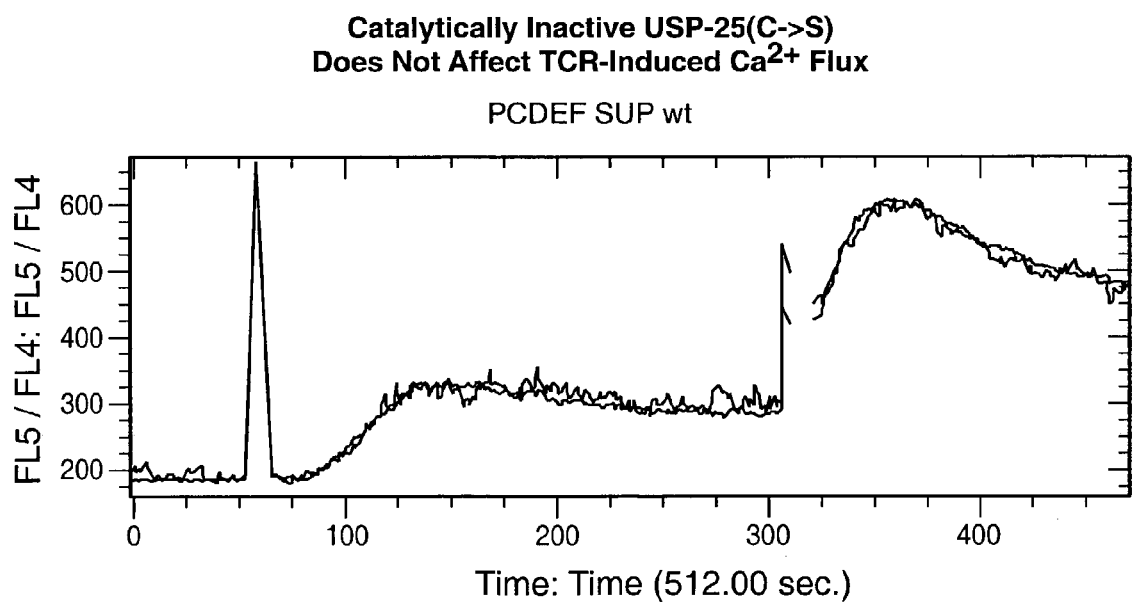
FIG._11K

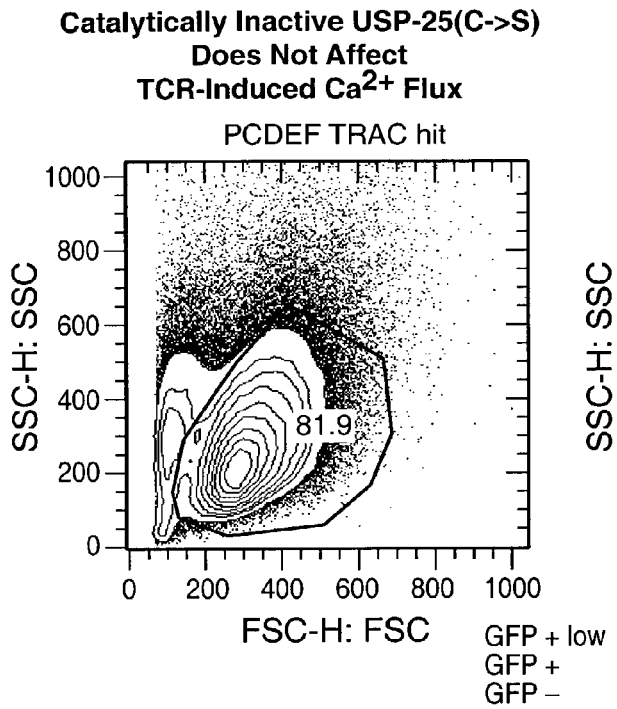
FIG._11L
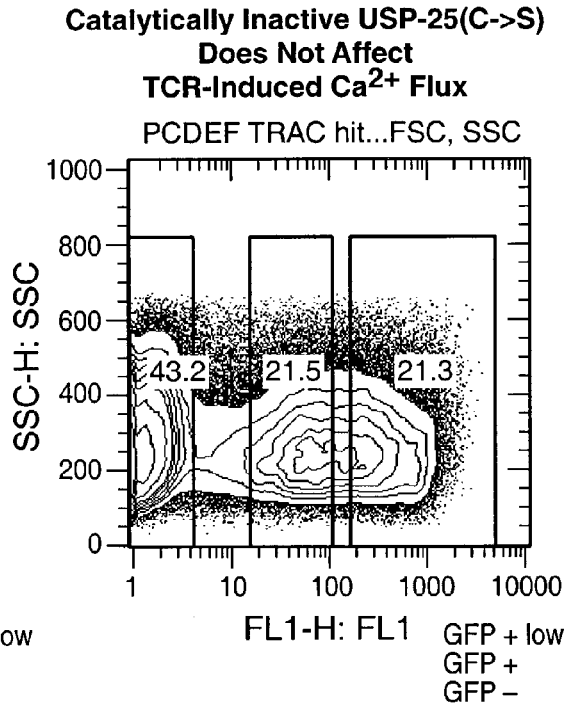
FIG._11M
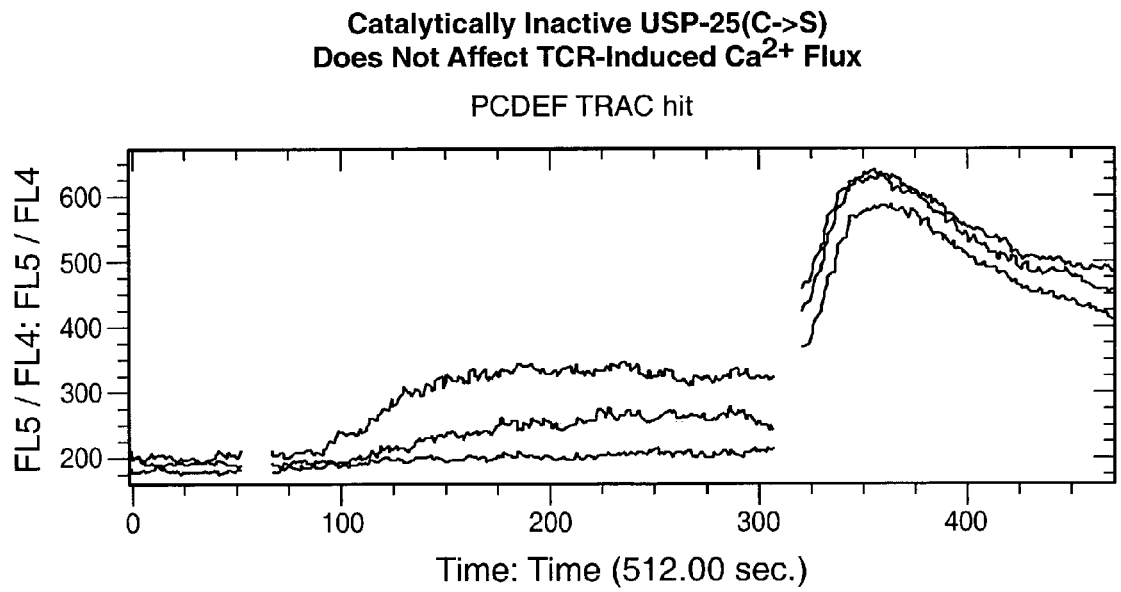
FIG._11N

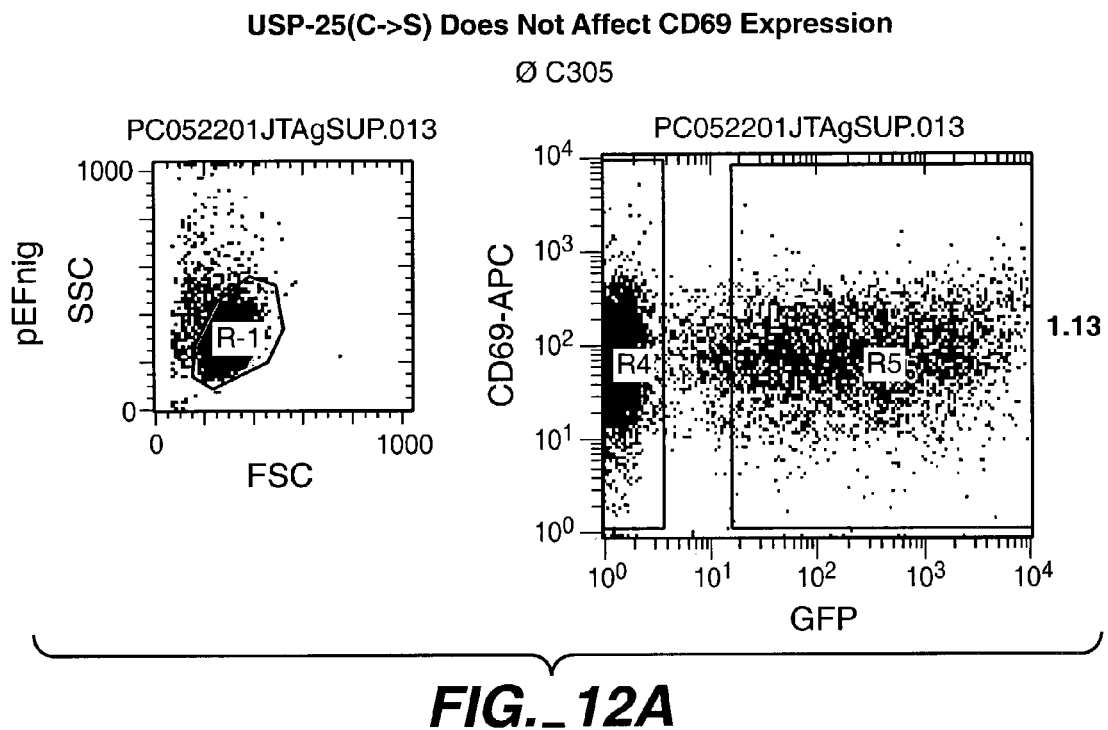
FIG._12A
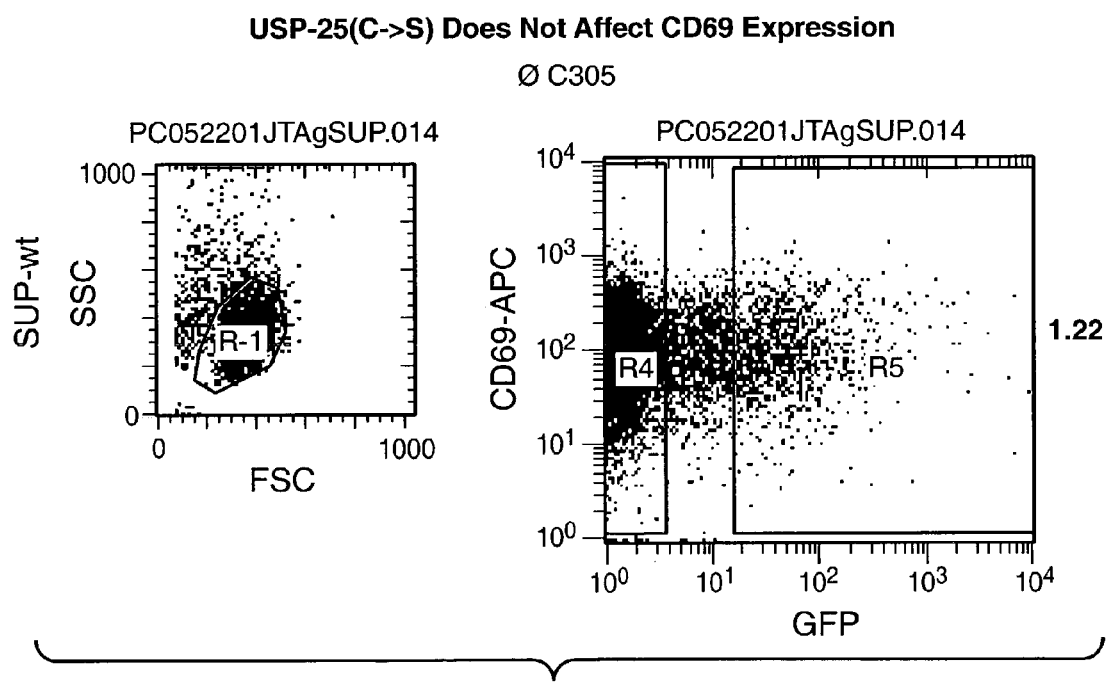
FIG._12B

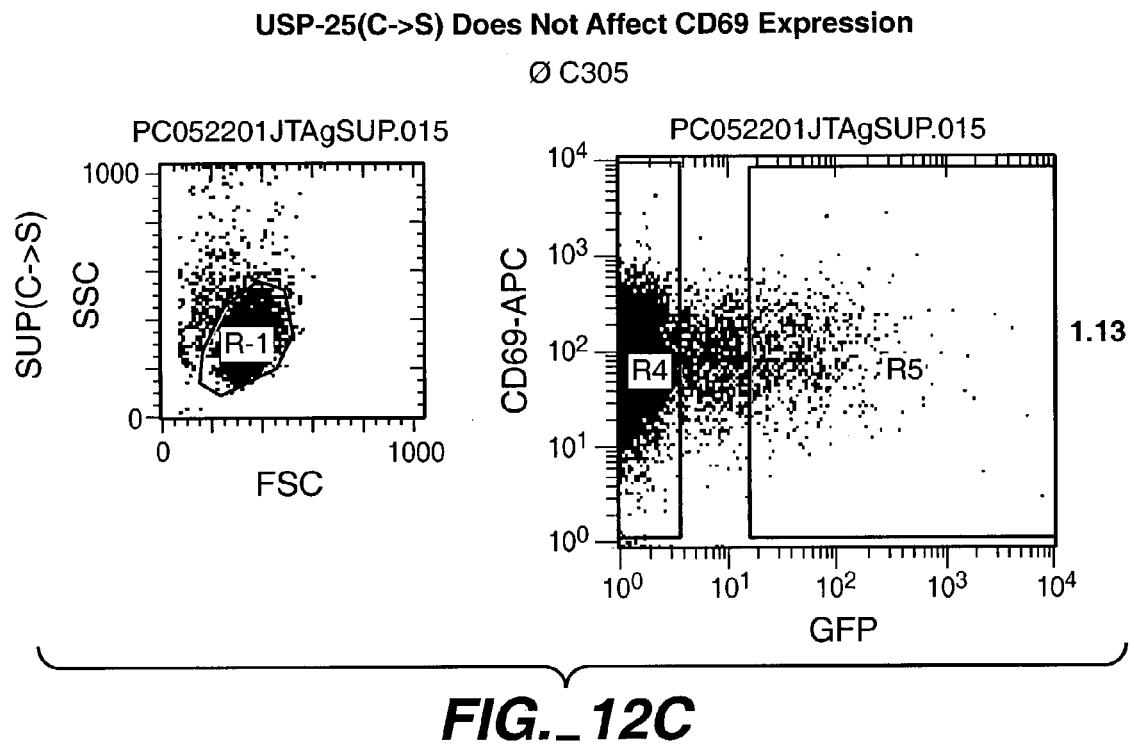
FIG._12C
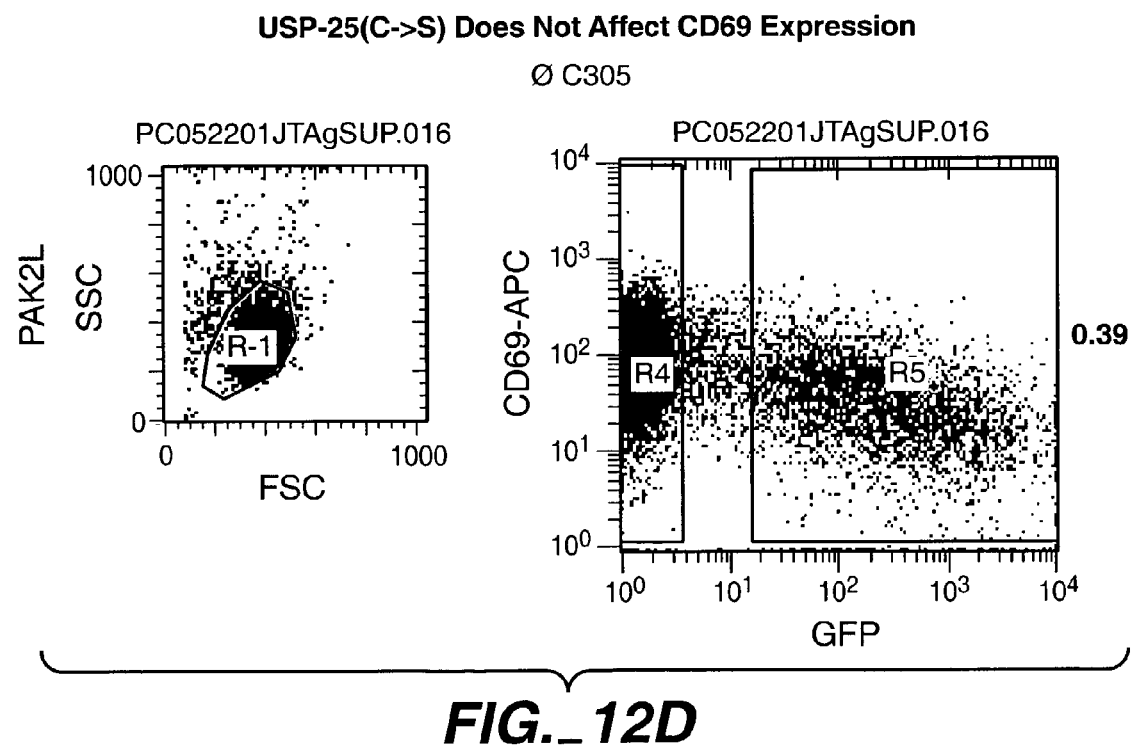
FIG._12D

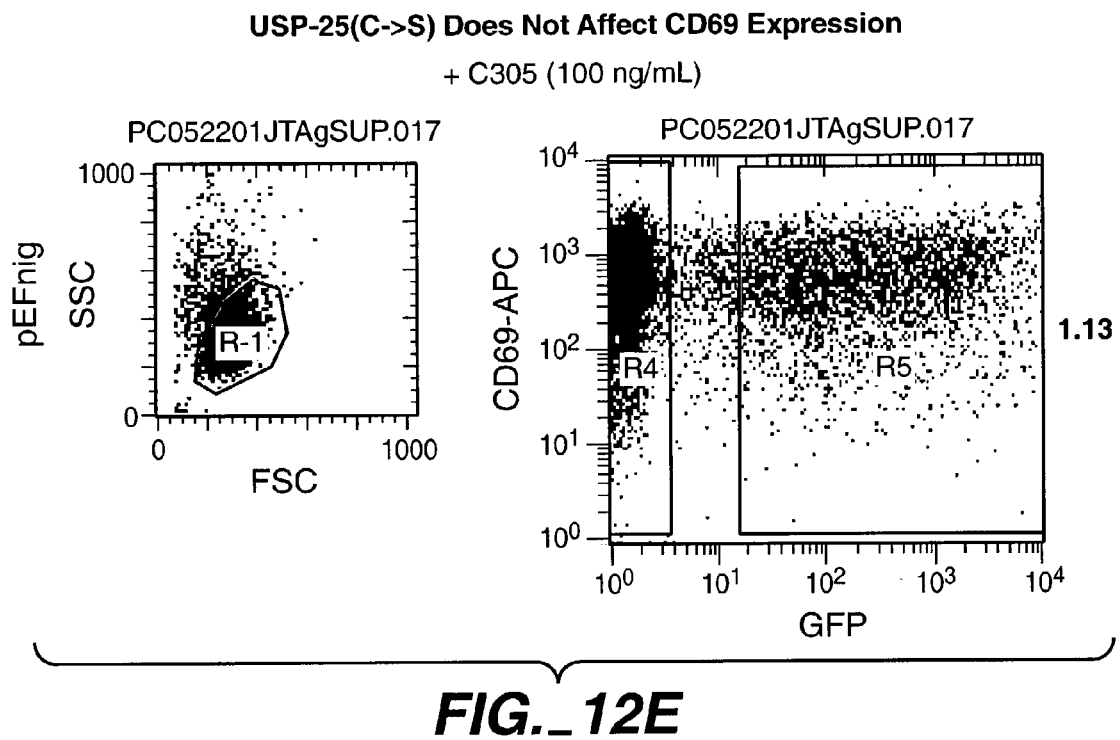
FIG._12E
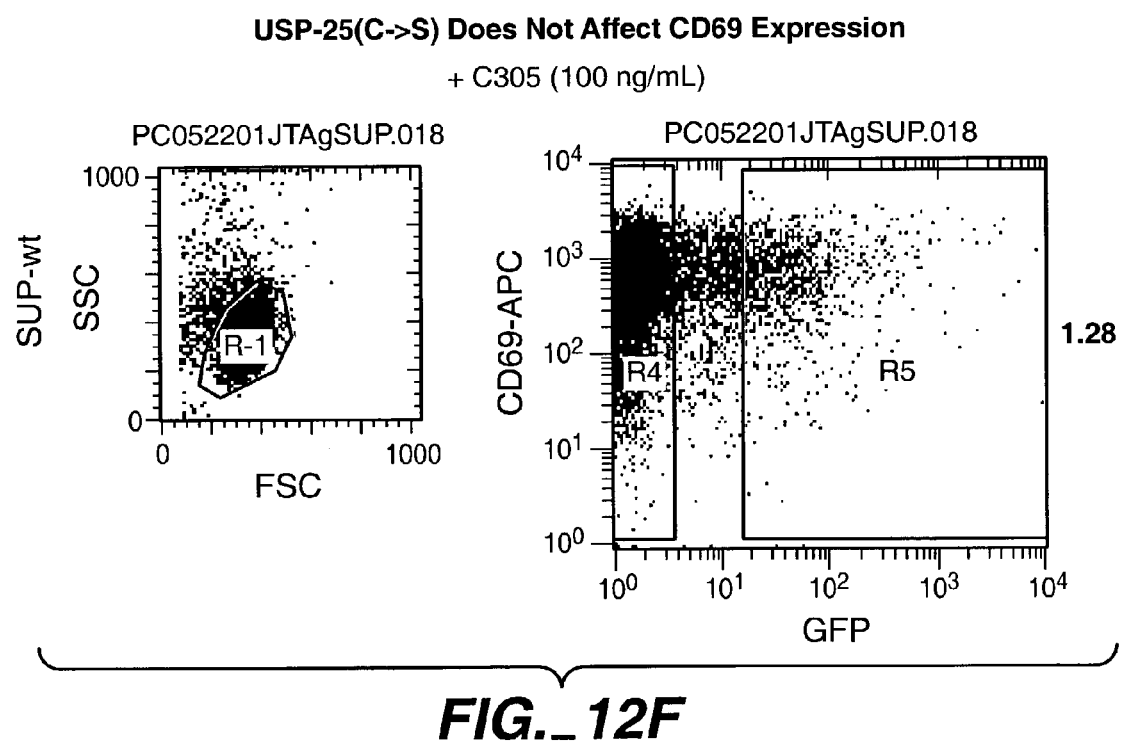
FIG._12F

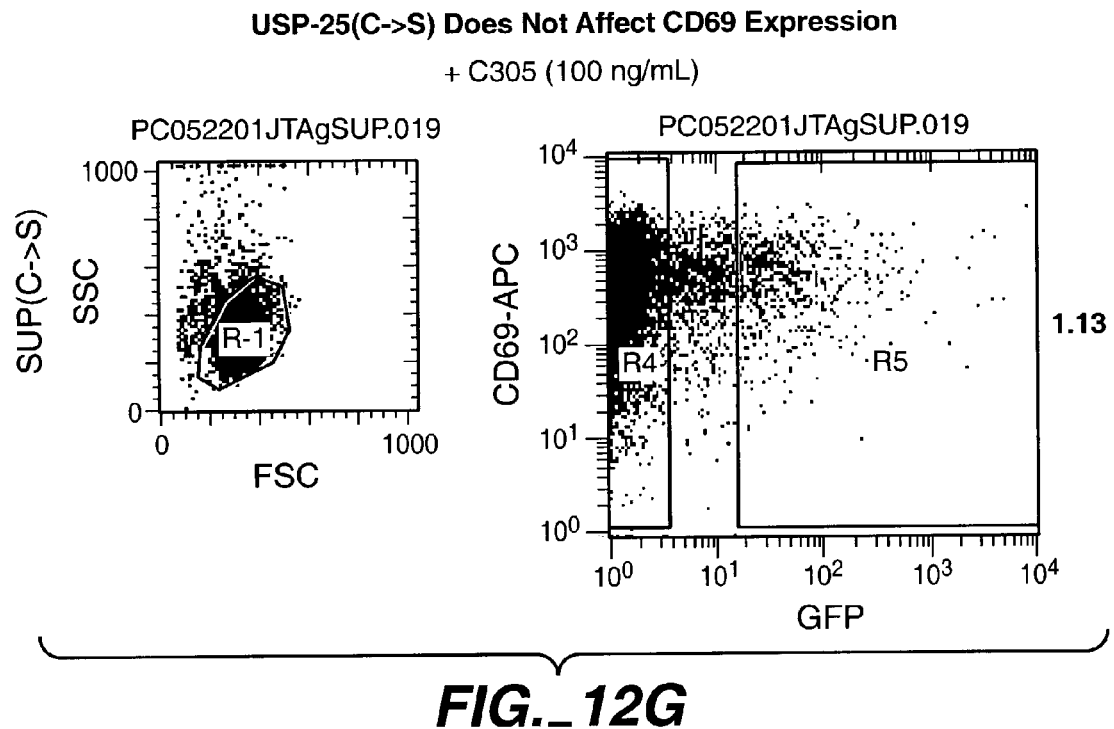
FIG._12G
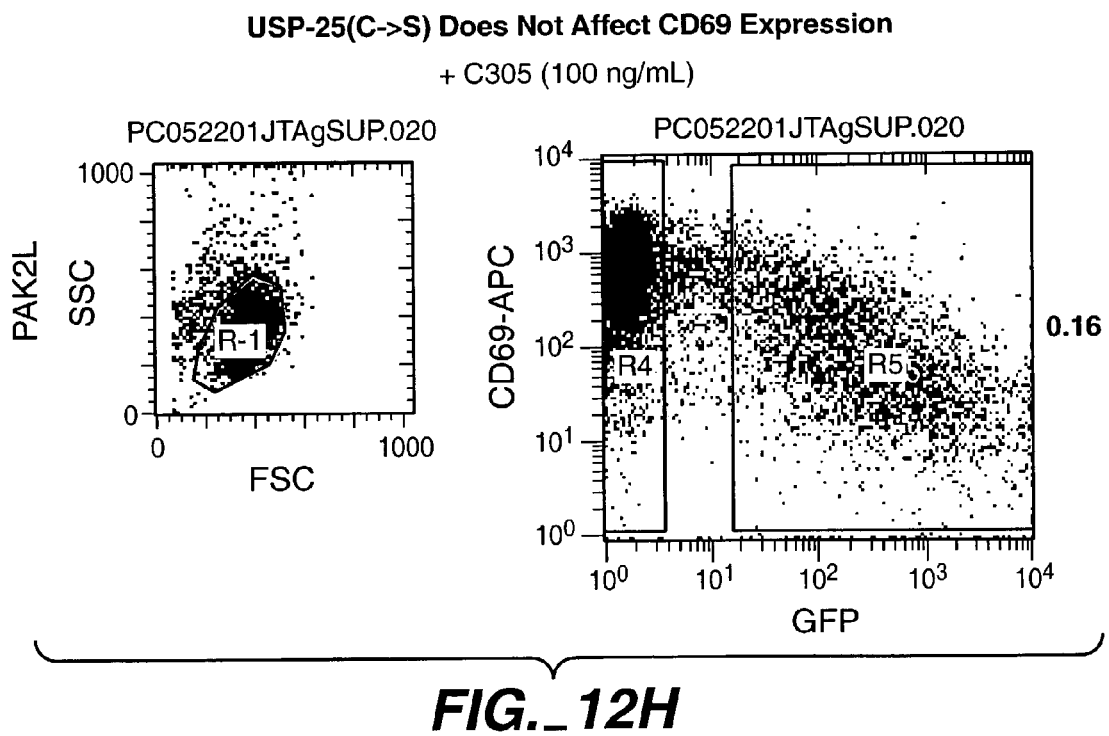
FIG._12H

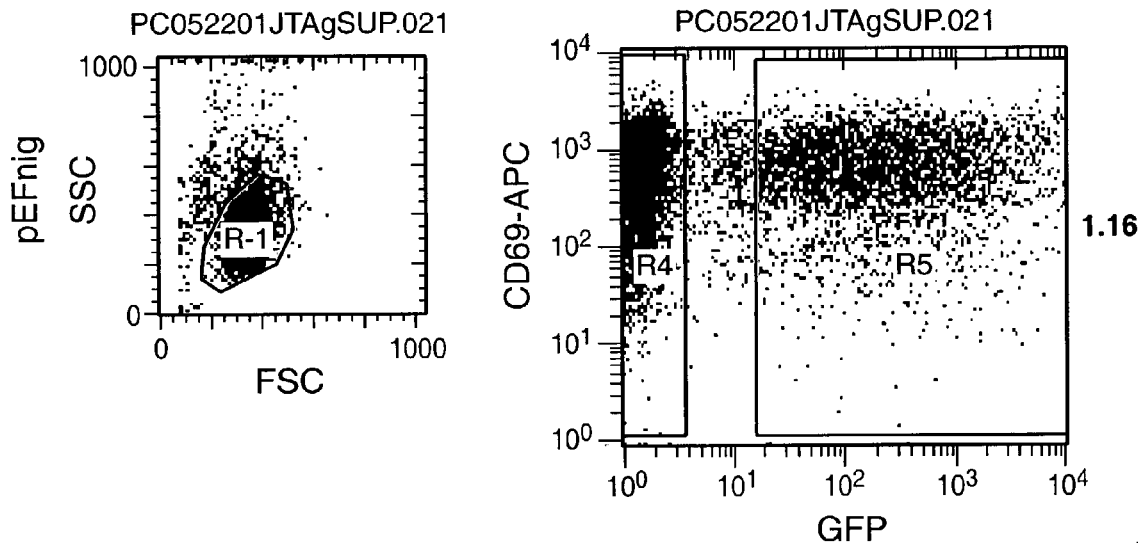
FIG._12I
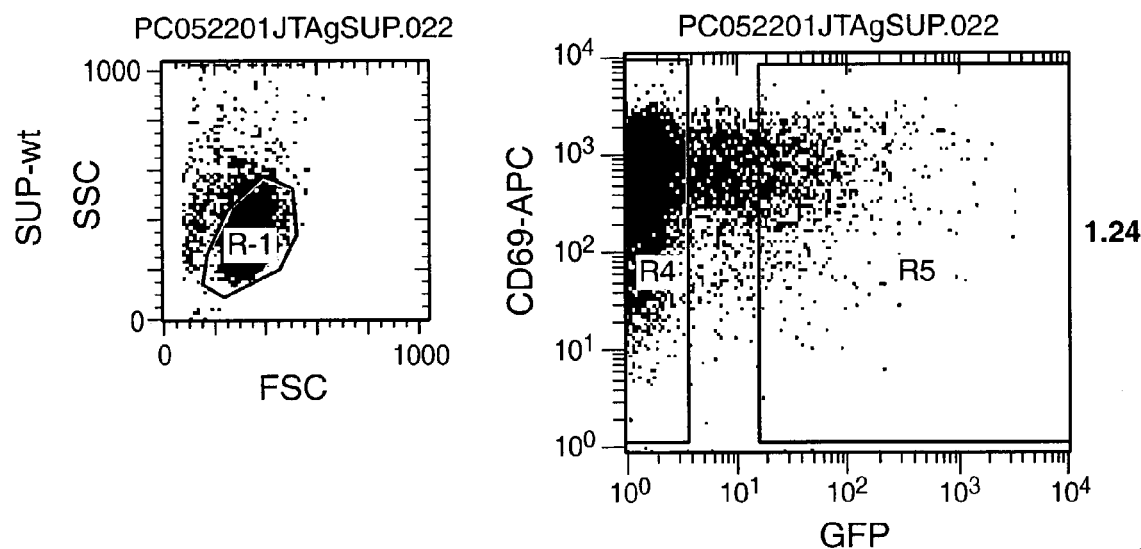
FIG._12J

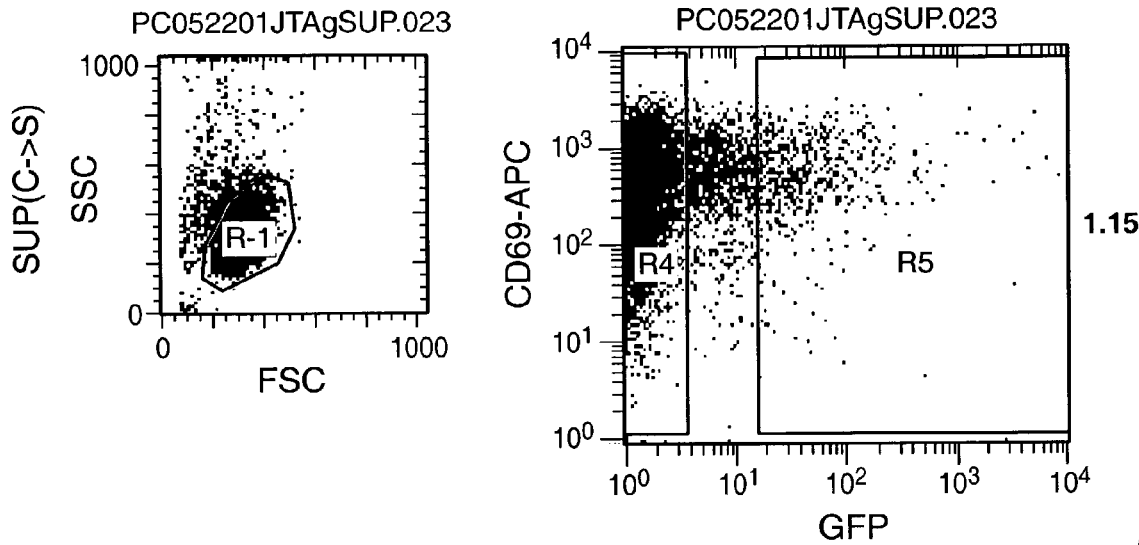
FIG._12K
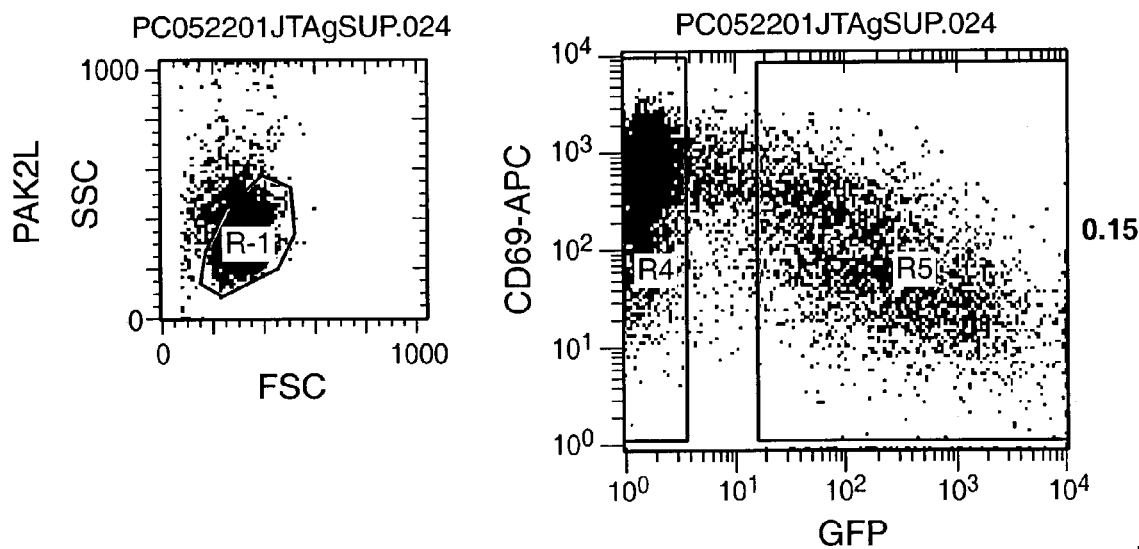
FIG._12L

N-Terminal USP-25 Truncation Mutants Inhibit NFAT Activity
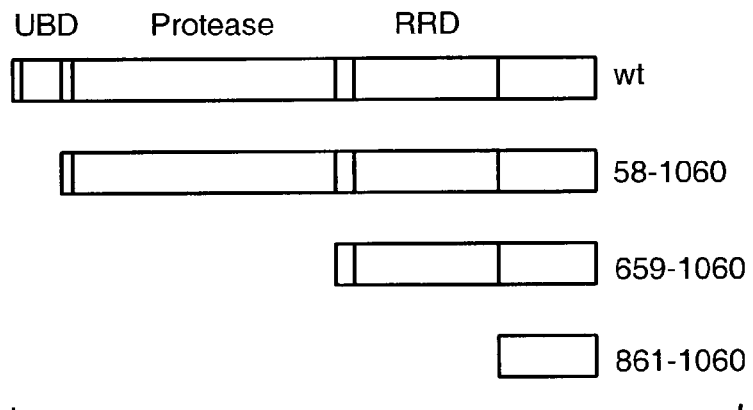
FIG._12M
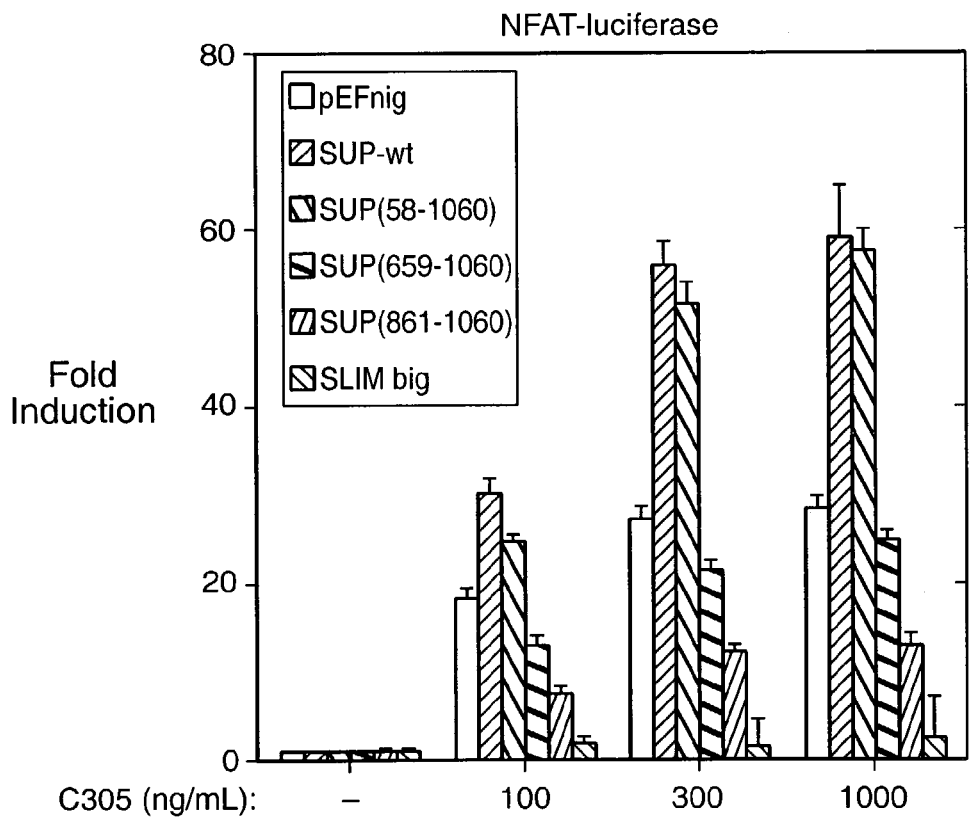
FIG._12N

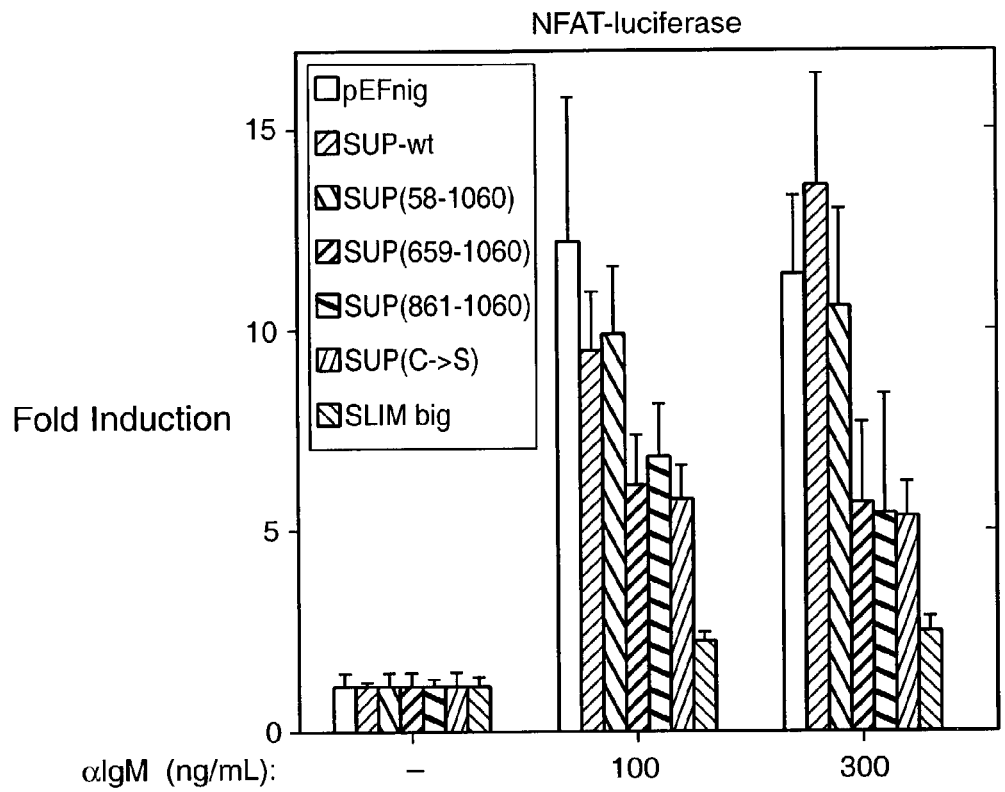
FIG._13A
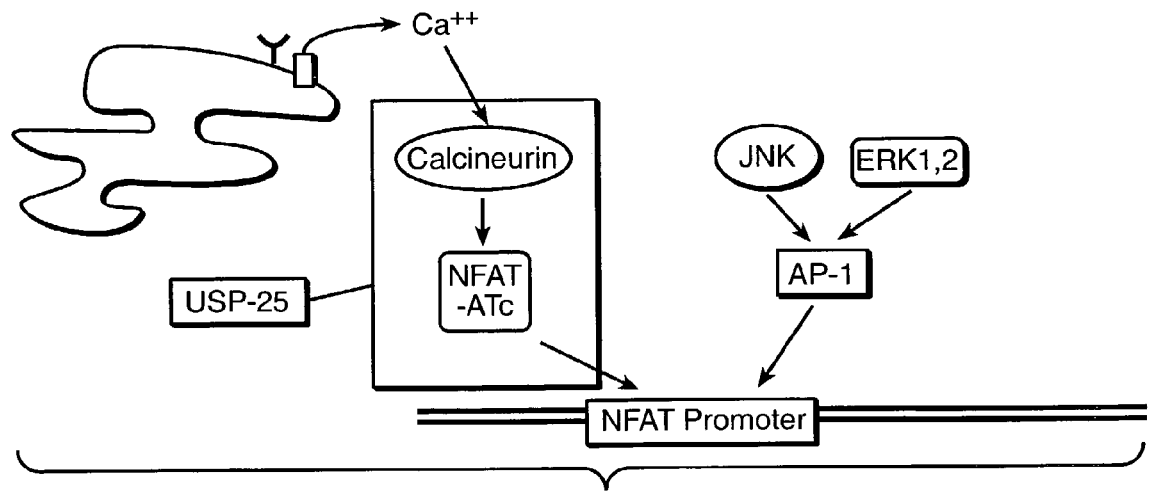
FIG._13B

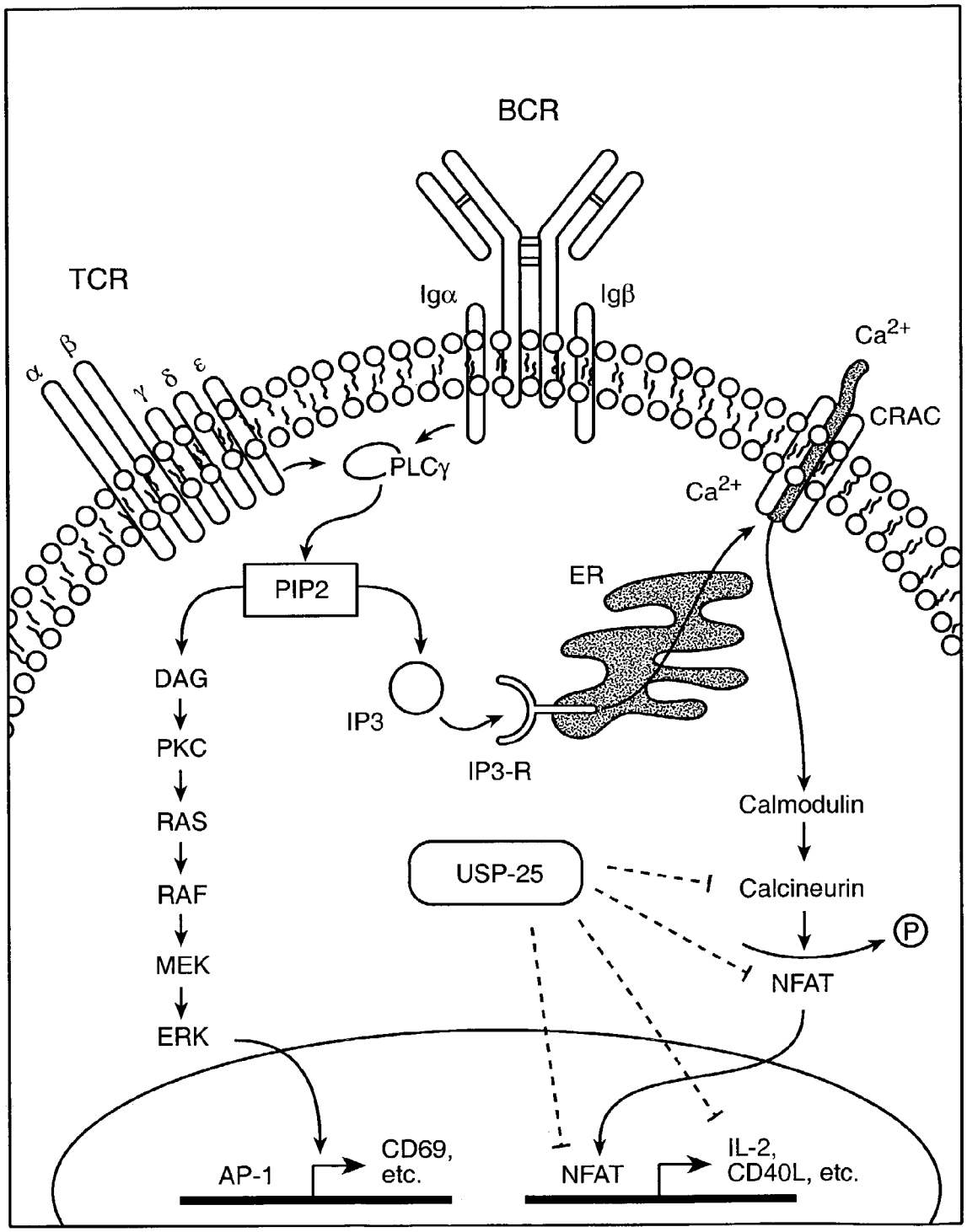
FIG._14

SEQUENCE LISTING

```
<160> NUMBER OF SEQ ID NOS: 5

<210> SEQ ID NO 1
<211> LENGTH: 3955
<212> TYPE: DNA
<213> ORGANISM: Homo sapiens
<220> FEATURE:
<221> NAME/KEY: misc_feature
<222> LOCATION: (1473)..(1473)
<223> OTHER INFORMATION: "n" at position 1473 can be any base.
<220> FEATURE:
<221> NAME/KEY: CDS
<222> LOCATION: (355)..(3522)
<223> OTHER INFORMATION:

<400> SEQUENCE: 1
cggcagcaaa ggaacgtgcg aacgcgtgac gccgcccgac tggctcgcgc tctcccgtgc       60
cccggcgtcc tccgcccgct catggcccgg gccgccgcgg acgagcggcg ctgaggcggg      120
ccgcgtggag acgtgaggcg gccgccgtgg ccctcacagt cggcgtttcg ccgcctgccc      180
gcggtgcccg cgcacgcctg ccgccatcgc cttcgcgcct ggctggcggg ggcgctgtcc      240
tcccaggccg tccgcgccgc tccctggagc tcggcggagc gcggcagcca gggccggcgg      300
aggcgcgagg agccgggcgc caccgccgcc gccgccgccg ccgccgcggg ggcc atg       357
                                                              Met
                                                                1
```

-continued

| | | |
|---|---|---|
| acc gtg gag cag aac gtg ctg cag cag agc gcg gcg cag aag cac cag<br>Thr Val Glu Gln Asn Val Leu Gln Gln Ser Ala Ala Gln Lys His Gln<br>       5                        10                   15 | 405 |
| cag acg ttt ttg aat caa ctg aga gaa att acg ggg att aat gac acc<br>Gln Thr Phe Leu Asn Gln Leu Arg Glu Ile Thr Gly Ile Asn Asp Thr<br>   20                    25                 30 | 453 |
| cag ata cta cag caa gcc ttg aag gat agt aat gga aac ttg gaa tta<br>Gln Ile Leu Gln Gln Ala Leu Lys Asp Ser Asn Gly Asn Leu Glu Leu<br>35                   40                 45 | 501 |
| gca gtg gct ttc ctt act gcg aag aat gct aag acc cct cag cag gag<br>Ala Val Ala Phe Leu Thr Ala Lys Asn Ala Lys Thr Pro Gln Gln Glu<br>50                 55               60              65 | 549 |
| gag aca act tac tac caa aca gca ctt cct ggc aat gat aga tac atc<br>Glu Thr Thr Tyr Tyr Gln Thr Ala Leu Pro Gly Asn Asp Arg Tyr Ile<br>                 70               75               80 | 597 |
| agt gtg gga agc caa gca gat aca aat gtg att gat ctc act gga gat<br>Ser Val Gly Ser Gln Ala Asp Thr Asn Val Ile Asp Leu Thr Gly Asp<br>         85                 90               95 | 645 |
| gat aaa gat gat ctt cag aga aca att gcc ttg agt ttg gcc gaa tca<br>Asp Lys Asp Asp Leu Gln Arg Thr Ile Ala Leu Ser Leu Ala Glu Ser<br>        100                105             110 | 693 |
| aac agg gca ttc agg gag act gga ata act gat gag gaa caa gcc att<br>Asn Arg Ala Phe Arg Glu Thr Gly Ile Thr Asp Glu Glu Gln Ala Ile<br>115               120             125 | 741 |
| agc aga gtt ctt gaa gcc agt ata gca gag aat aaa gca tgt ttg aag<br>Ser Arg Val Leu Glu Ala Ser Ile Ala Glu Asn Lys Ala Cys Leu Lys<br>130               135             140             145 | 789 |
| agg aca cct aca gaa gtt tgg agg gat tct cga aac cct tat gat aga<br>Arg Thr Pro Thr Glu Val Trp Arg Asp Ser Arg Asn Pro Tyr Asp Arg<br>                150              155             160 | 837 |
| aaa aga cag gac aaa gct ccc gtt ggg cta aag aat gtt ggc aat act<br>Lys Arg Gln Asp Lys Ala Pro Val Gly Leu Lys Asn Val Gly Asn Thr<br>        165                170             175 | 885 |
| tgt tgg ttt agt gct gtt att cag tca tta ttt aat ctt ttg gaa ttt<br>Cys Trp Phe Ser Ala Val Ile Gln Ser Leu Phe Asn Leu Leu Glu Phe<br>180               185             190 | 933 |
| aga aga tta gtt ctg aat tac aag cct cca tca aat gct caa gat tta<br>Arg Arg Leu Val Leu Asn Tyr Lys Pro Pro Ser Asn Ala Gln Asp Leu<br>      195              200              205 | 981 |
| ccc cga aac caa aag gaa cat cgg aat ttg cct ttt atg cgt gag ctg<br>Pro Arg Asn Gln Lys Glu His Arg Asn Leu Pro Phe Met Arg Glu Leu<br>210               215             220             225 | 1029 |
| agg tat cta ttt gca ctt ctt gtt ggt acc aaa agg aag tat gtt gat<br>Arg Tyr Leu Phe Ala Leu Leu Val Gly Thr Lys Arg Lys Tyr Val Asp<br>            230              235             240 | 1077 |
| cca tca aga gca gtt gaa att ctt aag gat gct ttc aaa tca aat gac<br>Pro Ser Arg Ala Val Glu Ile Leu Lys Asp Ala Phe Lys Ser Asn Asp<br>              245              250             255 | 1125 |
| tca cag cag caa gat gtg agt gag ttt aca cac aaa tta tta gat tgg<br>Ser Gln Gln Gln Asp Val Ser Glu Phe Thr His Lys Leu Leu Asp Trp<br>        260                265             270 | 1173 |
| tta gaa gat gcc ttc caa atg aaa gct gaa gag gag acg gat gaa gag<br>Leu Glu Asp Ala Phe Gln Met Lys Ala Glu Glu Glu Thr Asp Glu Glu<br>275               280             285 | 1221 |
| aag cca aag aac ccc atg gta gag ttg ttc tat ggc aga ttc ctg gct<br>Lys Pro Lys Asn Pro Met Val Glu Leu Phe Tyr Gly Arg Phe Leu Ala<br>290               295             300             305 | 1269 |
| gtg gga gta ctt gaa ggt aaa aaa ttt gaa aac act gaa atg ttt ggt<br>Val Gly Val Leu Glu Gly Lys Lys Phe Glu Asn Thr Glu Met Phe Gly<br>            310              315             320 | 1317 |

-continued

| | |
|---|---|
| cag tac cca ctt cag gtc aat ggg ttc aaa gat ctg cat gag tgc cta<br>Gln Tyr Pro Leu Gln Val Asn Gly Phe Lys Asp Leu His Glu Cys Leu<br>               325                           330                     335 | 1365 |
| gaa gct gca atg att gaa gga gaa att gag tct tta cat tca gag aat<br>Glu Ala Ala Met Ile Glu Gly Glu Ile Glu Ser Leu His Ser Glu Asn<br>          340                       345                     350 | 1413 |
| tca gga aaa tca ggc caa gag cat tgg ttt act gga tta cca cct gtg<br>Ser Gly Lys Ser Gly Gln Glu His Trp Phe Thr Gly Leu Pro Pro Val<br>355                         360                         365 | 1461 |
| tta aca ttt gan ttg tca aga ttt gaa ttt aat cag gca ttg gga aga<br>Leu Thr Phe Xaa Leu Ser Arg Phe Glu Phe Asn Gln Ala Leu Gly Arg<br>370                     375                     380                 385 | 1509 |
| cca gaa aaa att cac aac aaa tta gaa ttt ccc caa gtt tta tat ttg<br>Pro Glu Lys Ile His Asn Lys Leu Glu Phe Pro Gln Val Leu Tyr Leu<br>                     390                     395                     400 | 1557 |
| gac aga tac atg cac aga aac aga gaa ata aca aga att aag agg gaa<br>Asp Arg Tyr Met His Arg Asn Arg Glu Ile Thr Arg Ile Lys Arg Glu<br>          405                       410                     415 | 1605 |
| gag atc aag aga ctg aaa gat tac ctc acg gta tta caa caa agg cta<br>Glu Ile Lys Arg Leu Lys Asp Tyr Leu Thr Val Leu Gln Gln Arg Leu<br>               420                       425                     430 | 1653 |
| gaa aga tat tta agc tat ggt tcc ggt ccc aaa cga ttc ccc ttg gta<br>Glu Arg Tyr Leu Ser Tyr Gly Ser Gly Pro Lys Arg Phe Pro Leu Val<br>435                     440                         445 | 1701 |
| gat gtt ctt cag tat gca ttg gaa ttt gcc tca agt aaa cct gtt tgc<br>Asp Val Leu Gln Tyr Ala Leu Glu Phe Ala Ser Ser Lys Pro Val Cys<br>450                     455                     460                 465 | 1749 |
| act tct cct gtt gac gat att gac gct agt tcc cca cct agt ggt tcc<br>Thr Ser Pro Val Asp Asp Ile Asp Ala Ser Ser Pro Pro Ser Gly Ser<br>                     470                     475                     480 | 1797 |
| ata cca tca cag aca tta cca agc aca aca gaa caa cag gga gcc cta<br>Ile Pro Ser Gln Thr Leu Pro Ser Thr Thr Glu Gln Gln Gly Ala Leu<br>          485                       490                     495 | 1845 |
| tct tca gaa ctg cca agc aca tca cct tca tca gtt gct gcc att tca<br>Ser Ser Glu Leu Pro Ser Thr Ser Pro Ser Ser Val Ala Ala Ile Ser<br>               500                       505                     510 | 1893 |
| tcg aga tca gta ata cac aaa cca ttt act cag tcc cgg ata cct cca<br>Ser Arg Ser Val Ile His Lys Pro Phe Thr Gln Ser Arg Ile Pro Pro<br>515                     520                     525 | 1941 |
| gat ttg ccc atg cat ccg gca cca agg cac ata acg gag gaa gaa ctt<br>Asp Leu Pro Met His Pro Ala Pro Arg His Ile Thr Glu Glu Glu Leu<br>530                     535                     540                 545 | 1989 |
| tct gtg ctg gaa agt tgt tta cat cgc tgg agg aca gaa ata gaa aat<br>Ser Val Leu Glu Ser Cys Leu His Arg Trp Arg Thr Glu Ile Glu Asn<br>               550                       555                     560 | 2037 |
| gac acc aga gat ttg cag gaa agc ata tcc aga atc cat cga aca att<br>Asp Thr Arg Asp Leu Gln Glu Ser Ile Ser Arg Ile His Arg Thr Ile<br>          565                       570                     575 | 2085 |
| gaa tta atg tac tct gac aaa tct atg ata caa gtt cct tat cga tta<br>Glu Leu Met Tyr Ser Asp Lys Ser Met Ile Gln Val Pro Tyr Arg Leu<br>               580                       585                     590 | 2133 |
| cat gcc gtt tta gtt cac gaa ggc caa gct aat gct ggg cac tac tgg<br>His Ala Val Leu Val His Glu Gly Gln Ala Asn Ala Gly His Tyr Trp<br>595                     600                     605 | 2181 |
| gca tat att ttt gat cat cgt gaa agc aga tgg atg aag tac aat gat<br>Ala Tyr Ile Phe Asp His Arg Glu Ser Arg Trp Met Lys Tyr Asn Asp<br>610                     615                     620                 625 | 2229 |
| att gct gtg aca aaa tca tca tgg gaa gag cta gtg agg gac tct ttt<br>Ile Ala Val Thr Lys Ser Ser Trp Glu Glu Leu Val Arg Asp Ser Phe | 2277 |

```
                    -continued
           630            635            640
ggt ggt tat aga aat gcc agt gca tac tgt tta atg tac ata aat gat    2325
Gly Gly Tyr Arg Asn Ala Ser Ala Tyr Cys Leu Met Tyr Ile Asn Asp
            645            650            655 aag gca cag ttc cta ata caa gag gag ttt aat aaa gaa act ggg cag    2373
Lys Ala Gln Phe Leu Ile Gln Glu Glu Phe Asn Lys Glu Thr Gly Gln
        660            665            670 ccc ctt gtt ggt ata gaa aca tta cca ccg gat ttg aga gat ttt gtt    2421
Pro Leu Val Gly Ile Glu Thr Leu Pro Pro Asp Leu Arg Asp Phe Val
    675            680            685 gag gaa gac aac caa cga ttt gaa aaa gaa cta gaa gaa tgg gat gca    2469
Glu Glu Asp Asn Gln Arg Phe Glu Lys Glu Leu Glu Glu Trp Asp Ala
690            695            700            705 caa ctt gcc cag aaa gct ttg cag gaa aag ctt tta gcg tct cag aaa    2517
Gln Leu Ala Gln Lys Ala Leu Gln Glu Lys Leu Leu Ala Ser Gln Lys
        710            715            720 ttg aga gag tca gag act tct gtg aca aca gca caa gca gca gga gac    2565
Leu Arg Glu Ser Glu Thr Ser Val Thr Thr Ala Gln Ala Ala Gly Asp
            725            730            735 cca gaa tat cta gag cag cca tca aga agt gat ttc tca aag cac ttg    2613
Pro Glu Tyr Leu Glu Gln Pro Ser Arg Ser Asp Phe Ser Lys His Leu
        740            745            750 aaa gaa gaa act att caa ata att acc aag gca tca cat gag cat gaa    2661
Lys Glu Glu Thr Ile Gln Ile Ile Thr Lys Ala Ser His Glu His Glu
    755            760            765 gat aaa agt cct gaa aca gtt ttg cag tcg gca att aag ttg gaa tat    2709
Asp Lys Ser Pro Glu Thr Val Leu Gln Ser Ala Ile Lys Leu Glu Tyr
770            775            780            785 gca agg ttg gtt aag ttg gcc caa gaa gac acc cca cca gaa acc gat    2757
Ala Arg Leu Val Lys Leu Ala Gln Glu Asp Thr Pro Pro Glu Thr Asp
        790            795            800 tat cgt tta cat cat gta gtg gtc tac ttt atc cag aac cag gca cca    2805
Tyr Arg Leu His His Val Val Val Tyr Phe Ile Gln Asn Gln Ala Pro
            805            810            815 aag aaa att att gag aaa aca tta cta gaa caa ttt gga gat aga aat    2853
Lys Lys Ile Ile Glu Lys Thr Leu Leu Glu Gln Phe Gly Asp Arg Asn
        820            825            830 ttg agt ttt gat gaa agg tgt cac aac ata atg aaa gtt gct caa gcc    2901
Leu Ser Phe Asp Glu Arg Cys His Asn Ile Met Lys Val Ala Gln Ala
    835            840            845 aaa ctg gaa atg ata aaa cct gaa gaa gta aac ttg gag gaa tat gag    2949
Lys Leu Glu Met Ile Lys Pro Glu Glu Val Asn Leu Glu Glu Tyr Glu
850            855            860            865 gag tgg cat cag gat tat agg aaa ttc agg gaa aca act atg tat ctc    2997
Glu Trp His Gln Asp Tyr Arg Lys Phe Arg Glu Thr Thr Met Tyr Leu
        870            875            880 ata att ggg cta gaa aat ttt caa aga gaa agt tat ata gat tcc ttg    3045
Ile Ile Gly Leu Glu Asn Phe Gln Arg Glu Ser Tyr Ile Asp Ser Leu
            885            890            895 ctg ttc ctc atc tgt gct tat cag aat aac aaa gaa ctc ttg tct aaa    3093
Leu Phe Leu Ile Cys Ala Tyr Gln Asn Asn Lys Glu Leu Leu Ser Lys
        900            905            910 ggc tta tac aga gga cat gat gaa gaa ttg ata tca cat tat aga aga    3141
Gly Leu Tyr Arg Gly His Asp Glu Glu Leu Ile Ser His Tyr Arg Arg
    915            920            925 gaa tgt ttg cta aaa tta aat gag caa gcc gca gaa ctc ttc gaa tct    3189
Glu Cys Leu Leu Lys Leu Asn Glu Gln Ala Ala Glu Leu Phe Glu Ser
930            935            940            945 gga gag gat cga gaa gta aac aat ggt ttg att atc atg aat gag ttt    3237
Gly Glu Asp Arg Glu Val Asn Asn Gly Leu Ile Ile Met Asn Glu Phe
```

-continued

| | | | | | | | | | | | | |
|---|---|---|---|---|---|---|---|---|---|---|---|---|
|Gly|Glu|Asp|Arg|Glu|Val|Asn|Asn|Gly|Leu|Ile|Ile|Met|Asn|Glu|Phe|
| | | | |950| | | |955| | | |960| | | | att gtc cca ttt ttg cca tta tta ctg gtg gat gaa atg gaa gaa aag    3285
Ile Val Pro Phe Leu Pro Leu Leu Leu Val Asp Glu Met Glu Glu Lys
            965                 970                 975 gat ata cta gct gta gaa gat atg aga aat cga tgg tgt tcc tac ctt    3333
Asp Ile Leu Ala Val Glu Asp Met Arg Asn Arg Trp Cys Ser Tyr Leu
        980                 985                 990 ggt caa gaa atg gaa cca cac ctc caa gaa aag ctg aca gat ttt ttg    3381
Gly Gln Glu Met Glu Pro His Leu Gln Glu Lys Leu Thr Asp Phe Leu
    995                 1000                1005 cca aaa ctg ctt gat tgt tct atg gag att aaa agt ttc cat gag        3426
Pro Lys Leu Leu Asp Cys Ser Met Glu Ile Lys Ser Phe His Glu
1010            1015                1020 cca ccg aag tta cct tca tat tcc acg cat gaa ctc tgt gag cga        3471
Pro Pro Lys Leu Pro Ser Tyr Ser Thr His Glu Leu Cys Glu Arg
1025            1030                1035 ttt gcc cga atc atg ttg tcc ctc agt cga act cct gct gat gga        3516
Phe Ala Arg Ile Met Leu Ser Leu Ser Arg Thr Pro Ala Asp Gly
1040            1045                1050 aga taa actgcacact ttccctgaac acactgtata aactctttt agttcttaac      3572
Arg
1055 ccttgccttc ctgtcacagg gtttgcttgt tgctgctata gttttaact tttttttatt   3632 ttaataactg caaagacaa aatgactata cagactttag tcagactgca gacaataaag   3692 ctgaaaatcg catggcgctc agacatttta accggaactg atgtataatc acaaatctaa  3752 ttgattttat tatggcaaaa ctatgctttt gccaccttcc tgttgcagta ttactttgct  3812 tttatctttt ctttctcaac agctttccat tcagtctgga tccttccatg actacagcca  3872 tttaagtgtt cagcactgtg tacgatacat aatatttggt agcttgtaaa tgaaataaag  3932 aataaagttt tatttatggc tac                                         3955

<210> SEQ ID NO 2
<211> LENGTH: 1055
<212> TYPE: PRT
<213> ORGANISM: Homo sapiens
<220> FEATURE:
<221> NAME/KEY: misc_feature
<222> LOCATION: (373)..(373)
<223> OTHER INFORMATION: The 'Xaa' at location 373 stands for Glu, or
      Asp.
<220> FEATURE:
<221> NAME/KEY: misc_feature
<222> LOCATION: (1473)..(1473)
<223> OTHER INFORMATION: "n" at position 1473 can be any base.

<400> SEQUENCE: 2

Met Thr Val Glu Gln Asn Val Leu Gln Gln Ser Ala Ala Gln Lys His
1               5                   10                  15

Gln Gln Thr Phe Leu Asn Gln Leu Arg Glu Ile Thr Gly Ile Asn Asp
            20                  25                  30

Thr Gln Ile Leu Gln Gln Ala Leu Lys Asp Ser Asn Gly Asn Leu Glu
        35                  40                  45

Leu Ala Val Ala Phe Leu Thr Ala Lys Asn Ala Lys Thr Pro Gln Gln
    50                  55                  60

Glu Glu Thr Thr Tyr Tyr Gln Thr Ala Leu Pro Gly Asn Asp Arg Tyr
65                  70                  75                  80

Ile Ser Val Gly Ser Gln Ala Asp Thr Asn Val Ile Asp Leu Thr Gly
                85                  90                  95

```
Asp Asp Lys Asp Asp Leu Gln Arg Thr Ile Ala Leu Ser Leu Ala Glu
            100                 105                 110

Ser Asn Arg Ala Phe Arg Glu Thr Gly Ile Thr Asp Glu Glu Gln Ala
            115                 120                 125

Ile Ser Arg Val Leu Glu Ala Ser Ile Ala Glu Asn Lys Ala Cys Leu
            130                 135                 140

Lys Arg Thr Pro Thr Glu Val Trp Arg Asp Ser Arg Asn Pro Tyr Asp
145                 150                 155                 160

Arg Lys Arg Gln Asp Lys Ala Pro Val Gly Leu Lys Asn Val Gly Asn
                    165                 170                 175

Thr Cys Trp Phe Ser Ala Val Ile Gln Ser Leu Phe Asn Leu Leu Glu
            180                 185                 190

Phe Arg Arg Leu Val Leu Asn Tyr Lys Pro Pro Ser Asn Ala Gln Asp
            195                 200                 205

Leu Pro Arg Asn Gln Lys Glu His Arg Asn Leu Pro Phe Met Arg Glu
            210                 215                 220

Leu Arg Tyr Leu Phe Ala Leu Leu Val Gly Thr Lys Arg Lys Tyr Val
225                 230                 235                 240

Asp Pro Ser Arg Ala Val Glu Ile Leu Lys Asp Ala Phe Lys Ser Asn
                    245                 250                 255

Asp Ser Gln Gln Gln Asp Val Ser Glu Phe Thr His Lys Leu Leu Asp
            260                 265                 270

Trp Leu Glu Asp Ala Phe Gln Met Lys Ala Glu Glu Thr Asp Glu
            275                 280                 285

Glu Lys Pro Lys Asn Pro Met Val Glu Leu Phe Tyr Gly Arg Phe Leu
    290                 295                 300

Ala Val Gly Val Leu Glu Gly Lys Lys Phe Glu Asn Thr Glu Met Phe
305                 310                 315                 320

Gly Gln Tyr Pro Leu Gln Val Asn Gly Phe Lys Asp Leu His Glu Cys
            325                 330                 335

Leu Glu Ala Ala Met Ile Glu Gly Glu Ile Glu Ser Leu His Ser Glu
            340                 345                 350

Asn Ser Gly Lys Ser Gly Gln Glu His Trp Phe Thr Gly Leu Pro Pro
            355                 360                 365

Val Leu Thr Phe Xaa Leu Ser Arg Phe Glu Phe Asn Gln Ala Leu Gly
            370                 375                 380

Arg Pro Glu Lys Ile His Asn Lys Leu Glu Phe Pro Gln Val Leu Tyr
385                 390                 395                 400

Leu Asp Arg Tyr Met His Arg Asn Arg Glu Ile Thr Arg Ile Lys Arg
                    405                 410                 415

Glu Glu Ile Lys Arg Leu Lys Asp Tyr Leu Thr Val Leu Gln Gln Arg
            420                 425                 430

Leu Glu Arg Tyr Leu Ser Tyr Gly Ser Gly Pro Lys Arg Phe Pro Leu
            435                 440                 445

Val Asp Val Leu Gln Tyr Ala Leu Glu Phe Ala Ser Ser Lys Pro Val
450                 455                 460

Cys Thr Ser Pro Val Asp Asp Ile Asp Ala Ser Ser Pro Ser Gly
465                 470                 475                 480

Ser Ile Pro Ser Gln Thr Leu Pro Ser Thr Thr Glu Gln Gln Gly Ala
            485                 490                 495

Leu Ser Ser Glu Leu Pro Ser Thr Ser Pro Ser Ser Val Ala Ala Ile
            500                 505                 510
```

-continued

```
Ser Ser Arg Ser Val Ile His Lys Pro Phe Thr Gln Ser Arg Ile Pro
        515                 520                 525
Pro Asp Leu Pro Met His Pro Ala Pro Arg His Ile Thr Glu Glu Glu
    530                 535                 540
Leu Ser Val Leu Glu Ser Cys Leu His Arg Trp Arg Thr Glu Ile Glu
545                 550                 555                 560
Asn Asp Thr Arg Asp Leu Gln Glu Ser Ile Ser Arg Ile His Arg Thr
                565                 570                 575
Ile Glu Leu Met Tyr Ser Asp Lys Ser Met Ile Gln Val Pro Tyr Arg
                580                 585                 590
Leu His Ala Val Leu Val His Glu Gly Gln Ala Asn Ala Gly His Tyr
            595                 600                 605
Trp Ala Tyr Ile Phe Asp His Arg Glu Ser Arg Trp Met Lys Tyr Asn
        610                 615                 620
Asp Ile Ala Val Thr Lys Ser Ser Trp Glu Glu Leu Val Arg Asp Ser
625                 630                 635                 640
Phe Gly Gly Tyr Arg Asn Ala Ser Ala Tyr Cys Leu Met Tyr Ile Asn
                645                 650                 655
Asp Lys Ala Gln Phe Leu Ile Gln Glu Glu Phe Asn Lys Glu Thr Gly
                660                 665                 670
Gln Pro Leu Val Gly Ile Glu Thr Leu Pro Pro Asp Leu Arg Asp Phe
            675                 680                 685
Val Glu Glu Asp Asn Gln Arg Phe Glu Lys Glu Leu Glu Glu Trp Asp
        690                 695                 700
Ala Gln Leu Ala Gln Lys Ala Leu Gln Glu Lys Leu Leu Ala Ser Gln
705                 710                 715                 720
Lys Leu Arg Glu Ser Glu Thr Ser Val Thr Thr Ala Gln Ala Ala Gly
                725                 730                 735
Asp Pro Glu Tyr Leu Glu Gln Pro Ser Arg Ser Asp Phe Ser Lys His
                740                 745                 750
Leu Lys Glu Glu Thr Ile Gln Ile Ile Thr Lys Ala Ser His Glu His
            755                 760                 765
Glu Asp Lys Ser Pro Glu Thr Val Leu Gln Ser Ala Ile Lys Leu Glu
        770                 775                 780
Tyr Ala Arg Leu Val Lys Leu Ala Gln Glu Asp Thr Pro Pro Glu Thr
785                 790                 795                 800
Asp Tyr Arg Leu His His Val Val Tyr Phe Ile Gln Asn Gln Ala
                805                 810                 815
Pro Lys Lys Ile Ile Glu Lys Thr Leu Leu Glu Gln Phe Gly Asp Arg
                820                 825                 830
Asn Leu Ser Phe Asp Glu Arg Cys His Asn Ile Met Lys Val Ala Gln
            835                 840                 845
Ala Lys Leu Glu Met Ile Lys Pro Glu Glu Val Asn Leu Glu Glu Tyr
        850                 855                 860
Glu Glu Trp His Gln Asp Tyr Arg Lys Phe Arg Glu Thr Thr Met Tyr
865                 870                 875                 880
Leu Ile Ile Gly Leu Glu Asn Phe Gln Arg Glu Ser Tyr Ile Asp Ser
                885                 890                 895
Leu Leu Phe Leu Ile Cys Ala Tyr Gln Asn Asn Lys Glu Leu Leu Ser
            900                 905                 910
Lys Gly Leu Tyr Arg Gly His Asp Glu Glu Leu Ile Ser His Tyr Arg
        915                 920                 925
Arg Glu Cys Leu Leu Lys Leu Asn Glu Gln Ala Ala Glu Leu Phe Glu
```

```
                    930              935             940
Ser Gly Glu Asp Arg Glu Val Asn Asn Gly Leu Ile Ile Met Asn Glu
945                 950             955                 960

Phe Ile Val Pro Phe Leu Pro Leu Leu Val Asp Glu Met Glu Glu
                965             970                 975

Lys Asp Ile Leu Ala Val Glu Asp Met Arg Asn Arg Trp Cys Ser Tyr
            980             985             990

Leu Gly Gln Glu Met Glu Pro His Leu Gln Glu Lys Leu Thr Asp Phe
            995             1000            1005

Leu Pro Lys Leu Leu Asp Cys Ser Met Glu Ile Lys Ser Phe His
    1010            1015            1020

Glu Pro Pro Lys Leu Pro Ser Tyr Ser Thr His Glu Leu Cys Glu
    1025            1030            1035

Arg Phe Ala Arg Ile Met Leu Ser Leu Ser Arg Thr Pro Ala Asp
    1040            1045            1050

Gly Arg
    1055

<210> SEQ ID NO 3
<211> LENGTH: 4015
<212> TYPE: DNA
<213> ORGANISM: Homo sapiens
<220> FEATURE:
<221> NAME/KEY: misc_feature
<222> LOCATION: (1473)..(1473)
<223> OTHER INFORMATION: "n" at position 1473 can be any base.
<220> FEATURE:
<221> NAME/KEY: CDS
<222> LOCATION: (355)..(3582)
<223> OTHER INFORMATION:

<400> SEQUENCE: 3
cggcagcaaa ggaacgtgcg aacgcgtgac gccgcccgac tggctcgcgc tctcccgtgc     60
cccggcgtcc tccgcccgct catggcccgg gccgccgcgg acgagcggcg ctgaggcggg    120
ccgcgtggag acgtgaggcg gccgccgtgg ccctcacagt cggcgttttcg ccgcctgccc   180 gcggtgcccg cgcacgcctg ccgccatcgc cttcgcgcct ggctggcggg ggcgctgtcc    240
tcccaggccg tccgcgccgc tccctggagc tcggcggagc gcggcagcca gggccggcgg    300
aggcgcgagg agccgggcgc caccgccgcc gccgccgccc cgccgcgggg ggcc atg      357
                                                              Met
                                                              1 acc gtg gag cag aac gtg ctg cag cag agc gcg gcg cag aag cac cag      405
Thr Val Glu Gln Asn Val Leu Gln Gln Ser Ala Ala Gln Lys His Gln
        5                   10                  15 cag acg ttt ttg aat caa ctg aga gaa att acg ggg att aat gac acc      453
Gln Thr Phe Leu Asn Gln Leu Arg Glu Ile Thr Gly Ile Asn Asp Thr
    20                  25                  30 cag ata cta cag caa gcc ttg aag gat agt aat gga aac ttg gaa tta      501
Gln Ile Leu Gln Gln Ala Leu Lys Asp Ser Asn Gly Asn Leu Glu Leu
35                  40                  45 gca gtg gct ttc ctt act gcg aag aat gct aag acc cct cag cag gag      549
Ala Val Ala Phe Leu Thr Ala Lys Asn Ala Lys Thr Pro Gln Gln Glu
50                  55                  60                  65 gag aca act tac tac caa aca gca ctt cct ggc aat gat aga tac atc      597
Glu Thr Thr Tyr Tyr Gln Thr Ala Leu Pro Gly Asn Asp Arg Tyr Ile
                70                  75                  80 agt gtg gga agc caa gca gat aca aat gtg att gat ctc act gga gat      645
Ser Val Gly Ser Gln Ala Asp Thr Asn Val Ile Asp Leu Thr Gly Asp
            85                  90                  95
```

-continued

| | |
|---|---|
| gat aaa gat gat ctt cag aga aca att gcc ttg agt ttg gcc gaa tca<br>Asp Lys Asp Asp Leu Gln Arg Thr Ile Ala Leu Ser Leu Ala Glu Ser<br>           100                    105                    110 | 693 |
| aac agg gca ttc agg gag act gga ata act gat gag gaa caa gcc att<br>Asn Arg Ala Phe Arg Glu Thr Gly Ile Thr Asp Glu Glu Gln Ala Ile<br>115                    120                    125 | 741 |
| agc aga gtt ctt gaa gcc agt ata gca gag aat aaa gca tgt ttg aag<br>Ser Arg Val Leu Glu Ala Ser Ile Ala Glu Asn Lys Ala Cys Leu Lys<br>130                    135                    140                    145 | 789 |
| agg aca cct aca gaa gtt tgg agg gat tct cga aac cct tat gat aga<br>Arg Thr Pro Thr Glu Val Trp Arg Asp Ser Arg Asn Pro Tyr Asp Arg<br>                    150                    155                    160 | 837 |
| aaa aga cag gac aaa gct ccc gtt ggg cta aag aat gtt ggc aat act<br>Lys Arg Gln Asp Lys Ala Pro Val Gly Leu Lys Asn Val Gly Asn Thr<br>            165                    170                    175 | 885 |
| tgt tgg ttt agt gct gtt att cag tca tta ttt aat ctt ttg gaa ttt<br>Cys Trp Phe Ser Ala Val Ile Gln Ser Leu Phe Asn Leu Leu Glu Phe<br>                    180                    185                    190 | 933 |
| aga aga tta gtt ctg aat tac aag cct cca tca aat gct caa gat tta<br>Arg Arg Leu Val Leu Asn Tyr Lys Pro Pro Ser Asn Ala Gln Asp Leu<br>195                    200                    205 | 981 |
| ccc cga aac caa aag gaa cat cgg aat ttg cct ttt atg cgt gag ctg<br>Pro Arg Asn Gln Lys Glu His Arg Asn Leu Pro Phe Met Arg Glu Leu<br>210                    215                    220                    225 | 1029 |
| agg tat cta ttt gca ctt ctt gtt ggt acc aaa agg aag tat gtt gat<br>Arg Tyr Leu Phe Ala Leu Leu Val Gly Thr Lys Arg Lys Tyr Val Asp<br>                    230                    235                    240 | 1077 |
| cca tca aga gca gtt gaa att ctt aag gat gct ttc aaa tca aat gac<br>Pro Ser Arg Ala Val Glu Ile Leu Lys Asp Ala Phe Lys Ser Asn Asp<br>245                    250                    255 | 1125 |
| tca cag cag caa gat gtg agt gag ttt aca cac aaa tta tta gat tgg<br>Ser Gln Gln Gln Asp Val Ser Glu Phe Thr His Lys Leu Leu Asp Trp<br>            260                    265                    270 | 1173 |
| tta gaa gat gcc ttc caa atg aaa gct gaa gag gag acg gat gaa gag<br>Leu Glu Asp Ala Phe Gln Met Lys Ala Glu Glu Glu Thr Asp Glu Glu<br>            275                    280                    285 | 1221 |
| aag cca aag aac ccc atg gta gag ttg ttc tat ggc aga ttc ctg gct<br>Lys Pro Lys Asn Pro Met Val Glu Leu Phe Tyr Gly Arg Phe Leu Ala<br>290                    295                    300                    305 | 1269 |
| gtg gga gta ctt gaa ggt aaa aaa ttt gaa aac act gaa atg ttt ggt<br>Val Gly Val Leu Glu Gly Lys Lys Phe Glu Asn Thr Glu Met Phe Gly<br>                    310                    315                    320 | 1317 |
| cag tac cca ctt cag gtc aat ggg ttc aaa gat ctg cat gag tgc cta<br>Gln Tyr Pro Leu Gln Val Asn Gly Phe Lys Asp Leu His Glu Cys Leu<br>                    325                    330                    335 | 1365 |
| gaa gct gca atg att gaa gga gaa att gag tct tta cat tca gag aat<br>Glu Ala Ala Met Ile Glu Gly Glu Ile Glu Ser Leu His Ser Glu Asn<br>            340                    345                    350 | 1413 |
| tca gga aaa tca ggc caa gag cat tgg ttt act gga tta cca cct gtg<br>Ser Gly Lys Ser Gly Gln Glu His Trp Phe Thr Gly Leu Pro Pro Val<br>355                    360                    365 | 1461 |
| tta aca ttt gan ttg tca aga ttt gaa ttt aat cag gca ttg gga aga<br>Leu Thr Phe Xaa Leu Ser Arg Phe Glu Phe Asn Gln Ala Leu Gly Arg<br>370                    375                    380                    385 | 1509 |
| cca gaa aaa att cac aac aaa tta gaa ttt ccc caa gtt tta tat ttg<br>Pro Glu Lys Ile His Asn Lys Leu Glu Phe Pro Gln Val Leu Tyr Leu<br>                    390                    395                    400 | 1557 |
| gac aga tac atg cac aga aac aga gaa ata aca aga att aag agg gaa<br>Asp Arg Tyr Met His Arg Asn Arg Glu Ile Thr Arg Ile Lys Arg Glu | 1605 |

```
                    405                 410                 415
gag atc aag aga ctg aaa gat tac ctc acg gta tta caa caa agg cta      1653
Glu Ile Lys Arg Leu Lys Asp Tyr Leu Thr Val Leu Gln Gln Arg Leu
            420                 425                 430 gaa aga tat tta agc tat ggt tcc ggt ccc aaa cga ttc ccc ttg gta      1701
Glu Arg Tyr Leu Ser Tyr Gly Ser Gly Pro Lys Arg Phe Pro Leu Val
        435                 440                 445 gat gtt ctt cag tat gca ttg gaa ttt gcc tca agt aaa cct gtt tgc      1749
Asp Val Leu Gln Tyr Ala Leu Glu Phe Ala Ser Ser Lys Pro Val Cys
450                 455                 460                 465 act tct cct gtt gac gat att gac gct agt tcc cca cct agt ggt tcc      1797
Thr Ser Pro Val Asp Asp Ile Asp Ala Ser Ser Pro Pro Ser Gly Ser
                470                 475                 480 ata cca tca cag aca tta cca agc aca aca gaa caa cag gga gcc cta      1845
Ile Pro Ser Gln Thr Leu Pro Ser Thr Thr Glu Gln Gln Gly Ala Leu
            485                 490                 495 tct tca gaa ctg cca agc aca tca cct tca tca gtt gct gcc att tca      1893
Ser Ser Glu Leu Pro Ser Thr Ser Pro Ser Ser Val Ala Ala Ile Ser
        500                 505                 510 tcg aga tca gta ata cac aaa cca ttt act cag tcc cgg ata cct cca      1941
Ser Arg Ser Val Ile His Lys Pro Phe Thr Gln Ser Arg Ile Pro Pro
515                 520                 525 gat ttg ccc atg cat ccg gca cca agg cac ata acg gag gaa gaa ctt      1989
Asp Leu Pro Met His Pro Ala Pro Arg His Ile Thr Glu Glu Glu Leu
530                 535                 540                 545 tct gtg ctg gaa agt tgt tta cat cgc tgg agg aca gaa ata gaa aat      2037
Ser Val Leu Glu Ser Cys Leu His Arg Trp Arg Thr Glu Ile Glu Asn
                550                 555                 560 gac acc aga gat ttg cag gaa agc ata tcc aga atc cat cga aca att      2085
Asp Thr Arg Asp Leu Gln Glu Ser Ile Ser Arg Ile His Arg Thr Ile
            565                 570                 575 gaa tta atg tac tct gac aaa tct atg ata caa gtt cct tat cga tta      2133
Glu Leu Met Tyr Ser Asp Lys Ser Met Ile Gln Val Pro Tyr Arg Leu
        580                 585                 590 cat gcc gtt tta gtt cac gaa ggc caa gct aat gct ggg cac tac tgg      2181
His Ala Val Leu Val His Glu Gly Gln Ala Asn Ala Gly His Tyr Trp
595                 600                 605 gca tat att ttt gat cat cgt gaa agc aga tgg atg aag tac aat gat      2229
Ala Tyr Ile Phe Asp His Arg Glu Ser Arg Trp Met Lys Tyr Asn Asp
610                 615                 620                 625 att gct gtg aca aaa tca tca tgg gaa gag cta gtg agg gac tct ttt      2277
Ile Ala Val Thr Lys Ser Ser Trp Glu Glu Leu Val Arg Asp Ser Phe
                630                 635                 640 ggt ggt tat aga aat gcc agt gca tac tgt tta atg tac ata aat gat      2325
Gly Gly Tyr Arg Asn Ala Ser Ala Tyr Cys Leu Met Tyr Ile Asn Asp
            645                 650                 655 aag gca cag ttc cta ata caa gag gag ttt aat aaa gaa act ggg cag      2373
Lys Ala Gln Phe Leu Ile Gln Glu Glu Phe Asn Lys Glu Thr Gly Gln
        660                 665                 670 ccc ctt gtt ggt ata gaa aca tta cca ccg gat ttg aga gat ttt gtt      2421
Pro Leu Val Gly Ile Glu Thr Leu Pro Pro Asp Leu Arg Asp Phe Val
675                 680                 685 gag gaa gac aac caa cga ttt gaa aaa gaa cta gaa gaa tgg gat gca      2469
Glu Glu Asp Asn Gln Arg Phe Glu Lys Glu Leu Glu Glu Trp Asp Ala
690                 695                 700                 705 caa ctt gcc cag aaa gct ttg cag gaa aag ctt tta gcg tct cag aaa      2517
Gln Leu Ala Gln Lys Ala Leu Gln Glu Lys Leu Leu Ala Ser Gln Lys
                710                 715                 720 ttg aga gag tca gag act tct gtg aca aca gca caa gca gca gga gac      2565
```

```
Leu Arg Glu Ser Glu Thr Ser Val Thr Thr Ala Gln Ala Ala Gly Asp
            725                 730                 735 cca gaa tat cta gag cag cca tca aga agt gat ttc tca aag cac ttg      2613
Pro Glu Tyr Leu Glu Gln Pro Ser Arg Ser Asp Phe Ser Lys His Leu
        740                 745                 750 aaa gaa gaa act att caa ata att acc aag gca tca cat gag cat gaa      2661
Lys Glu Glu Thr Ile Gln Ile Ile Thr Lys Ala Ser His Glu His Glu
    755                 760                 765 gat aaa agt cct gaa aca gtt ttg cag tcg gca att aag ttg gaa tat      2709
Asp Lys Ser Pro Glu Thr Val Leu Gln Ser Ala Ile Lys Leu Glu Tyr
770                 775                 780                 785 gca agg ttg gtt aag ttg gcc caa gaa gac acc cca cca gaa acc gat      2757
Ala Arg Leu Val Lys Leu Ala Gln Glu Asp Thr Pro Pro Glu Thr Asp
            790                 795                 800 tat cgt tta cat cat gta gtg gtc tac ttt atc cag aac cag gca cca      2805
Tyr Arg Leu His His Val Val Val Tyr Phe Ile Gln Asn Gln Ala Pro
        805                 810                 815 aag aaa att att gag aaa aca tta cta gaa caa ttt gga gat aga aat      2853
Lys Lys Ile Ile Glu Lys Thr Leu Leu Glu Gln Phe Gly Asp Arg Asn
    820                 825                 830 ttg agt ttt gat gaa agg tgt cac aac ata atg aaa gtt gct caa gcc      2901
Leu Ser Phe Asp Glu Arg Cys His Asn Ile Met Lys Val Ala Gln Ala
835                 840                 845 aaa ctg gaa atg ata aaa cct gaa gaa gta aac ttg gag gaa tat gag      2949
Lys Leu Glu Met Ile Lys Pro Glu Glu Val Asn Leu Glu Glu Tyr Glu
850                 855                 860                 865 gag tgg cat cag gat tat agg aaa ttc agg gaa aca act atg tat ctc      2997
Glu Trp His Gln Asp Tyr Arg Lys Phe Arg Glu Thr Thr Met Tyr Leu
            870                 875                 880 ata att ggg cta gaa aat ttt caa aga gaa agt tat ata gat tcc ttg      3045
Ile Ile Gly Leu Glu Asn Phe Gln Arg Glu Ser Tyr Ile Asp Ser Leu
        885                 890                 895 ctg ttc ctc atc tgt gct tat cag aat aac aaa gaa ctc ttg tct aaa      3093
Leu Phe Leu Ile Cys Ala Tyr Gln Asn Asn Lys Glu Leu Leu Ser Lys
    900                 905                 910 ggc tta tac aga gga cat gat gaa gaa ttg ata tca cat tat aga aga      3141
Gly Leu Tyr Arg Gly His Asp Glu Glu Leu Ile Ser His Tyr Arg Arg
915                 920                 925 gaa tgt ttg cta atc ctt aat tta aaa agg aaa caa aaa cct att ctt      3189
Glu Cys Leu Leu Ile Leu Asn Leu Lys Arg Lys Gln Lys Pro Ile Leu
930                 935                 940                 945 ttt ttt ttc ctg cat tgc att aag aaa tta aat gag caa gcc gca gaa      3237
Phe Phe Phe Leu His Cys Ile Lys Lys Leu Asn Glu Gln Ala Ala Glu
            950                 955                 960 ctc ttc gaa tct gga gag gat cga gaa gta aac aat ggt ttg att atc      3285
Leu Phe Glu Ser Gly Glu Asp Arg Glu Val Asn Asn Gly Leu Ile Ile
        965                 970                 975 atg aat gag ttt att gtc cca ttt ttg cca tta tta ctg gtg gat gaa      3333
Met Asn Glu Phe Ile Val Pro Phe Leu Pro Leu Leu Leu Val Asp Glu
    980                 985                 990 atg gaa gaa aag gat ata cta gct gta gaa gat atg aga aat cga tgg      3381
Met Glu Glu Lys Asp Ile Leu Ala Val Glu Asp Met Arg Asn Arg Trp
995                 1000                1005 tgt tcc tac ctt ggt caa gaa atg gaa cca cac ctc caa gaa aag         3426
Cys Ser Tyr Leu Gly Gln Glu Met Glu Pro His Leu Gln Glu Lys
1010                1015                1020 ctg aca gat ttt ttg cca aaa ctg ctt gat tgt tct atg gag att         3471
Leu Thr Asp Phe Leu Pro Lys Leu Leu Asp Cys Ser Met Glu Ile
1025                1030                1035
```

```
aaa agt ttc cat gag cca ccg aag tta cct tca tat tcc acg cat    3516
Lys Ser Phe His Glu Pro Pro Lys Leu Pro Ser Tyr Ser Thr His
1040                1045                1050 gaa ctc tgt gag cga ttt gcc cga atc atg ttg tcc ctc agt cga    3561
Glu Leu Cys Glu Arg Phe Ala Arg Ile Met Leu Ser Leu Ser Arg
1055                1060                1065 act cct gct gat gga aga taa actgcacact ttccctgaac acactgtata   3612
Thr Pro Ala Asp Gly Arg
1070            1075 aactctttt agttcttaac ccttgccttc ctgtcacagg gtttgcttgt tgctgctata    3672 gttttaact tttttttatt ttaataactg caaaagacaa aatgactata cagactttag    3732
tcagactgca gacaataaag ctgaaaatcg catggcgctc agacatttta accggaactg    3792
atgtataatc acaaatctaa ttgattttat tatggcaaaa ctatgctttt gccaccttcc    3852
tgttgcagta ttactttgct tttatctttt ctttctcaac agctttccat tcagtctgga    3912
tccttccatg actacagcca tttaagtgtt cagcactgtg tacgatacat aatatttggt    3972
agcttgtaaa tgaaataaag aataaagttt tatttatggc tac    4015
```

<210> SEQ ID NO 4
<211> LENGTH: 1075
<212> TYPE: PRT
<213> ORGANISM: Homo sapiens
<220> FEATURE:
<221> NAME/KEY: misc_feature
<222> LOCATION: (373)..(373)
<223> OTHER INFORMATION: The 'Xaa' at location 373 stands for Glu, or
      Asp.
<220> FEATURE:
<221> NAME/KEY: misc_feature
<222> LOCATION: (1473)..(1473)
<223> OTHER INFORMATION: "n" at position 1473 can be any base.

<400> SEQUENCE: 4

```
Met Thr Val Glu Gln Asn Val Leu Gln Gln Ser Ala Ala Gln Lys His
1               5                   10                  15

Gln Gln Thr Phe Leu Asn Gln Leu Arg Glu Ile Thr Gly Ile Asn Asp
            20                  25                  30

Thr Gln Ile Leu Gln Gln Ala Leu Lys Asp Ser Asn Gly Asn Leu Glu
        35                  40                  45

Leu Ala Val Ala Phe Leu Thr Ala Lys Asn Ala Lys Thr Pro Gln Gln
    50                  55                  60

Glu Glu Thr Thr Tyr Tyr Gln Thr Ala Leu Pro Gly Asn Asp Arg Tyr
65                  70                  75                  80

Ile Ser Val Gly Ser Gln Ala Asp Thr Asn Val Ile Asp Leu Thr Gly
                85                  90                  95

Asp Asp Lys Asp Asp Leu Gln Arg Thr Ile Ala Leu Ser Leu Ala Glu
            100                 105                 110

Ser Asn Arg Ala Phe Arg Glu Thr Gly Ile Thr Asp Glu Glu Gln Ala
        115                 120                 125

Ile Ser Arg Val Leu Glu Ala Ser Ile Ala Glu Asn Lys Ala Cys Leu
    130                 135                 140

Lys Arg Thr Pro Thr Glu Val Trp Arg Asp Ser Arg Asn Pro Tyr Asp
145                 150                 155                 160

Arg Lys Arg Gln Asp Lys Ala Pro Val Gly Leu Lys Asn Val Gly Asn
                165                 170                 175

Thr Cys Trp Phe Ser Ala Val Ile Gln Ser Leu Phe Asn Leu Leu Glu
            180                 185                 190
```

-continued

```
Phe Arg Arg Leu Val Leu Asn Tyr Lys Pro Pro Ser Asn Ala Gln Asp
        195                 200                 205

Leu Pro Arg Asn Gln Lys Glu His Arg Asn Leu Pro Phe Met Arg Glu
    210                 215                 220

Leu Arg Tyr Leu Phe Ala Leu Leu Val Gly Thr Lys Arg Lys Tyr Val
225                 230                 235                 240

Asp Pro Ser Arg Ala Val Glu Ile Leu Lys Asp Ala Phe Lys Ser Asn
                245                 250                 255

Asp Ser Gln Gln Gln Asp Val Ser Glu Phe Thr His Lys Leu Leu Asp
            260                 265                 270

Trp Leu Glu Asp Ala Phe Gln Met Lys Ala Glu Glu Thr Asp Glu
        275                 280                 285

Glu Lys Pro Lys Asn Pro Met Val Glu Leu Phe Tyr Gly Arg Phe Leu
    290                 295                 300

Ala Val Gly Val Leu Glu Gly Lys Lys Phe Glu Asn Thr Glu Met Phe
305                 310                 315                 320

Gly Gln Tyr Pro Leu Gln Val Asn Gly Phe Lys Asp Leu His Glu Cys
                325                 330                 335

Leu Glu Ala Ala Met Ile Glu Gly Ile Glu Ser Leu His Ser Glu
            340                 345                 350

Asn Ser Gly Lys Ser Gly Gln Glu His Trp Phe Thr Gly Leu Pro Pro
        355                 360                 365

Val Leu Thr Phe Xaa Leu Ser Arg Phe Glu Phe Asn Gln Ala Leu Gly
    370                 375                 380

Arg Pro Glu Lys Ile His Asn Lys Leu Glu Phe Pro Gln Val Leu Tyr
385                 390                 395                 400

Leu Asp Arg Tyr Met His Arg Asn Arg Glu Ile Thr Arg Ile Lys Arg
                405                 410                 415

Glu Glu Ile Lys Arg Leu Lys Asp Tyr Leu Thr Val Leu Gln Gln Arg
            420                 425                 430

Leu Glu Arg Tyr Leu Ser Tyr Gly Ser Gly Pro Lys Arg Phe Pro Leu
        435                 440                 445

Val Asp Val Leu Gln Tyr Ala Leu Glu Phe Ala Ser Ser Lys Pro Val
    450                 455                 460

Cys Thr Ser Pro Val Asp Asp Ile Asp Ala Ser Ser Pro Ser Gly
465                 470                 475                 480

Ser Ile Pro Ser Gln Thr Leu Pro Ser Thr Thr Glu Gln Gly Ala
                485                 490                 495

Leu Ser Ser Glu Leu Pro Ser Thr Ser Pro Ser Ser Val Ala Ala Ile
            500                 505                 510

Ser Ser Arg Ser Val Ile His Lys Pro Phe Thr Gln Ser Arg Ile Pro
        515                 520                 525

Pro Asp Leu Pro Met His Pro Ala Pro Arg His Ile Thr Glu Glu Glu
    530                 535                 540

Leu Ser Val Leu Glu Ser Cys Leu His Arg Trp Arg Thr Glu Ile Glu
545                 550                 555                 560

Asn Asp Thr Arg Asp Leu Gln Glu Ser Ile Ser Arg Ile His Arg Thr
                565                 570                 575

Ile Glu Leu Met Tyr Ser Asp Lys Ser Met Ile Gln Val Pro Tyr Arg
            580                 585                 590

Leu His Ala Val Leu Val His Glu Gly Gln Ala Asn Ala Gly His Tyr
        595                 600                 605

Trp Ala Tyr Ile Phe Asp His Arg Glu Ser Arg Trp Met Lys Tyr Asn
```

-continued

```
              610                 615                 620
Asp Ile Ala Val Thr Lys Ser Ser Trp Glu Glu Leu Val Arg Asp Ser
625                 630                 635                 640

Phe Gly Gly Tyr Arg Asn Ala Ser Ala Tyr Cys Leu Met Tyr Ile Asn
                645                 650                 655

Asp Lys Ala Gln Phe Leu Ile Gln Glu Glu Phe Asn Lys Glu Thr Gly
            660                 665                 670

Gln Pro Leu Val Gly Ile Glu Thr Leu Pro Pro Asp Leu Arg Asp Phe
        675                 680                 685

Val Glu Glu Asp Asn Gln Arg Phe Glu Lys Glu Leu Glu Glu Trp Asp
690                 695                 700

Ala Gln Leu Ala Gln Lys Ala Leu Gln Glu Lys Leu Leu Ala Ser Gln
705                 710                 715                 720

Lys Leu Arg Glu Ser Glu Thr Ser Val Thr Thr Ala Gln Ala Ala Gly
                725                 730                 735

Asp Pro Glu Tyr Leu Glu Gln Pro Ser Arg Ser Asp Phe Ser Lys His
            740                 745                 750

Leu Lys Glu Glu Thr Ile Gln Ile Ile Thr Lys Ala Ser His Glu His
        755                 760                 765

Glu Asp Lys Ser Pro Glu Thr Val Leu Gln Ser Ala Ile Lys Leu Glu
770                 775                 780

Tyr Ala Arg Leu Val Lys Leu Ala Gln Glu Asp Thr Pro Glu Thr
785                 790                 795                 800

Asp Tyr Arg Leu His His Val Val Tyr Phe Ile Gln Asn Gln Ala
                805                 810                 815

Pro Lys Lys Ile Ile Glu Lys Thr Leu Leu Glu Gln Phe Gly Asp Arg
            820                 825                 830

Asn Leu Ser Phe Asp Glu Arg Cys His Asn Ile Met Lys Val Ala Gln
        835                 840                 845

Ala Lys Leu Glu Met Ile Lys Pro Glu Glu Val Asn Leu Glu Glu Tyr
850                 855                 860

Glu Glu Trp His Gln Asp Tyr Arg Lys Phe Arg Glu Thr Thr Met Tyr
865                 870                 875                 880

Leu Ile Ile Gly Leu Glu Asn Phe Gln Arg Glu Ser Tyr Ile Asp Ser
                885                 890                 895

Leu Leu Phe Leu Ile Cys Ala Tyr Gln Asn Asn Lys Glu Leu Leu Ser
            900                 905                 910

Lys Gly Leu Tyr Arg Gly His Asp Glu Glu Leu Ile Ser His Tyr Arg
        915                 920                 925

Arg Glu Cys Leu Leu Ile Leu Asn Leu Lys Arg Lys Gln Lys Pro Ile
930                 935                 940

Leu Phe Phe Phe Leu His Cys Ile Lys Lys Leu Asn Glu Gln Ala Ala
945                 950                 955                 960

Glu Leu Phe Glu Ser Gly Glu Asp Arg Glu Val Asn Asn Gly Leu Ile
                965                 970                 975

Ile Met Asn Glu Phe Ile Val Pro Phe Leu Pro Leu Leu Leu Val Asp
            980                 985                 990

Glu Met Glu Glu Lys Asp Ile Leu  Ala Val Glu Asp Met  Arg Asn Arg
        995                 1000                1005

Trp Cys  Ser Tyr Leu Gly Gln  Glu Met Glu Pro His  Leu Gln Glu
        1010                1015                1020

Lys Leu  Thr Asp Phe Leu Pro  Lys Leu Leu Asp Cys  Ser Met Glu
        1025                1030                1035
```

-continued

Ile Lys Ser Phe His Glu Pro Pro Lys Leu Pro Ser Tyr Ser Thr
    1040                1045                1050

His Glu Leu Cys Glu Arg Phe Ala Arg Ile Met Leu Ser Leu Ser
    1055                1060                1065

Arg Thr Pro Ala Asp Gly Arg
    1070            1075

<210> SEQ ID NO 5
<211> LENGTH: 1075
<212> TYPE: PRT
<213> ORGANISM: Homo sapiens

<400> SEQUENCE: 5

Met Thr Val Glu Gln Asn Val Leu Gln Gln Ser Ala Ala Gln Lys His
1               5                   10                  15

Gln Gln Thr Phe Leu Asn Gln Leu Arg Glu Ile Thr Gly Ile Asn Asp
            20                  25                  30

Thr Gln Ile Leu Gln Gln Ala Leu Lys Asp Ser Asn Gly Asn Leu Glu
        35                  40                  45

Leu Ala Val Ala Phe Leu Thr Ala Lys Asn Ala Lys Thr Pro Gln Gln
    50                  55                  60

Glu Glu Thr Thr Tyr Tyr Gln Thr Ala Leu Pro Gly Asn Asp Arg Tyr
65                  70                  75                  80

Ile Ser Val Gly Ser Gln Ala Asp Thr Asn Val Ile Asp Leu Thr Gly
                85                  90                  95

Asp Asp Lys Asp Leu Gln Arg Ala Ile Ala Leu Ser Leu Ala Glu
            100                 105                 110

Ser Asn Arg Ala Phe Arg Glu Thr Gly Ile Thr Asp Glu Glu Gln Ala
        115                 120                 125

Ile Ser Arg Val Leu Glu Ala Ser Ile Ala Glu Asn Lys Ala Cys Leu
    130                 135                 140

Lys Arg Thr Pro Thr Glu Val Trp Arg Asp Ser Arg Asn Pro Tyr Asp
145                 150                 155                 160

Arg Lys Arg Gln Asp Lys Ala Pro Val Gly Leu Lys Asn Val Gly Asn
                165                 170                 175

Thr Cys Trp Phe Ser Ala Val Ile Gln Ser Leu Phe Asn Leu Leu Glu
        180                 185                 190

Phe Arg Arg Leu Val Leu Asn Tyr Lys Pro Pro Ser Asn Ala Gln Asp
    195                 200                 205

Leu Pro Arg Asn Gln Lys Glu His Arg Asn Leu Pro Phe Met Arg Glu
210                 215                 220

Leu Arg Tyr Leu Phe Ala Leu Leu Val Gly Thr Lys Arg Lys Tyr Val
225                 230                 235                 240

Asp Pro Ser Arg Ala Val Glu Ile Leu Lys Asp Ala Phe Lys Ser Asn
                245                 250                 255

Asp Ser Gln Gln Gln Asp Val Ser Glu Phe Thr His Lys Leu Leu Asp
        260                 265                 270

Trp Leu Glu Asp Ala Phe Gln Met Lys Ala Glu Glu Thr Asp Glu
    275                 280                 285

Glu Lys Pro Lys Asn Pro Met Val Glu Leu Phe Tyr Gly Arg Phe Leu
290                 295                 300

Ala Val Gly Val Leu Glu Gly Lys Lys Phe Glu Asn Thr Glu Met Phe
305                 310                 315                 320

Gly Gln Tyr Pro Leu Gln Val Asn Gly Phe Lys Asp Leu His Glu Cys

-continued

```
            325                 330                 335
Leu Glu Ala Ala Met Ile Glu Gly Ile Glu Ser Leu His Ser Glu
            340                 345                 350
Asn Ser Gly Lys Ser Gly Gln Glu His Trp Phe Thr Glu Leu Pro Pro
            355                 360                 365
Val Leu Thr Phe Glu Leu Ser Arg Phe Glu Phe Asn Gln Ala Leu Gly
        370                 375                 380
Arg Pro Glu Lys Ile His Asn Lys Leu Glu Phe Pro Gln Val Leu Tyr
385                 390                 395                 400
Leu Asp Arg Tyr Met His Arg Asn Arg Glu Ile Thr Arg Ile Lys Arg
                405                 410                 415
Glu Glu Ile Lys Arg Leu Lys Asp Tyr Leu Thr Val Leu Gln Gln Arg
            420                 425                 430
Leu Glu Arg Tyr Leu Ser Tyr Gly Ser Gly Pro Lys Arg Phe Pro Leu
            435                 440                 445
Val Asp Val Leu Gln Tyr Ala Leu Glu Phe Ala Ser Ser Lys Pro Val
        450                 455                 460
Cys Thr Ser Pro Val Asp Asp Ile Asp Ala Ser Ser Pro Pro Ser Gly
465                 470                 475                 480
Ser Ile Pro Ser Gln Thr Leu Pro Ser Thr Thr Glu Gln Gln Gly Ala
                485                 490                 495
Leu Ser Ser Glu Leu Pro Ser Thr Ser Pro Ser Ser Val Ala Ala Ile
            500                 505                 510
Ser Ser Arg Ser Val Ile His Lys Pro Phe Thr Gln Ser Arg Ile Pro
            515                 520                 525
Pro Asp Leu Pro Met His Pro Ala Pro Arg His Ile Thr Glu Glu Glu
        530                 535                 540
Leu Ser Val Leu Glu Ser Cys Leu His Arg Trp Arg Thr Glu Ile Glu
545                 550                 555                 560
Asn Asp Thr Arg Asp Leu Gln Glu Ser Ile Ser Arg Ile His Arg Thr
                565                 570                 575
Ile Glu Leu Met Tyr Ser Asp Lys Ser Met Ile Gln Val Pro Tyr Arg
            580                 585                 590
Leu His Ala Val Leu Val His Glu Gly Gln Ala Asn Ala Gly His Tyr
            595                 600                 605
Trp Ala Tyr Ile Phe Asp His Arg Glu Ser Arg Trp Met Lys Tyr Asn
        610                 615                 620
Asp Ile Ala Val Thr Lys Ser Ser Trp Glu Glu Leu Val Arg Asp Ser
625                 630                 635                 640
Phe Gly Gly Tyr Arg Asn Ala Ser Ala Tyr Cys Leu Met Tyr Ile Asn
                645                 650                 655
Asp Lys Ala Gln Phe Leu Ile Gln Glu Glu Phe Asn Lys Glu Thr Gly
            660                 665                 670
Gln Pro Leu Val Gly Ile Glu Thr Leu Pro Pro Asp Leu Arg Asp Phe
            675                 680                 685
Val Glu Glu Asp Asn Gln Arg Phe Glu Lys Glu Leu Glu Glu Trp Asp
        690                 695                 700
Ala Gln Leu Ala Gln Lys Ala Leu Gln Glu Lys Leu Leu Ala Ser Gln
705                 710                 715                 720
Lys Leu Arg Glu Ser Glu Thr Ser Val Thr Thr Ala Gln Ala Ala Gly
                725                 730                 735
Asp Pro Glu Tyr Leu Glu Gln Pro Ser Arg Ser Asp Phe Ser Lys His
            740                 745                 750
```

-continued

```
Leu Lys Glu Glu Thr Ile Gln Ile Ile Thr Lys Ala Ser His Glu His
        755                 760                 765

Glu Asp Lys Ser Pro Glu Thr Val Leu Gln Ser Ala Ile Lys Leu Glu
        770                 775                 780

Tyr Ala Arg Leu Val Lys Leu Ala Gln Glu Asp Thr Pro Pro Glu Thr
785                 790                 795                 800

Asp Tyr Arg Leu His His Val Val Val Tyr Phe Ile Gln Asn Gln Ala
                805                 810                 815

Pro Lys Lys Ile Ile Glu Lys Thr Leu Leu Glu Gln Phe Gly Asp Arg
                820                 825                 830

Asn Leu Ser Phe Asp Glu Arg Cys His Asn Ile Met Lys Val Ala Gln
        835                 840                 845

Ala Lys Leu Glu Met Ile Lys Pro Glu Glu Val Asn Leu Glu Glu Tyr
        850                 855                 860

Glu Glu Trp His Gln Asp Tyr Arg Lys Phe Arg Glu Thr Thr Met Tyr
865                 870                 875                 880

Leu Ile Ile Gly Leu Glu Asn Phe Gln Arg Glu Ser Tyr Ile Asp Ser
                885                 890                 895

Leu Leu Phe Leu Ile Cys Ala Tyr Gln Asn Asn Lys Glu Leu Leu Ser
                900                 905                 910

Lys Gly Leu Tyr Arg Gly His Asp Glu Glu Leu Ile Ser His Tyr Arg
        915                 920                 925

Arg Glu Cys Leu Leu Ile Leu Asn Leu Lys Arg Lys Gln Lys Pro Ile
        930                 935                 940

Leu Phe Phe Phe Leu His Cys Ile Lys Lys Leu Asn Glu Gln Ala Ala
945                 950                 955                 960

Glu Leu Phe Glu Ser Gly Glu Asp Arg Glu Val Asn Asn Gly Leu Ile
                965                 970                 975

Ile Met Asn Glu Phe Ile Val Pro Phe Leu Pro Leu Leu Val Asp
                980                 985                 990

Glu Met Glu Glu Lys Asp Ile Leu  Ala Val Glu Asp Met  Arg Asn Arg
        995                 1000                1005

Trp Cys  Ser Tyr Leu Gly Gln  Glu Met Glu Pro His  Leu Gln Glu
    1010                 1015                1020

Lys Leu  Thr Asp Phe Leu Pro  Lys Leu Leu Asp Cys  Ser Met Glu
    1025                 1030                1035

Ile Lys  Ser Phe His Glu Pro  Pro Lys Leu Pro Ser  Tyr Ser Thr
    1040                 1045                1050

His Glu  Leu Cys Glu Arg Phe  Ala Arg Ile Met Leu  Ser Leu Ser
    1055                 1060                1065

Arg Thr  Pro Ala Asp Gly Arg
    1070                1075
```

MODULATORS OF LEUKOCYTE ACTIVATION, COMPOSITIONS AND METHODS OF USE

The present application incorporates U.S. patent application Ser. No. 09/404,967 filed 24 Sep. 1999, in its entirety by reference. The present application incorporates PCT Application Serial No. US00/26338 filed 25 Sep. 2000, in its entirety by reference. The present application claims priority to U.S. Provisional Patent Application Ser. No. 60/280,698 filed Mar. 29, 2001, which is incorporated herein in its entirety by reference.

FIELD OF THE INVENTION

The present invention provides compositions and methods for modulating leukocyte activation. Nucleic acids encoding proteins and proteins so encoded which are capable of modulating leukocyte activation are provided. Compositions and methods for the treatment of disorders related to leukocyte dysfunction or dysregulation are also provided. Prophylactics and methods for the prevention of such disorders are also provided. Also provided are compositions and methods for diagnostic and prognostic determination of such disorders. Further provided are assays for the identification of bioactive agents capable of modulating leukocyte activation.

BACKGROUND OF THE INVENTION

The immune response consists of a cellular response and a humoral response. The cellular response is mediated largely by T lymphocytes (alternatively and equivalently referred to herein as T cells), while the humoral response is mediated by B lymphocytes (alternatively and equivalently referred to herein as B cells).

B cells produce and secrete antibodies in response to the presentation of antigen and MHC class II molecules on the surface of antigen presenting cells. Antigen presentation initiates B cell activation with the engagement of the B cell receptor (BCR) at the cell's surface. Following engagement, the BCR relays signals that are propagated through the cell's interior via signal transduction pathways. These signals lead to changes in B cell gene expression, physiology, and function which underlie B cell activation.

T cells produce costimulatory molecules that augment antibody production by B cells during the humoral immune response. Many T cells also act directly in an immune response to engulf and destroy cells or agents that they recognize by virtue of the cell surface receptors they possess. The engagement of cell surface receptors on T cells results in the propagation of intracellular signals which provoke changes in T cell gene expression, physiology, and function which underlie the cellular immune response.

Non-lymphocyte leukocytes and platelets are also activated by surface receptor engagement in immune and in response to injury. For example, mast cells and basophils are activated by binding of antigen to surface IgE, while platelets are activated by the binding of thrombin to its receptor.

Intercellular communication between different types of lymphocytes, as well as between lymphocytes and non-lymphocytes in the normally functioning immune system is well known. Much of this communication is mediated by cytokines and their cognate receptors. Cytokine-induced signals begin at the cell surface with a cytokine receptor and are transmitted intracellularly via signal transduction pathways. Many types of cells produce cytokines, and cytokines can induce a variety of responses in a variety of cell types, including leukocytes. The response to a cytokine can be context-dependent as well as cell type specific.

The dysregulation of intercellular communication can perturb leukocyte activity and the regulation of immune responses. Such dysregulation is believed to underlie certain autoimmune disease states, hyper-immune states, and immune-compromised states. Such dysfunction may be cell autonomous or non-cell autonomous with respect to lymphocytes.

The activation of specific signaling pathways in leukocytes determines the quality, magnitude, and duration of immune responses. In response to transplantation, in acute and chronic inflammatory diseases, and in autoimmune responses, it is these pathways that are responsible for the induction, maintenance and exacerbation of undesirable leukocyte responses. Identification of these signaling pathways is desirable in order to provide diagnostic and prognostic tools, as well as therapeutic targets for modulating leukocyte function in a variety of disorders or altered physiological states. In addition, the ability to modulate these pathways and suppress normal immune responses is often desirable, for example in transplantation.

While the extracellular domains and cognate ligands of lymphocyte receptors vary widely, many receptors have similar intracellular domains (such as the "immunoreceptor tyrosine-based activation motif" (ITAM)), and associate with common intracellular signaling molecules.

Tyrosine kinase activation is a critical event in the propagation of intracellular signals by many receptors on lymphocytes, including antigen receptors on B and T cells (for a review see Turner et al., Immunology Today, 21:148–154, 2000, incorporated herein in its entirety by reference)

With regard to the B cell antigen receptor, the BCR is rapidly phosphorylated on tyrosine residues following engagement of the receptor by antigen or other crosslinking agents. This tyrosine phosphorylation leads to associations with several SH2-containing signaling proteins. SH2-containing proteins are known to bind to phosphorylated tyrosine residues in the context of specific amino acid sequences.

Many non-receptor tyrosine kinases have been shown to interact with tyrosine phosphorylated receptors in lymphocytes, including the antigen receptors of B and T cells. These non-receptor tyrosine kinases include members of the src family and the Bruton's tyrosine kinase (BTK) family. Importantly, many of these genes are associated with oncogenesis.

A structurally distinct group of non-receptor tyrosine kinases that associate with tyrosine phosphorylated receptors in lymphocytes are the "SYK" proteins (referred to herein as SYK). SYK is a 72 kilodalton cytoplasmic protein tyrosine kinase that is expressed in a variety of cells of the haematopoietic lineage, including B and T cells. SYK is activated in B cells by aggregation of the B cell antigen receptor (BCR) (Hutchcroft et al., JBC 267:8613–8619, 1992), in T cells by cross-linking the T-cell antigen receptor (TCR) (Chan, A., et al., J. Immunol., 152:4758–4766, 1994; Couture, C., et al., Proc. Natl. Acad. Sci. U.S.A., 91:5301–5305, 1994), in mast cells by aggregation of FceRI receptors (Hutchcroft et al., PNAS 89:9107–9111, 1992), in platelets by thrombin (Taniguchi, T., et al., J. Biol. Chem 268:2277–2279, 1993) or integrin ligation (Clark, E. A., et al., J. Biol. Chem., 269:28859–28864, 1994), in monocytes by cross-linking FcγRI ad FcγRII receptors (Agarwal, A., et al., J. Biol. Chem., 268:15900–15905, 1993; Kiener, P. A., et al., J. Biol. Chem., 268:24442–24448, 1993), in macrophages by engagement of the FcγRIIIA receptor (Darby, C., et al., J. Immunol., 152:5429–5437, 1994), in granulocytes in response to granulocyte stimulating factor, and in peripheral blood lymphocytes by interleukin-2. SYK contains two tandem SH2 domains and multiple tyrosines that when phosphorylated can serve as binding sites for additional signaling proteins including phospholipase C-γ, VAV, and CBL (Junghans, Immunol. Today, 20:401–406, 1999; Sklar et al., Cytometry, 3:161–165, 1982; Robins et al., J. Immunol. Methods, 90:165–172, 1986).

SYK is tyrosine phosphorylated in B cells activated by BCR engagement, and is essential for the development and function of B cells. Activation of the BCR (used herein interchangeably with "engagement of the BCR") at different developmental stages evokes different cellular responses. In immature B cells, stimulation of the newly formed surface immunoglobulin leads to cell death or rearrangement of light chain genes (MacLennan, Curr. Opin. Immunol. 10:22–225, 1998). In mature B cells, BCR engagement leads to proliferation and differentiation into antibody-producing cells or memory B cells (MacLennan, Curr. Opin. Immunol. 10:22–225, 1998). In addition, it is believed that stimulation of the immunoglobulin pathway is required for immature B cells to differentiate into mature, recirculating follicular B cells. Importantly, B cell maturation and humoral immunity are compromised in SYK deficient mice (Turner et al., Nature, 378:298–302, 1995), underscoring the importance of SYK-mediated signal transduction in B and T cells.

The activity of protein tyrosine kinases and other signaling proteins is generally tightly regulated in normal cells. One method of controlling signaling protein activity involves conjugation of ubiquitin or ubiquitin-like proteins to signaling proteins.

Ubiquitin is a 76-amino acid polypeptide that is highly conserved in eukaryotes. Several ubiquitin coding loci identified in yeast are differentially expressed in cells during exponential growth, stationary phase, and during stress such as high temperature or starvation [Ozkaynak et al. *EMBO J.* 6(5):1429–1439 (1987)]. In one aspect, ubiquitin mediates selective proteolysis by conjugating to intracellular proteins, thereby targeting them to the proteosome where they are cleaved adjacent to the C-terminal of the ubiquitin moiety. Conjugation of ubiquitin to a target protein may also result in an alteration in the subcellular localization or activity of the signaling protein without proteolytic degradation (for example see Depraetere, Nat. Cell Biol., 3:E181).

Such modifications of target proteins are reversible. The level of target protein conjugation is negatively influenced by the action of peptidases with activity specifically directed at ubiquitin. The ubiquitin-specific proteases comprise a family of proteins which have both proteolytic ability and the ability to deubiquitinate the ubiquitin-protein conjugate [Tobias et al., *J. Biol. Chem.* 266(18):12021–12028 (1991); Baker et al., *J. Biol. Chem.* 267(32):23364–23375 (1992); Xiao et al., *Yeast* 10(11): 1497–1502 (1994); Baek et al., *J. Biol. Chem.* 272(41):25560–25565 (1997) enzymes are able to remove ubiquitin from substrate proteins, thereby interrupting their transport to the proteosome for destruction. A very large number of deubiquitinating enzymes are known to exist, which raises the possibility that individual enzymes may recognize distinct ubiquitin-conjugated substrates. Substrate specificity among deubiquitinating enzymes has been demonstrated previously (Jensen et al., Oncogene 16:1097–1112, 1998; Kahana et al., Mol. Cell. Biol. 19:6608–6620, 1999; Moazed et al., Cell 86:667–677, 1996). Such proteases may remove ubiquitin conjugated to target proteins thereby altering the subcellular localization, activity, and/or proteolytic processing of target proteins.

Coordinated intracellular protein degradation is critical to a vast array of cellular processes, including cytokine signaling in lymphocytes. In addition, it has been suggested that the dysregulation of ubiquitin mediated proteolysis may be involved in the development of cancer in mammals, due to the association of a ubiquitin specific protease with cell cycle regulatory proteins [Xiao et al., supra].

Similarly, conjugation of ubiquitin-like proteins to a target protein often results in the modification of target protein activity and/or subcellular distribution. For example, conjugation of the ubiquitin-like proteins SUMO and NEDD8 to target proteins alters their subcellular localization and stability (Muller et. al., Nat. Rev. Mol. Cell. Biol., 2:202–210, 2001; Yeh et. al., Gene, 248:1–14, 2000).

UBC9 is a ubiquitin-conjugating enzyme which also catalyzes SMT3/SUMO conjugation to target proteins (Schwarz et. al., Proc. Nat'l. Acad. Sci., 95:560–564,1998). Further, these modifications are also reversible, and proteases may remove ubiquitin-like proteins conjugated to target proteins thereby altering the subcellular localization, activity, and/or proteolytic processing of target proteins (for example see Kim et. al., J. Biol. Chem., 275:14102–14106, 2000).

Compositions that are capable of modulating the conjugation of ubiquitin and ubiquitin-like proteins to signaling proteins are desirable and provide means for modulating signal transduction. Such compositions are desirable for the modulation of leukocyte activation in normal and abnormal immune responses.

SUMMARY OF THE INVENTION

The present invention provides compositions and methods for modulating leukocyte and platelet activation. Nucleic acids encoding proteins and proteins so encoded which are capable of modulating leukocyte and platelet activation are provided. Compositions and methods for the treatment of disorders related to leukocyte dysfunction and dysregulation are also provided. Prophylactics and methods for the prevention of such disorders are also provided. Also provided are compositions and methods for diagnostic and prognostic determination of such disorders. Further provided are assays for the identification of bioactive agents capable of modulating leukocyte activation.

Accordingly, in one embodiment, the invention provides USP-25 nucleic acids encoding USP-25 proteins which are capable of modulating leukocyte and platelet activation. Also provided herein are USP-25 proteins capable of modulating leukocyte and platelet activation. SYK-UBP, SUP and USP-25 are used herein equivalently and interchangeably.

In a preferred embodiment, the USP-25 nucleic acid comprises a nucleic acid sequence having at least about 85%, more preferably at least about 90%, more preferably at least about 95%, more preferably at least about 98% identity to the nucleic acid sequence set forth in SEQ ID NO:1 or 3. In a preferred embodiment, the USP-25 nucleic acid comprises the nucleic acid sequence set forth in SEQ ID NO:1 or 3. In a preferred embodiment, the USP-25 nucleic acid encodes a USP-25 protein.

In a preferred embodiment, the USP-25 protein comprises an amino acid sequence encoded by a nucleic acid sequence having at least about 85%, more preferably at least about 90%, more preferably at least about 95%, more preferably at least about 98% identity to the nucleic acid sequence set forth in SEQ ID NO:1 or 3. In a preferred embodiment, the USP-25 protein comprises an amino acid sequence encoded by the nucleic acid sequence set forth in SEQ ID NO:1 or 3.

Also provided herein are USP-25 antisense nucleic acids which nucleic acids will hybridize under high stringency conditions to a USP-25 nucleic acid comprising the nucleic acid sequence set forth in SEQ ID NO:1 or 3. In a preferred embodiment, the USP-25 antisense nucleic acid inhibits expression of USP-25 protein encoded by USP-25 nucleic acid. In a preferred embodiment, the USP-25 antisense nucleic acid inhibits USP-25 protein activity. In a preferred embodiment, the USP-25 antisense nucleic acid has at least one activity possessed by a dominant negative USP-25 protein described herein.

In a preferred embodiment, the USP-25 protein comprises an amino acid sequence having at least about 85%, more preferably at least about 90%, more preferably at least about 95%, more preferably at least about 98% identity to the amino acid sequence set forth in SEQ ID NO:2 or 4. In a preferred embodiment, the USP-25 protein comprises the amino acid sequence set forth in SEQ ID NO:2 or 4. Preferably, the USP-25 protein also possesses one or more USP-25 bioactivities described herein.

In a preferred embodiment, the USP-25 protein is capable of binding to the SYK protein. In another preferred embodiment, the USP-25 protein is capable of binding to calcineurin. In another preferred embodiment, the USP-25 protein is capable of binding to UBC9. In another preferred embodiment, the USP-25 protein is capable of binding to a SYK, calcineurin, or UBC9 protein that is conjugated to ubiquitin or ubiquitin-like proteins such as the SMT3/SUMO and NEDD/Ruby ubiquitin-like proteins. In a preferred embodiment, the USP-25 protein removes ubiquitin or ubiquitin-like proteins from conjugated SYK, calcineurin or UBC9 protein. In a preferred embodiment, USP-25 mediated removal of ubiquitin or ubiquitin-like proteins from target proteins involves USP-25 peptidase activity.

In one aspect, the USP-25 protein provided herein modulates SYK tyrosine kinase activity. In one aspect, the USP-25 protein provided herein modulates calcineurin activity. In one aspect, the USP-25 protein provided herein modulates UBC9 activity.

In one aspect of the invention, expression vectors are provided. The expression vectors comprise one or more USP-25 nucleic acids provided herein operably linked to regulatory sequences recognized by a host cell transformed with the expression vector. Further provided herein are host cells comprising expression vectors and USP-25 nucleic acids provided herein. Also provided are processes for producing USP-25 protein comprising culturing a host cell provided herein under conditions suitable for expression of the USP-25 protein. In one embodiment, the process includes recovering the USP-25 protein.

The present invention also provides isolated polypeptides which specifically bind to a USP-25 protein. In one aspect, the polypeptide is an antibody. In a preferred aspect, the polypeptide is a monoclonal antibody.

Provided herein are methods for screening for a bioactive agent capable of binding to the USP-25 protein. In one aspect, the method comprises combining a USP-25 protein and a candidate bioactive agent and determining the binding of candidate agent to USP-25 protein. In one aspect, the method involves identifying the candidate agent.

Also provided herein are methods for screening for a bioactive agent capable of interfering with the binding of a USP-25 protein. In one aspect, the method comprises combining a candidate bioactive agent, a USP-25 protein, and a USP-25 binding partner which will bind to USP-25 in the absence of candidate agent and determining the binding of USP-25 to binding partner in the presence of candidate bioactive agent. In a preferred aspect, the USP-25 binding partner is selected from UBC9, calcineurin, SYK, and ubiquitin conjugates thereof and ubiquitin-like protein conjugates thereof. In another aspect, the method involves determining the binding of USP-25 to binding partner in the presence and absence of candidate bioactive agent. In one aspect, USP-25 and USP-25 binding partner are combined first. In one aspect, the method involves identifying the candidate agent.

Also provided herein are methods for screening for a bioactive agent capable of increasing the binding of a USP-25 protein. In one aspect, the method comprises combining a candidate bioactive agent, a USP-25 protein, and a USP-25 binding partner which will bind to USP-25 in the absence of candidate agent and determining the binding of USP-25 to binding partner in the presence of candidate bioactive agent. In a preferred aspect, the USP-25 binding partner is selected from UBC9, calcineurin, SYK, and ubiquitin conjugates thereof and ubiquitin-like protein conjugates thereof. In another aspect, the method involves determining the binding of USP-25 to binding partner in the presence and absence of candidate bioactive agent. In one aspect, USP-25 and USP-25 binding partner are combined first. In one aspect, the method involves identifying the candidate agent.

Provided herein are methods for screening for a bioactive agent capable of modulating SYK tyrosine kinase activity. In one aspect, the method comprises contacting a candidate bioactive agent to a cell comprising a recombinant USP-25 nucleic acid and expressing USP-25 protein, and further comprising a SYK protein, and determining the tyrosine kinase activity of SYK in the presence of candidate agent. Preferably, tyrosine kinase activity is determined in the presence and absence of candidate agent.

Also provided herein are methods for screening for an agent capable of modulating the ubiquitination of a target protein that is capable of being ubiquitinated. In one aspect, the method comprises combining a USP-25 protein, a candidate bioactive agent, ubiquitin or polyubiquitin, a ubiquitin conjugating enzyme and/or ubiquitin ligase capable of ubiquitinating a target protein, and a USP-25 target protein, and determining the level of ubiquitination of target protein in the presence of candidate agent. In a preferred embodiment, the level of ubiquitination of target protein is determined in the presence and absence of candidate agent. In a preferred embodiment, the target protein is selected from SYK, UBC9 and calcineurin. The level of target protein ubiquitination may be determined by determining the amount of ubiquitin-conjugated target protein. Alternatively, the level of target protein ubiquitination may be determined by determining the amount of free ubiquitin.

In another aspect, the method comprises combining a USP-25 protein, a candidate bioactive agent and a ubiquitin-conjugated target protein, and determining the level of ubiquitination of target protein in the presence of candidate agent. In a preferred embodiment, the level of ubiquitination of target protein is determined in the presence and absence of candidate agent. In a preferred embodiment, the target protein is selected from SYK, UBC9 and calcineurin.

Also provided herein are methods for screening for an agent capable of modulating the conjugation of ubiquitin-like proteins to a target protein that is capable of being so conjugated. In one aspect, the method comprises combining a USP-25 protein, a candidate bioactive agent, a ubiquitin-like protein or complex thereof, an appropriate conjugating enzyme and/or ligase capable of conjugating the ubiquitin-like protein or complex thereof to a target protein, and a USP-25 target protein, and determining the level of ubiquitin-like protein conjugation to target protein in the presence of candidate agent. In a preferred embodiment, the level of ubiquitin-like protein conjugation to target protein is determined in the presence and absence of candidate agent. In a preferred embodiment, the target protein is selected from SYK, UBC9 and calcineurin. In a preferred embodiment, the ubiquitin-like protein is SMT3/SUMO or NEDD/Ruby. The level of target protein conjugation may be determined by determining the amount of conjugated target protein. Alternatively, the level of target protein conjugation may be determined by determining the amount of free ubiquitin-like protein.

In another aspect, the method comprises combining a USP-25 protein, a candidate bioactive agent and a target protein conjugated to a ubiquitin-like protein, and determining the level of conjugation to target protein in the presence of candidate agent. In a preferred embodiment, the level of conjugation to target protein is determined in the presence and absence of candidate agent. In a preferred embodiment, the target protein is selected from SYK, UBC9 and calcineurin. In a preferred embodiment, the ubiquitin-like protein is SMT3/SUMO or NEDD/Ruby.

Also provided herein are methods for screening for a bioactive agent capable of modulating the activity of a USP-25 protein. In one aspect, the method comprises contacting a candidate bioactive agent to a cell comprising a recombinant USP-25 nucleic acid and expressing USP-25 protein. In one aspect, the method comprises contacting a library of candidate bioactive agents to a plurality of cells comprising a recombinant USP-25 nucleic acid and expressing USP-25 protein. In one embodiment, the method comprises determining the level of ubiquitination of a USP-25 target protein. Preferably the target protein is selected from SYK, calcineurin and UBC9. In another embodiment, the method comprises determining the level of conjugation of ubiquitin-like proteins to a USP-25 target protein. Preferably the target protein is selected from SYK, calcineurin and UBC9. Preferably the ubiquitin-like protein is SMT3/SUMO or NEDD/Ruby. In one embodiment, the method comprises determining the activity of SYK, calcineurin or UBC9.

In one aspect, the method comprises determining the ubiquitin-specific peptidase activity of a USP-25 protein directed at ubiquitin conjugated target protein in the presence of candidate agent. Such screening may be done in vitro or in vivo. In vitro, USP-25 may be cell-free as in a cell lysate, or purified. In a preferred embodiment, peptidase activity is determined in the presence and absence of candidate agent. In a preferred embodiment, the target protein is selected from SYK, UBC9 and calcineurin.

In one aspect, the method comprises determining USP-25 peptidase activity directed at ubiquitin-like protein conjugated to target protein in the presence of candidate agent. Such screening may be done in vitro or in vivo. In vitro, USP-25 may be cell-free as in a cell lysate, or purified. In a preferred embodiment, peptidase activity is determined in the presence and absence of candidate agent. In a preferred embodiment, the target protein is selected from SYK, UBC9 and calcineurin. In a preferred embodiment, the ubiquitin-like protein is SMT3/SUMO or NEDD/Ruby.

In one aspect the method comprises expressing USP-25 nucleic acid in a leukocyte or like cell, contacting the expressing cell to a candidate agent, and determining the level of expression of a surface marker which is associated with activation of the leukocyte, in the presence of candidate agent. In a preferred embodiment, the level of surface marker expression is determined in the presence and absence of candidate agent. In a preferred embodiment, the leukocyte is a T lymphocyte or B lymphocyte. In a preferred embodiment, the surface marker is selected from the group consisting of CD23, CD69, CD80 and CD86.

In one aspect, the method comprises expressing USP-25 nucleic acid in a leukocyte or like cell, contacting the expressing cell to a candidate agent, and determining the level of activity of a promoter which activity correlates with activation of the leukocyte, in the presence of candidate agent. In a preferred embodiment, the level of promoter activity is determined in the presence and absence of candidate agent. In a preferred embodiment, the leukocyte is a T lymphocyte or a B lymphocyte. In a preferred embodiment the promoter is the nuclear factor activated in T cells gene (NFAT) promoter. In another preferred embodiment, the promoter is the immunoglobulin heavy chain gene promoter.

Also provided herein are methods for screening for a bioactive agent capable of modulating leukocyte and platelet activation. In one aspect, the method comprises contacting a candidate bioactive agent to a cell comprising a recombinant USP-25 nucleic acid and expressing USP-25 protein, and determining the effect of candidate agent on the cell. In one aspect, the method comprises contacting a library of candidate bioactive agents to a plurality of cells comprising a recombinant USP-25 nucleic acid and expressing USP-25 protein. In one embodiment, the method comprises determining the level of ubiquitination of a USP-25 target protein. Preferably the target protein is selected from SYK, calcineurin and UBC9. In another embodiment, the method comprises determining the level of conjugation of ubiquitin-like proteins to a target protein. Preferably the target protein is selected from SYK, calcineurin and UBC9. Preferably, the ubiquitin-like protein is SMT3/SUMO or NEDD/Ruby. In one embodiment, the method comprises determining the activity of SYK, calcineurin or UBC9.

In one aspect, the method comprises determining the ubiquitin-specific peptidase activity of a USP-25 protein directed at ubiquitin conjugated target protein in the presence of candidate agent. Such screening may be done in vitro or in vivo. In vitro, USP-25 may be cell-free as in a cell lysate, or purified. In a preferred embodiment, peptidase activity is determined in the presence and absence of candidate agent. In a preferred embodiment, the target protein is selected from SYK, UBC9 and calcineurin.

In one aspect, the method comprises determining USP-25 peptidase activity directed at ubiquitin-like protein conjugated to target protein in the presence of candidate agent. Such screening may be done in vitro or in vivo. In vitro, USP-25 may be cell-free as in a cell lysate, or purified. In a preferred embodiment, peptidase activity is determined in the presence and absence of candidate agent. In a preferred embodiment, the target protein is selected from SYK, UBC9 and calcineurin. In a preferred embodiment, the ubiquitin-like protein is SMT3/SUMO or NEDD/Ruby.

In one aspect the method comprises expressing USP-25 nucleic acid in a leukocyte or like cell, contacting the expressing cell to a candidate agent, and determining the level of expression of a surface marker which is associated with activation of the leukocyte, in the presence of candidate agent. In a preferred embodiment, the level of surface marker expression is determined in the presence and absence of candidate agent. In a preferred embodiment, the leukocyte is a T lymphocyte or B lymphocyte. In a preferred embodiment, the surface marker is selected from the group consisting of CD23, CD69, CD80 and CD86.

In one aspect, the method comprises expressing USP-25 nucleic acid in a leukocyte or like cell, contacting the expressing cell to a candidate agent, and determining the level of activity of a promoter which activity correlates with activation of the leukocyte, in the presence of candidate agent. In a preferred embodiment, the level of promoter activity is determined in the presence and absence of candidate agent. In a preferred embodiment, the leukocyte is a T lymphocyte or a B lymphocyte. In a preferred embodiment the promoter is the nuclear factor activated in T cells gene (NFAT) promoter. In another preferred embodiment, the promoter is the immunoglobulin heavy chain gene promoter.

In one aspect, the method comprises screening for an agent capable of binding to a USP-25 protein using assays provided herein.

In one aspect, the method comprises screening for an agent capable of modulating the binding of a USP-25 protein using assays provided herein.

In one aspect, the method comprises screening for an agent capable of modulating USP-25 protein activity using assays provided herein.

Compositions and methods for the modulation of leukocyte activation are also provided herein. These include proteins, nucleic acids and small molecule chemical compositions. These compositions find use as prophylactics and therapeutics for the prevention and treatment of physiological states related to dysfunctional or dysregulated leukocyte activation. In a preferred embodiment, provided herein are small molecule chemical compositions useful for the prevention and treatment of acute inflammatory disorders, chronic inflammatory disorders, autoimmune disorders, and transplant rejection.

BRIEF DESCRIPTION OF THE DRAWINGS

FIGS. 1A and 1B show the nucleic acid sequence encoding cell cycle protein SYK-UBP—isoform 1, SEQ ID NO:1, wherein a translation start codon (ATG), an in frame upstream termination codon (TGA) and translation termination codon (TAA) are in bold and underlined.

FIG. 2 shows the amino acid sequence of cell cycle protein SYK-UBP—isoform 1, SEQ ID NO:2.

FIGS. 3A and 3B show the nucleic acid sequence encoding cell cycle protein SYK-UBP—isoform 2, SEQ ID NO:3, wherein a translation start codon (ATG), an in frame upstream termination codon (TGA) and translation termination codon (TAA) are in bold and underlined. Appearing in bold without underline is the nucleic acid sequence found in isoform 2 and not in isoform 1 of SYK-UBP.

FIG. 4 shows the amino acid sequence of cell cycle protein SYK-UBP—isoform 2, SEQ ID NO:4.

FIG. 5 shows domain analysis of the amino acid sequence of SUP protein (SEQ ID NO:5. The cysteine residue which is characteristic of ubiquitin specific protease domains is enlarged and bolded. The two conserved histidine residues that are characteristic of ubiquitin specific protease domains are enlarged.

FIG. 6 summarizes results demonstrating that a C→S catalytically dead mutant isoform of SUP acts in dominant negative fashion to inhibit NFAT promoter activation in response to surface Ig stimulation in B cells.

FIG. 7 schematically depicts a mechanism for the regulation of BCR signaling by SUP involving SUP-mediated regulation of SYK protein ubiquitination.

FIG. 8 shows results of yeast two hybrid screen using SYK protein as bait. The hits listed aer nucleic acids encoding segments of the USP-25 protein.

FIG. 9A shows domain analysis of the amino acid sequence of SUP protein. The protein sequence is broken down into the ubiquitin-associated domain, the ubiquztin protease domain, and the response regulatory domain. The catalytic cysteine active site with a conserved cysteine residue which is characteristic of ubiquitin specific protease domains is indicated. The PKC site is indicated. The tyrosine phosphorylation site is indicated. The active site conserved histidines characteristic of ubiquitin specific protease domains are indicated.

FIG. 9B shows Northern blot of USP-25 mRNA expression in human tissue samples and human cancer cell lines.

FIGS. 10A and 10B show catalytically inactive USP-25 C to S mutant blocks TCR-induced expression of luciferase reporter gene fused to NFAT gene promoter in transfected cells. Cells transfected with USP-25 C to S catalytic mutant "SUP(C>S)", USP-25 wildtype "SUPwt", or empty vector pEFnig. USP-25 C to S catalytic mutant also referred to herein as dominant negative USP-25 protein variant or grammatical equivalents. Luciferase activity is shown in FIG. 10A and is determined in cells exposed to different concentrations of C305 (0, 100, 300, 1000 ng/mL0 which activates TCR. Western blots "wb" showing protein expression in cells are also provided in FIG. 10B.

FIG. 10C shows USP-25 C to S catalytic mutant inhibits NFAT promoter activity by acting downstream of calcium signaling. Cells in the presence or absence of phorbol ester and calcium ionophore (PMA+iono,+ or −) and transfected with expression vectors encoding USP-25 C to S catalytic mutant "SUPmt" or USP-25 wildtype "SUPwt" or empty vector. NFAT promoter fused to luciferase reporter gene and luciferase activity determined.

FIGS. 11A and 11B show USP-25 C to S catalytic mutant does not affect AP-1 activation by TCR activation or phorbol ester and calcium ionophore. AP-1 responsive elements fused to luciferase reporter gene in cells transfected with empty vector "PCDEF-nig", wildtype USP-25 "SUPwt-nig", USP-25 C to S catalytic mutant "SUP(C>M)-nig", or PAK2L "PAK2L-nig". In the presence or absence of phorbol ester and ionomycin (PMA/iono + or −), luciferase activity determined, as shown in FIG. 11B. Cells exposed to different concentration of C305 (0 ng/mL, 100 ng/mL, 300 ng/mL) which activates TCR. and luciferase activity determined, as shown in FIG. 11A.

FIGS. 11C–11N show catalytically inactive USP-25 does not affect TCR-induced calcinm flux. FACS analysis of cells transfected with empty vector "PCDEF nig vector" FIGS. 11C–11E, or expression vector encoding wildtype USP-25 "PCDEF SUP wt" FIGS. 11F–11H, or USP-25 C to S catalytic mutant "PCDEF SUP mutant" FIGS. 11I–11K, or TRAC "PCDEF TRAC" FIGS. 11L–11N.

FIGS. 12A–12L show USP-25 C to S catalytic mutant does not affect CD69 expression. FACS analysis of cells transfected with empty vector "pEFnig", or expression vector encoding wildtype USP-25 protein "SUP-wt", USP-25 C to S catalytic mutant "SUP(C>S) or PAK2L "PAK2L", and exposed to different concentrations of C305 (0, FIGS. 12A–12D; 10) ng/mL, FIGS. 12E–12H; and 300 ng/mL, FIGS. 12I–12L;) which activates TCR.

FIG. 12M and 12N show N-terminal USP-25 truncation mutants inhibit NFAT promoter activity. FIG. 12M shows the structure of wildtype USP-25 and three N-terminal truncation mutants thereof (58–1060, 659–1060, and 861–1060). NFAT promoter is linked to luciferase reporter gene and luciferaso activity is determined in cells transfecned with empty vector "pEFnig" or expression vectors encoding wildtype USP-25 "SUP-wt", or one of the three indicated N-terminal truncations mutants thereof, or SLIM "SLIM nig", and exposed to different concentrations of C305 (0, 1000 ng/mL, 300 ng/mL, 1000 ng/mL) which activates TCR. FIG. 12N shows the results of the lucifierase assay.

FIG. 13A shows USP-25 C to S catalytic mutant inhibits NFAT activity in BJAB cells. NFAT promoter is fused to luciferase reporter gene and luciferase activity is determined in cells transfected with empty vector "pEFnig", or expression vector encoding wildtype USP-25 "SUP-wt", or one of three N-terminal truncation mutants thereof and described in FIG. 12 (bottom), or USP-25 C to S catalytic mutant "SUP(C>S)", or SLIM "SLIMnig", and exposed to varied concentrations of anti-IgM antibody (0,100 ng/mL, 300 ng/mL).

FIG. 13B is a schematic depiction of the possible regulatory role of USP-25 on the NFAT promoter.

FIG. 14 is a schematic depiction of the possible regulatory role of USP-25 on the NFAT promoter.

DETAILED DESCRIPTION OF THE INVENTION

The present invention provides compositions and methods for modulating leukocyte and platelet activation. Nucleic acids encoding proteins and proteins so encoded which are capable of modulating leukocyte and platelet activation are provided. Compositions and methods for the treatment of disorders related to leukocyte dysfunction and dysregulation are also provided. Prophylactics and methods for the prevention of such disorders are also provided. Also provided are compositions and methods for diagnostic and prognostic determination of such disorders. Further provided are assays for the identification of bioactive agents capable of modulating leukocyte activation.

Accordingly, the present invention provides USP-25 proteins and nucleic acids.

In a preferred embodiment, the USP-25 nucleic acid comprises a nucleic acid sequence having at least about 85%, more preferably at least about 90%, more preferably at least about 95%, more preferably at least about 98% identity to the nucleic acid sequence set forth in SEQ ID NO:1 or 3. In a preferred embodiment, the USP-25 nucleic acid comprises the nucleic acid sequence set forth in SEQ ID NO:1 or 3. In a preferred embodiment, the USP-25 nucleic acid encodes a USP-25 protein.

In a preferred embodiment, the USP-25 protein comprises an amino acid sequence encoded by a nucleic acid sequence having at least about 85%, more preferably at least about 90%, more preferably at least about 95%, more preferably at least about 98% identity to the nucleic acid sequence set forth in SEQ ID NO:1 or 3. In a preferred embodiment, the USP-25 protein comprises an amino acid sequence encoded by the nucleic acid sequence set forth in SEQ ID NO:1 or 3.

Also provided herein are USP-25 antisense nucleic acids which nucleic acids will hybridize under high stringency conditions to a USP-25 nucleic acid comprising the nucleic acid sequence set forth in SEQ ID NO:1 or 3. In a preferred embodiment, the USP-25 antisense nucleic acid inhibits expression of USP-25 protein encoded by USP-25 nucleic acid. In a preferred embodiment, the USP-25 antisense nucleic acid inhibits USP-25 protein activity. In a preferred embodiment, the USP-25 antisense nucleic acid has at least one activity possessed by a dominant negative USP-25 protein described herein.

In a preferred embodiment, the USP-25 protein comprises an amino acid sequence having at least about 85%, more preferably at least about 90%, more preferably at least about 95%, more preferably at least about 98% identity to the amino acid sequence set forth in SEQ ID NO:2 or 4. In a preferred embodiment, the USP-25 protein comprises the amino acid sequence set forth in SEQ ID NO:2 or 4. Preferably, the USP-25 protein also possesses one or more USP-25 bioactivities described herein.

A USP-25 protein of the present invention may be identified in several ways. "Protein" in this sense includes proteins, polypeptides, and peptides. A USP-25 protein may be identified by its association with a protein known to be involved in leukocyte activation. A USP-25 protein may be identified by homology to ubiquitin-specific peptidases. A USP-25 protein may be identified by possession of a conserved ubiquitin-specific peptidase domain, a ubiquitin associated domain, and a ubiquitin hydrolase domain. A USP-25 protein may be identified by possession of ubiquitin-specific peptidase activity. A USP-25 protein may be identified by possession of peptidase activity directed specifically at ubiquitin-like proteins, for example SMT3/SUMO and NEDD8/RUBY.

In one embodiment, the USP-25 protein has one or more of the following characteristics: ability to bind to SYK, UBC9, calcineurin, or ubiquitin conjugates thereof, or ubiquitin-like protein conjugates thereof; homology and/or identity to USP-25 isoform 1 (SEQ ID NO: 2) or USP-25 isoform 2 (SEQ ID NO: 4); homology to ubiquitin-specific peptidases (herein used interchangeably with ubiquitin isopeptidases, and ubiquitin-specific proteases); homology to peptidases specific for ubiquitin-like proteins such as SMT3/SUMO and NEDD8/RUBY; ubiquiin-sepcific peptidase activity; ubiquitin-like protein-specific peptidase activity; and the ability to modulate leukocyte and platelet activation as described herein. Homology and identity to ubiquitin-specific proteases and to USP-25 isoforms 1and 2 can be determined as described below. In one embodiment, homology and identity are determined by performing a Blastp search in Genbank's non-redundant protein database using default parameters. In another embodiment, homology and identity are determined using the following database and parameters: Database: Non-redundant GenBank CDS translations+PDB+SwissProt+Spupdate+PIR; Lambda of 0.316, K of 0.133 and H of 0; Gapped Lambda of 0.27, K of 0.047, and H of 4.94e-324; Matrix is BLOSUM62; Gap Penalities: Existence: 11, Extension: 1.

In a preferred embodiment, the USP-25 protein comprises the amino acid sequence set forth in SEQ ID NO:2 or 4. In a preferred embodiment, the USP-25 protein comprises a fragment of the amino acid sequence set forth in SEQ ID NO:2 or 4 and comprises a ubiquitin-specific peptidase domain. The characteristics described below can apply to any of the USP-25 proteins provided herein.

In a preferred embodiment, the USP-25 protein has amino acid sequence similarity to ubiquitin-specific proteases, ubiquitin isopeptidases, ubiquitin hydrolases, ubiquitin peptidases, and grammatical equivalents thereof, which enzymes remove ubiquitin from their substrates. In a further preferred embodiment, the USP-25 protein has a ubiquitin associated domain, a ubiquitin peptidase domain comprising a conserved cysteine and two conserved histidine residues, and a ubiquitin hydrolase domain. In a preferred embodiment, the USP-25 protein has ubiquitin specific peptidase activity. In another preferred embodiment, USP-25 protein has ubiquitin-like protein-specific peptidase activity, preferably directed at the SMT3/SUMO or NEDD8/RUBY ubiquitin-like proteins.

In a preferred embodiment, the USP-25 protein binds to SYK. In one aspect, the USP-25 protein binds to SYK in T cells. In one aspect, the USP-25 protein binds to SYK in B cells. In one aspect, the USP-25 protein binds to SYK in mast cells. In one aspect, the USP-25 protein binds to SYK in macrophages. In one aspect, the USP-25 protein binds to SYK in peripheral blood lymphocytes. In one aspect, the USP-25 protein binds to SYK in granulocytes. In one aspect, the USP-25 protein binds to SYK in platelets. In a preferred embodiment, the USP-25 protein will modulate SYK protein level or activity in leukocytes and platelets that express SYK protein. In a preferred embodiment, the USP-25 protein will modulate the activation of leukocytes and platelets that express SYK protein.

In a preferred embodiment, the USP-25 protein binds to ubiquitin-conjugated SYK protein. In one aspect, the USP-25 protein removes ubiquitin therefrom. In one aspect, the USP-25 protein modulates SYK protein tyrosine kinase activity.

In a preferred embodiment, the USP-25 protein binds to SYK protein conjugated to ubiquitin-like protein. In one aspect, the SUP-25 protein removes ubiquitin-like protein therefrom. In one aspect, the USP-25 protein modulates SYK protein tyrosine kinase activity.

In a preferred embodiment, the USP-25 protein binds to calcineurin and/or UBC9. In one aspect, the USP-25 protein binds to calcineurin and/or UBC9 in T cells. In one aspect, the USP-25 protein binds to calcineurin and/or UBC9 in B cells. In one aspect, the USP-25 protein binds to calcineurin and/or UBC9 in mast cells. In one aspect, the USP-25 protein binds to calcineurin and/or UBC9 in macrophages. In one aspect, the USP-25 protein binds to calcineurin and/or UBC9 in peripheral blood lymphocytes. In one aspect, the USP-25 protein binds to calcineurin and/or UBC9 in granulocytes. In one aspect, the USP-25 protein binds to calcineurin and/or UBC9 in platelets. In one aspect, the USP-25 protein modulates calcineurin and/or UBC9 level or activity. In a preferred embodiment, the USP-25 protein will modulate the activation of leukocytes and platelets that express UBC9 and/or calcineurin.

In a preferred embodiment, the USP-25 protein binds to ubiquitin-conjugated UBC9 and/or calcineurin protein. In one aspect, the USP-25 protein removes ubiquitin therefrom. In one aspect, the USP-25 protein modulates calcineurin phosphatase activity and/or UBC9 ubiquitin or ubiquitin-like protein conjugating activity.

In a preferred embodiment, the USP-25 protein binds to UBC9 and/or calcineurin conjugated to ubiquitin-like protein. In one aspect, the SUP-25 protein removes ubiquitin-like protein therefrom. In one aspect, the USP-25 protein modulates calcineurin phosphatase activity and/or UBC9 ubiquitin or ubiquitin-like protein conjugating activity.

Calcineurin is a known calcium/calmodulin sensitive phosphatase which is important in lymphocyte function and activation (for example, see Lewis, Annu. Rev. Immunol. 19:497–521, 2001; Stankunas et. al., Cold Spring Harb. Symp. Quant. Biol., 64:505–516, 1999). Methods for the determination of calcineurin activity are known (for example see Stankunas, supra; Baumgrass et. al., J. Biol. Chem. manuscript M103273200, 11 Oct. 2001).

UBC9 is a known ubiquitin conjugating enzyme which is capable of conjugating ubiquitin-like protein to target proteins and methods for determining UBC9 activity are known (for example see Schwarz et. al., Proc. Nat'l. Acad. Sci., 95:560–564, 1998).

In one embodiment, USP-25 nucleic acids or USP-25 proteins can be initially identified by substantial nucleic acid and/or amino acid sequence identity or similarity to the sequences provided herein. In a preferred embodiment, USP-25 nucleic acids or USP-25 proteins have sequence identity or similarity to the sequences provided herein as described below and one or more USP-25 bioactivities. Such sequence identity or similarity can be based upon the overall nucleic acid or amino acid sequence.

In a preferred embodiment, the USP-25 protein comprises an amino acid sequence having preferably greater than about 75% identity overall to the amino acid sequence set forth in SEQ ID NO:2 or 4, more preferably greater that about 80%, even more preferably greater than about 85% and most preferably greater than about 90%. In some embodiments the sequence identity will be as high as about 93, 95 or 98%.

In a preferred embodiment, the USP-25 protein comprises an amino acid sequence having at least about 90%, more preferably at least about 95%, more preferably at least about 98% identity to a portion of the amino acid sequence set forth in SEQ ID NO:2 or 4 and comprises a ubiquitin-specific peptidase domain.

In another preferred embodiment, a USP-25 protein has an overall sequence similarity to the amino acid sequence of SEQ ID NO:2 or 4 of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., *Methods in Enzymology*, 266: 460–480 (1996)]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the USP-25 protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

USP-25 proteins of the present invention may be shorter or longer than the amino acid sequence encoded by the nucleic acid sequences shown in SEQ ID NO:1 and 3. Thus, in a preferred embodiment, included within the definition of USP-25 proteins are portions or fragments of the amino acid sequences encoded by the nucleic acid sequences provided herein. In one embodiment herein, fragments of USP-25 proteins are considered USP-25 proteins if a) they share at least one antigenic epitope; b) have at least the indicated sequence identity; c) and preferably have USP-25 protein activity as further defined herein. In one embodiment, fragments of USP-25 proteins are considered USP-25 proteins if: a) they have at least the indicated sequence identity; and b) they possess a ubiquitin-specific peptidase domain. In some cases, where the sequence is used diagnostically, that is, when the presence or absence of USP-25 nucleic acid is determined, only the indicated sequence identity is required. The nucleic acids of the present invention may also be shorter or longer than the sequences in SEQ ID NO:1 and 3. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, USP-25 proteins can be made that are longer than those depicted in SEQ ID NO:2 and 4; for example, by the addition of epitope or purification tags, the addition of other fusion sequences, or the elucidation of additional coding and non-coding sequences. As described below, the fusion of a USP-25 peptide to a fluorescent protein, such as Blue Fluorescent Protein (BFP) or Green Fluorescent Protein (GFP), including those of Aquorea and Renilla species, is particularly preferred.

USP-25 proteins may also be identified as encoded by USP-25 nucleic acids which hybridize to the sequences depicted in SEQ ID NO:1 and 3 their complements, or fragments thereof or their complements, as outlined herein. Hybridization conditions are further described below.

In a preferred embodiment, when a USP-25 protein is to be used to generate antibodies, a USP-25 protein must share at least one epitope or determinant with the full length protein. By "epitope" or "determinant" herein is meant a portion of a protein which will generate and/or bind an antibody. Thus, in most instances, antibodies made to a smaller USP-25 protein will be able to bind to the full length protein. In a preferred embodiment, the epitope is unique; that is, antibodies generated to a unique epitope show little or no cross-reactivity. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies.

In a preferred embodiment, the antibodies to a USP-25 protein are capable of reducing or eliminating the biological function of the USP-25 proteins described herein, as is described below. That is, the addition of anti-USP-25 antibodies (either polyclonal or preferably monoclonal) to USP-25 proteins (or cells containing USP-25 proteins) may reduce or eliminate their ability to modulate leukocyte and platelet activation. Generally, at least a 25% decrease in activity is preferred, with at least about 50% being particularly preferred and about a 95–100% decrease being especially preferred.

The anti-USP-25 antibodies of the invention bind to USP-25 proteins. In a preferred embodiment, the antibodies specifically bind to USP-25 proteins. By "specifically bind" herein is meant that the antibodies bind to the protein with a binding constant in the range of at least $10^{-4}$–$10^{-6}$ $M^{-1}$, with a preferred range being $10^{-7}$–$10^{-9}$ $M^{-1}$. Antibodies are further described below.

In the case of a USP-25 nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. A USP-25 nucleic acid of the present invention comprises a nucleic acid sequence that preferably has greater than about 75% identity to the nucleic acid sequence set forth in SEQ ID NO:1 or 3, more preferably greater than about 80%, particularly greater than about 85% and most preferably greater than 90%. In some embodiments the sequence identity will be as high as about 93 to 95 or 98%.

In a preferred embodiment, a USP-25 nucleic acid encodes a USP-25 protein. As will be appreciated by those in the art, due to the degeneracy of the genetic code, an extremely large number of nucleic acids may be made, all of which encode the USP-25 proteins of the present invention. Thus, having identified a particular amino acid sequence, those skilled in the art could make any number of different nucleic acids, by simply modifying the sequence of one or more codons in a way which does not change the amino acid sequence of the USP-25 protein.

In one embodiment, the USP-25 nucleic acid is determined through hybridization studies. Thus, for example, nucleic acids which hybridize under high stringency conditions to the nucleic acid sequences shown in SEQ ID NO:1 and 3 or their complements, or fragments thereof or their complements, are considered USP-25 nucleic acids. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The USP-25 proteins and USP-25 nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the Figures also include the complement of the sequence. By the term "recombinant nucleic acid" herein is meant nucleic acid, originally formed in vitro, in general, by the manipulation of nucleic acid by endonucleases, in a form not normally found in nature. Thus an isolated USP-25 nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a USP-25 protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides USP-25 protein variants. These variants fall into one or more of three classes: substitutional, insertional or deletional variants. These variants ordinarily are prepared by site specific mutagenesis of nucleotides in the DNA encoding a USP-25 protein, using cassette or PCR mutagenesis or other techniques well known in the art, to produce DNA encoding the variant, and thereafter expressing the DNA in recombinant cell culture as outlined above. However, variant USP-25 protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the USP-25 protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed USP-25 protein variants screened for the optimal combination of desired activity. Techniques for making substitution mutations at predetermined sites in DNA having a known sequence are well known, for example, M13 primer mutagenesis and PCR mutagenesis. Screening of the mutants is done using assays of USP-25 protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the USP-25 protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the USP-25 proteins as needed. Alternatively, the variant may be designed such that the biological activity of the USP-25 protein is altered. For example, glycosylation sites may be altered or removed.

In a preferred embodiment, USP-25 variant proteins are provided which lack at least one USP-25 protein activity. In one aspect, the USP-25 variant protein lacks ubiquitin-specific peptidase activity. In one aspect, the USP-25 variant protein lacks ubiquitin-specific peptidase activity directed at ubiquitin conjugated SYK, calcineurin, or UBC9 protein. The USP-25 variant protein preferably has a substitution mutation whereby a conserved cysteine residue in the ubiquitin-specific peptidase catalytic domain corresponding to the conserved cysteine identified in the ubiquitin peptidase domain in FIG. 5 is replaced by an alternative residue, preferably methionine or serine.

In one aspect, the USP-25 variant protein lacks peptidase activity directed at ubiquitin-like proteins. In a preferred embodiment, the USP-25 variant protein lacks peptidase activity directed at SMT3/SUMO or NEDD8/RUBY. In one aspect, the USP-25 variant protein lacks peptidase activity directed at SYK, calcineurin, or UBC9 protein conjugated to ubiquitin-like protein. Preferably, the conjugated ubiquitin-like protein is SMT3/SUMO or NEDD8/RUBY.

In one aspect, such USP-25 variant proteins exhibit dominant negative activity, i.e. they inhibit the activity of wild-type USP-25 proteins in trans. In one aspect, the dominant negative USP-25 variant protein decreases SYK activity. In one aspect, the dominant negative USP-25 variant protein decreases SYK protein tyrosine kinase activity. Without being bound by theory, this decrease in SYK activity is due to an increase in the level of ubiquitination of SYK and a decrease in the amount or activity of SYK. In one aspect, the dominant negative USP-25 variant protein decreases basal lymphocyte activity. In one aspect, the dominant negative USP-25 variant protein inhibits or decreases lymphocyte activation, for example in response to stimuli including but not limited to BCR and TCR engagement. In one aspect, the dominant negative USP-25 variant protein inhibits or decreases mast cell activation, for example in response to stimuli including but not limited to antigen binding to surface IgE.

In one aspect, the dominant negative USP-25 variant protein modulates SYK activity. In one aspect, the dominant negative USP-25 variant protein modulates SYK protein tyrosine kinase activity.

In one aspect, the dominant negative USP-25 variant protein modulates calcineurin activity, preferably phosphatase activity. In one aspect, the dominant negative USP-25 variant protein modulates UBC9 activity, preferably ubiquitin or ubiquitin-like conjugating activity. Without being bound by theory, modulation of calcineurin and UBC9 activity by USP-25 is mediated by the proteolytic activity of USP-directed at ubiquitin or ubiquitin-like proteins conjugated to calcineurin and UBC9.

In one aspect, the dominant negative USP-25 variant protein modulates ubiquitination of SYK. In one aspect, the dominant negative USP-25 variant protein modulates conjugation of ubiquitin-like proteins to Syk. Preferably, conjugated ubiquitin-like proteins are the SMT3/SUMO or NEDD8/RUBY ubiquitin-like proteins.

In one aspect, the dominant negative USP-25 variant protein modulates ubiquitination of calcineurin. In one aspect, the dominant negative USP-25 variant protein modulates conjugation of ubiquitin-like protein to calcineurin. In another aspect, the dominant negative USP-25 variant protein modulates ubiquitination of a calcineurin target protein. In another aspect, the dominant negative USP-25 variant protein modulates conjugation of ubiquitin-like protein to a calcineurin target protein. Preferably, conjugated ubiquitin-like proteins are the SMT3/SUMO or NEDD8/RUBY ubiquitin-like proteins.

In one aspect, the dominant negative USP-25 variant protein modulates ubiquitination of UBC9. In one aspect, the dominant negative USP-25 variant protein modulates conjugation of ubiquitin-like protein to UBC9. In another aspect, the dominant negative USP-25 variant protein modulates ubiquitination of a UBC9 target protein. In another aspect, the dominant negative USP-25 variant protein modulates conjugation of ubiquitin-like protein to a UBC9 target protein. Preferably, conjugated ubiquitin-like proteins are the SMT3/SUMO or NEDD8/RUBY ubiquitin-like proteins.

In one embodiment, the dominant negative USP-25 variant protein inhibits activation of the NFAT gene promoter in lymphocytes.

In one embodiment, the dominant negative USP-25 variant protein inhibits activation of the immunoglobulin heavy chain gene promoter in lymphocytes.

Without being bound by theory, in one aspect the dominant negative USP-25 protein acts downstream of TCR, BCR, surface IgE, or other surface antigen receptor which will activate leukocytes or platelets. Without being bound by theory, in one aspect the dominant negative USP-25 protein acts downstream of release of intracellular calcium stores and downstream of the internalization of extracellular calcium. Without being bound by theory, the dominant negative USP-25 protein modulates calcineurin activity or acts downstream of calcineurin.

In a preferred embodiment, USP-25 variant proteins are provided which have constitutive ubiquitin peptidase activity and/or a higher specific activity (i.e. increased ubiquitin peptidase activity per molecule). An increase in activity may be due to a higher level catalytic efficiency (lower activation energy), a higher affinity for substrate, a lower level of inhibition, or a combination thereof.

In one aspect, such USP-25 variants increase SYK activity. In one aspect, such USP-25 variants increase SYK protein tyrosine kinase activity. Without being bound by theory, this increase in SYK activity is due to a decrease in the level of ubiquitination of SYK and an increase in the level or activity of SYK. In one aspect, such USP-25 variants increase basal lymphocyte activity. In one aspect, such USP-25 variant proteins potentiate or increase lymphocyte activation, for example in response to stimuli including but not limited to BCR and TCR engagement. In one aspect, such USP-25 variant proteins increase mast cell activation, for example in response to stimulation including but not limited to binding of antigen to surface IgE.

In a preferred embodiment, USP-25 variant proteins are provided which have constitutive ubiquitin-like protein specific peptidase activity and/or a higher specific activity (i.e. increased ubiquitin peptidase activity per molecule). An increase in activity may be due to a higher level catalytic efficiency (lower activation energy), a higher affinity for substrate, a lower level of inhibition, or a combination thereof.

In one aspect, such USP-25 variants increase SYK activity. In one aspect, such USP-25 variants increase SYK protein tyrosine kinase activity. Without being bound by theory, this increase in SYK activity is due to a decrease in the level of ubiquitin-like protein conjugation to SYK and an increase in the activity of SYK. In one aspect, such USP-25 variants increase basal lymphocyte activity. In one aspect, such USP-25 variant proteins potentiate or increase lymphocyte activation, for example in response to stimuli including but not limited to BCR and TCR engagement. In one aspect, such USP-25 variant proteins increase mast cell activation, for example in response to stimulation including but not limited to binding of antigen to surface IgE.

In one aspect, the USP-25 variants modulate calcineurin activity, preferably phosphatase activity. In one aspect, the SUP-25 protein variant modulates UBC9 activity, preferably ubiquitin or ubiquitin-like conjugating activity.

In one aspect, the USP-25 variant protein modulates ubiquitination of calcineurin. In one aspect, the USP-25 variant protein modulates conjugation of ubiquitin-like protein to calcineurin. In another aspect, the USP-25 variant protein modulates ubiquitination of a calcineurin target protein. In another aspect, the USP-25 variant protein modulates conjugation of ubiquitin-like protein to a calcineurin target protein. Preferably, conjugated ubiquitin-like proteins are the SMT3/SUMO or NEDD8/RUBY ubiquitin-like proteins.

In one aspect, the USP-25 variant protein modulates ubiquitination of UBC9. In one aspect, the USP-25 variant protein modulates conjugation of ubiquitin-like protein to UBC9. In another aspect, the USP-25 variant protein modulates ubiquitination of a UBC9 target protein. In another aspect, the USP-25 variant protein modulates conjugation of ubiquitin-like protein to a UBC9 target protein. Preferably, conjugated ubiquitin-like proteins are the SMT3/SUMO or NEDD8/RUBY ubiquitin-like proteins.

Covalent modifications of USP-25 polypeptides are included within the scope of this invention. One type of covalent modification includes reacting targeted amino acid residues of a USP-25 polypeptide with an organic derivatizing agent that is capable of reacting with selected side chains or the N-or C-terminal residues of a USP-25 polypeptide. Derivatization with bifunctional agents is useful, for instance, for crosslinking USP-25 to a water-insoluble support matrix or surface for use in the method for purifying anti-USP-25 antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the USP-25 polypeptide included within the scope of this invention comprises altering the native glycosylation pattern of the polypeptide. "Altering the native glycosylation pattern" is intended for purposes herein to mean deleting one or more carbohydrate moieties found in native sequence USP-25 polypeptide, and/or adding one or more glycosylation sites that are not present in the native sequence USP-25 polypeptide.

Addition of glycosylation sites to USP-25 polypeptides may be accomplished by altering the amino acid sequence thereof. The alteration may be made, for example, by the addition of, or substitution by, one or more serine or threonine residues to the native sequence USP-25 polypeptide (for O-linked glycosylation sites). The USP-25 amino acid sequence may optionally be altered through changes at the DNA level, particularly by mutating the DNA encoding the USP-25 polypeptide at preselected bases such that codons are generated that will translate into the desired amino acids.

Another means of increasing the number of carbohydrate moieties on the USP-25 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.*, pp. 259–306 (1981).

Removal of carbohydrate moieties present on the USP-25 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.*, 138:350 (1987).

Another type of covalent modification of USP-25 comprises linking the USP-25 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

USP-25 polypeptides of the present invention may also be modified in a way to form chimeric molecules comprising a USP-25 polypeptide fused to another, heterologous polypeptide or amino acid sequence. In one embodiment, such a chimeric molecule comprises a fusion of a USP-25 polypeptide with a tag polypeptide which provides an epitope to which an anti-tag antibody can selectively bind. In a preferred embodiment, such a tag is the "flag tag" described below. The epitope tag is generally placed at the amino-or carboxyl-terminus of the USP-25 polypeptide. The presence of such epitope-tagged forms of a USP-25 polypeptide can be detected using an antibody against the tag polypeptide. Also, provision of the epitope tag enables the USP-25 polypeptide to be readily purified by affinity purification using an anti-tag antibody or another type of affinity matrix that binds to the epitope tag. In an alternative embodiment, the chimeric molecule may comprise a fusion of a USP-25 polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7,6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*, 3(6):547–553 (1990)]. Other tag polypeptides include the Flag-peptide [Hopp et al., *BioTechnology*, 6:1204–1210 (1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an embodiment herein, USP-25 protein family members and USP-25 proteins from other organisms are cloned and expressed as outlined below. Thus, probe or degenerate polymerase chain reaction (PCR) primer sequences may be used to find other related USP-25 proteins from humans or other organisms. As will be appreciated by those in the art, particularly useful probe and/or PCR primer sequences include the unique areas of the USP-25 nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant USP-25 nucleic acid can be further-used as a probe to identify and isolate other USP-25 nucleic acids. It can also be used as a "precursor" nucleic acid to make modified or variant USP-25 nucleic acids and proteins.

Using the nucleic acids of the present invention which encode a USP-25 protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the USP-25 protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the USP-25 protein; for example, transcriptional and translational regulatory nucleic acid sequences from *Bacillus* are preferably used to express the USP-25 protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

USP-25 proteins of the present invention are produced by culturing a host cell transformed with an expression vector containing USP-25 nucleic acid encoding a USP-25 protein, under the appropriate conditions to induce or cause expression of the USP-25 protein. The conditions appropriate for USP-25 protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli*, *Bacillus subtilis*, SF9 cells, C129 cells, 293 cells, Neurospora, BHK, CHO, COS, and HeLa cells, fibroblasts, Schwanoma cell lines, immortalized mammalian myeloid and lymphoid cell lines.

In a preferred embodiment, the USP-25 proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for USP-25 protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, USP-25 proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of USP-25 protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the USP-25 protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli Streptococcus cremoris*, and *Streptococcus lividans*, among others.

The bacterial expression vectors are transformed into bacterial host cells using techniques well known in the art, such as calcium chloride treatment, electroporation, and others.

In one embodiment, USP-25 proteins are produced in insect cells. Expression vectors for the transformation of insect cells, and in particular, baculovirus-based expression vectors, are well known in the art.

In a preferred embodiment, USP-25 protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The USP-25 protein may also be made as a fusion protein, using techniques well known in the art. Thus, for example, for the creation of monoclonal antibodies, if the desired epitope is small, the USP-25 protein may be fused to a carrier protein to form an immunogen. Alternatively, the USP-25 protein may be made as a fusion protein to increase expression, or for other reasons. For example, when the USP-25 protein is a USP-25 peptide, the nucleic acid encoding the peptide may be linked to other nucleic acid for expression purposes. Similarly, USP-25 proteins of the invention can be linked to protein labels, such as green fluorescent protein (GFP), red fluorescent protein (RFP), blue fluorescent protein (BFP), yellow fluorescent protein (YFP), etc.

In one embodiment, the USP-25 nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the USP-25 protein is purified or isolated after expression. USP-25 proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the USP-25 protein may be purified using a standard anti-USP-25 antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the USP-25 protein. In some instances no purification will be necessary.

Once expressed and purified if necessary, the USP-25 proteins and nucleic acids are useful in a number of applications.

The nucleotide sequences (or their complement) encoding USP-25 proteins have various applications in the art of molecular biology, including uses as hybridization probes, in chromosome and gene mapping and in the generation of anti-sense RNA and DNA. USP-25 protein nucleic acid will also be useful for the preparation of USP-25 proteins by the recombinant techniques described herein.

The full-length native sequence USP-25 protein gene, or portions thereof, may be used as hybridization probes for a cDNA library to isolate other genes (for instance, those encoding naturally-occurring variants of USP-25 protein or USP-25 protein from other species) which have a desired sequence identity to the USP-25 protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the USP-25 protein gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the USP-25 protein gene of the present invention can be used to screen libraries of human cDNA, genomic DNA or mRNA to determine which members of such libraries the probe hybridizes.

Nucleotide sequences encoding a USP-25 protein can also be used to construct hybridization probes for mapping the gene which encodes that USP-25 protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode USP-25 protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a USP-25 protein can be used to clone genomic DNA encoding a USP-25 protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for the USP-25 protein transgene incorporation with tissue-specific enhancers. Transgenic animals that include a copy of a transgene encoding a USP-25 protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the USP-25 protein can be used to construct a USP-25 protein "knock out" animal which has a defective or altered gene encoding a USP-25 protein as a result of homologous recombination between the endogenous gene encoding a USP-25 protein and altered genomic DNA encoding a USP-25 protein introduced into an embryonic cell of the animal. For example, cDNA encoding a USP-25 protein can be used to clone genomic DNA encoding a USP-25 protein in accordance with established techniques. A portion of the genomic DNA encoding a USP-25 protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the USP-25 protein.

It is understood that the models described herein can be varied. For example, "knock-in" models can be formed, or the models can be cell-based rather than animal models.

Nucleic acid encoding the USP-25 polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429–4432 (1987); and Wagner et al., *Proc. Natl. Acad. Sci. USA* 87, 3410–3414 (1990). For review of gene marking and gene therapy protocols see Anderson et al., *Science* 256, 808–813 (1992).

In a preferred embodiment, the USP-25 proteins, nucleic acids, variants, modified proteins, cells and/or transgenics containing the said nucleic acids or proteins are used in screening assays. Identification of the USP-25 proteins provided herein permits the design of drug screening assays for compounds that modulate USP-25 protein binding, modulate USP-25 protein activity, modulate leukocyte and platelet activation, modulate ubiquitination of Syk, UBC9 or calcineurin, modulate conjugation of ubiquitin-like protein to Syk, UBC9 or calcineurin, and modulate SYK, UBC9 or calcineurin activity.

The assays described herein preferably utilize the human USP-25 protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative USP-25 proteins may be used, including C→M and C→S substitution mutant catalytically dead USP-25 variant proteins as outlined herein and alternatively referred to as dominant negative USP-25 variant protein.

In a preferred embodiment, the methods comprise combining a USP-25 protein and a candidate bioactive agent, and determining the binding of the candidate agent to the USP-25 protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind USP-25 protein, may be used. In a preferred embodiment, SYK is used as a positive control for binding to USP-25.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred, and 12 and 18 amino acids being most preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114: 1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties or small molecule chemical compositions, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In one embodiment of the methods described herein, portions of USP-25 proteins are utilized; in a preferred embodiment, portions having USP-25 activity as described herein are used. In a preferred embodiment, portions comprising a ubiquitin-specific peptidase domain are used. USP-25 activity is described further below and includes binding to SYK protein and ubiquitin-specific peptidase activity directed to ubiquitin-conjugated SYK protein. In a preferred embodiment, portions of USP-25 protein variants which lack ubiquitin-specific activity are used. In addition, the assays described herein may utilize either isolated USP-25 proteins or cells comprising the USP-25 proteins.

Generally, in a preferred embodiment of the methods herein, for example for binding assays, the USP-25 protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the USP-25 protein is bound to the support, and a candidate bioactive agent is added to the assay. Alternatively, the candidate agent is bound to the support and the USP-25 protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the USP-25 protein may be done in a number of ways. In a preferred embodiment, the candidate bioactive agent is labelled, and binding determined directly. For example, this may be done by attaching all or a portion of the USP-25 protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. USP-25 protein), such as an antibody, peptide, binding partner, ligand, etc. In a preferred embodiment, the competitor is SYK, UBC9 or calcineurin protein. In another embodiment, the competitor is SYK, UBC9 or calcineurin protein conjugated to ubiquitin or ubiquitin-like protein. Under certain circumstances, there may be competitive binding as between the bioactive agent and the binding moiety, with the binding moiety displacing the bioactive agent. This assay can be used to determine candidate agents which interfere with binding between USP-25 proteins and SYK, UBC9, or calcineurin protein. "Interference of binding" as used herein means that native binding of the USP-25 protein differs in the presence of the candidate agent. The binding can be eliminated or can be with a reduced affinity.

Therefore, in one embodiment, interference is caused by, for example, a conformational change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4° C. and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the USP-25 protein and thus is capable of binding to, and potentially modulating, the activity of the USP-25 protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the USP-25 protein with a higher affinity. Thus, if the candidate bioactive agent is labeled, the presence of the label on the support, coupled with a lack of competitor binding, may indicate that the candidate agent is capable of binding to the USP-25 protein.

In a preferred embodiment, the methods comprise differential screening to identity bioactive agents that are capable of modulating the activity of the USP-25 proteins. Such assays can be done with the USP-25 protein or cells comprising USP-25 protein. USP-25 protein may be recombinant USP-25 protein produced and collected as described herein, or may be a cell lysate from a cell comprising a USP-25 protein or a recombinant USP-25 protein. In one embodiment, the methods comprise combining an USP-25 protein and a competitor in a first sample. A second sample comprises a candidate bioactive agent, an USP-25 protein and a competitor. The binding of the competitor is determined for both samples, and a change, or difference in binding between the two samples indicates the presence of an agent capable of binding to the USP-25 protein and modulating its activity. That is, if the binding of the competitor is different in the second sample relative to the first sample, the agent is capable of binding to the USP-25 protein and modulating its activity.

Alternatively, a preferred embodiment utilizes differential screening to identify drug candidates that bind to the native USP-25 protein, but cannot bind to modified USP-25 proteins. The structure of the USP-25 protein may be modeled, and used in rational drug design to synthesize agents that interact with that site. Drug candidates that affect USP-25 bioactivity are also identified by screening drugs for the ability to either enhance or reduce the activity of the protein. In a preferred embodiment, drugs are screened for their ability to inhibit wildtype USP-25 activity in a manner similar to the dominant negative effects of a C→S or C→M catalytically dead USP-25 variant protein as described herein.

In a preferred embodiment, candidate drugs are screened for their ability to bind to a USP-25 protein possessing ubiquitin specific protease activity or ubiquitin-like protein specific protease activity and their inability to bind to a USP-25 variant lacking such activity.

In a preferred embodiment, candidate drugs are screened for their ability to bind to a USP-25 variant lacking ubiquitin-specific protease activity or ubiquitin-like protein specific protease activity and their inability to bind to a USP-25 protein possessing such activity.

In another embodiment, candidate drugs are screened for their ability to bind to a USP-25 protein that is capable of binding to a USP-25 binding partner and their inability to bind to a USP-25 protein that is not capable of such binding.

In another embodiment, candidate drugs are screened for their ability to bind to a USP-25 protein that is not capable of binding to a USP-25 binding partner and their inability to bind to a USP-25 protein that is capable of such binding.

In another embodiment, candidate drugs are screened for their ability to bind to a USP-25 protein that is capable of removing ubiquitin from ubiquitin-conjugated target protein, and their inability to bind to a USP-25 protein that is not capable of removing ubiquitin from ubiquitin-conjugated target protein.

In another embodiment, candidate drugs are screened for their ability to bind to a USP-25 protein that is not capable of removing ubiquitin from ubiquitin-conjugated target protein, and their inability to bind to a USP-25 protein that is capable of removing ubiquitin from ubiquitin-conjugated target protein.

In another embodiment, candidate drugs are screened for their ability to bind to a USP-25 protein that is capable of removing ubiquitin-like protein from conjugated target protein, and their inability to bind to a USP-25 protein that is not capable of such removal.

In another embodiment, candidate drugs are screened for their ability to bind to a USP-25 protein that is not capable of removing ubiquitin-like protein from conjugated target protein, and their inability to bind to a USP-25 protein that is capable of such removal.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce nonspecific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of a USP-25 protein may also be done. In a preferred embodiment, methods for screening for a bioactive agent capable of modulating the activity of a USP-25 protein comprise the steps of adding a candidate bioactive agent to a sample of a USP-25 protein (or a cell comprising a USP-25 protein) and determining an alteration in the biological activity of the USP-25 protein. A sample of a USP-25 protein may be obtained by recombinantly producing and collecting USP-25 protein, as described herein, or by obtaining a cell lysate from a cell comprising a USP-25 protein or a recombinant USP-25 protein by means known in the art. "Modulating the activity of a USP-25 protein" includes an increase in activity, a decrease in activity, or a change in the type or kind of activity present. Thus, in this embodiment, the candidate agent may bind to a USP-25 protein (although this may not be necessary), and should alter its biological or biochemical activity as defined herein. The methods include both in vitro screening methods, as are generally outlined above, and in vivo screening of cells for alterations in the presence, cellular distribution, subcellular distribution, activity or amount of USP-25 protein. In vitro assays may be performed using cell lysates following in vivo manipulations involved in screens.

By "USP-25 protein activity" or grammatical equivalents herein is meant at least one of the USP-25 protein's biological activities, including, but not limited to, modulation of leukocyte activation; modulation of platelet activation; modulation of lymphocyte activation; modulation of B lymphocyte activation by BCR stimulation; modulation of T lymphocyte activation by TCR stimulation; modulation of mast cell activation by stimulation of surface IgE; modulation of B cell differentiation; modulation of lymphocyte proliferation; modulation of IgM, IgG induction in B lymphocytes; modulation of immunoglobulin heavy chain gene promoter activity in lymphocytes; modulation of NFAT gene promoter activity in lymphocytes; modulation of immunoglobulin secretion by B lymphocytes; modulation of cytokine production in leukocytes; modulation of surface protein expression including CD23, CD69, CD80 and CD 86 in lymphocytes; binding to SYK, UBC9 and calcineurin; binding to ubiquitinated SYK, UBC9 and calcineurin; binding to SYK, UBC9 and calcineurin protein conjugated to ubiquitin-like protein; ubiquitin-specific peptidase activity; ubiquitin-like protein specific peptidase activity; modulation of SYK, UBC9 and calcineurin activity; modulation of SYK, UBC9 and calcineurin protein levels.

In a preferred embodiment, the activity of the USP-25 protein is decreased; in another preferred embodiment, the activity of the USP-25 protein is increased. Thus, bioactive agents that are antagonists are preferred in some embodiments, and bioactive agents that are agonists are preferred in other embodiments.

In a preferred embodiment, the invention provides methods for screening for bioactive agents capable of modulating the activity of a USP-25 protein. The methods comprise adding a candidate bioactive agent, as defined above, to a cell comprising a USP-25 protein. The cell contains a recombinant nucleic acid that encodes an USP-25 protein that is expressed in the cell. In a preferred embodiment, a library of candidate agents are tested on a plurality of cells. Preferred cell types include Ig(+) B cell lines, including the CL-01, LA350, and CA46 cell lines. T cell lines are also preferred.

Screening for agents that modulate B cell activation and T cell activation may also be done. In one aspect, the method involves screening for an agent capable of binding to USP-25 protein using assays provided herein. In one aspect, the method involves screening for an agent capable of modulating USP-25 binding using assays provided herein. In one aspect, the method involves screening for an agent that will modulate USP-25 activity using assays provided herein.

In some embodiments, the methods involve determining lymphocyte activation. As will be appreciated, lymphocyte activation as well as non-lymphocyte leukocyte activation and platelet activation can be determined in a number of ways. It will be appreciated that mechanisms of leukocyte activation and methods for determining activation are known (see for example Kay, Immunol. Invest. 17:679–705, 1988; Lukacs et. al., Chem. Immunol. 72:102–120,1999; Metcalf et. al., Physiol. Rev. 77:1033–1079, 1997; Hematol. Oncol. Clin. North Am. 4:1–26, 1990; Brass et. al., Adv. Exp. Med. Biol., 344:17–36, 1993; Brass et. al., Thromb. Haemost., 70:217–223, 1993; *Cellular and Molecular Immunology*, Abbas et. al., W. B. Saunders, ISBN 0–7216–3032–4, Chapters 7, 9, 12, and 14).

In one embodiment, indicators of lymphocyte activation are used. There are a number of parameters that may be evaluated or assayed to determine lymphocyte activation, including, but not limited to, immunoglobulin heavy chain gene promoter activity, NFAT gene promoter activity, Ig secretion, IgG and IgM production, lymphocyte proliferation, expression cell surface markers correlated with lymphocyte activation, cytokine production, release of calcium from intracellular stores, amount of SYK protein, level of SYK protein ubiquitination, SYK protein tyrosine kinase activity, and ubiquitin specific protease activity directed to ubiquitin-conjugated SYK protein. These parameters may be assayed and used as indicators to evaluate the effect of candidate drug agents on lymphocyte activation. In this manner, rapid, accurate screening of candidate agents may be performed to identify agents that modulate lymphocyte activation.

In one aspect, the assays include exposing lymphocytes comprising recombinant USP-25 protein to a T-cell or B-cell activation agent that will induce T-cell or B-cell activation in the absence of candidate agent and recombinant USP-25 protein. Alternatively, the cells may be exposed to conditions that normally result in T-cell and B-cell activation. The effect of the candidate agent on T-cell and B-cell activation is then evaluated. Preferred activation agents include anti-IgM antibody and C308 (anti-Ig's).

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. The cells may be in any cell phase, either synchronously or not, including M, G1, S, and G2. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc. More preferable cell types include Jurkat cells and the Ig(+) and IgM secreting B cell lines CL-01, LA350 and CA46.

Preferred cell surface markers in the present invention exhibit low background expression in the absence of lymphocyte activation. Especially preferred cell surface markers include CD23, CD69, CD80, CD86.

Agents that recognize such surface molecules (e.g. antibodies) can be used as an affinity ligand, and attached to a solid support such as a bead, a surface, etc., and used to pull out cells that are undergoing T-cell and B-cell activation. Similarly, these agents can be coupled to a fluorescent dye such as PerCP, and then used as the basis of a fluorescence-activated cell sorting (FACS) separation.

FACS analysis can be used in conjunction with antibodies recognizing lymphocyte surface markers that are correlated with lymphocyte activation. FACS analysis is used to determine expression of these markers in unstimulated and stimulated lymphocytes which may additionally or alternatively be exposed to cytokines.

Immunoglobulin heavy chan gene promoter activity and NFAT gene promoter activity can be measured using lymphocyte clones comprising an immunoglobulin heavy chain or NFAT promoter operably fused to a reporter gene. For example, a surface Ig(+), IgM secreting B cell line such as the CL-01, CA46, or LA350 cell line is transfected with a construct comprising GFP/2a/TK fusion under the control of an immunoglobulin heavy chain promoter, Eμ and 3'α enhancer elements. Stable transfectants (referred to herein as immunoglobulin heavy chain reporter cell lines) are selected and maintained in gancyclovir. Preferred immunoglobulin heavy chain reporter cell lines for use in the present invention exhibit low background GFP expression and strong basal activity and/or inducible activity in the presence of positive control. Such cell lines can be generated with the use of retroviral constructs.

Immunoglobulin heavy chain reporter cell lines are transfected with USP-25 nucleic acids which are expressed in the cell lines. A FACS machine may be used to determine reporter gene (GFP) expression in USP-25-transfected immunoglobulin heavy chain cell lines, comparing reporter gene expression in cells exposed to anti-Ig and not exposed to anti-Ig. In one embodiment, USP-25 protein affects basal reporter gene expression. In a preferred embodiment, reporter gene expression is determined in the presence and absence of candidate bioactive agents in immunoglobulin heavy chain cell lines stimulated and not stimulated with anti-Ig. In another preferred embodiment, reporter gene expression is determined in the presence and absence of candidate bioactive agents as they are tested for their ability to modulate the effect of USP-25 protein on basal reporter gene expression, i.e. absent BCR or TCR stimulation.

SYK protein determination may be done using standard protein preparation, immunoprecipitation, and Western blotting techniques. For example, Peters et al. disclose SYK immunoprecipitation and immunoblotting (JBC, 271:4755–4762, 1996, incorporated herein in its entirety by reference).

The determination of ubiquitin-conjugated SYK protein may be done using standard protein preparation, immunoprecipitation, and Western blotting techniques in conjunction with standard ubiquitin determining techniques which include Western blotting. Such techniques are described herein. In addition, for example, a method for ubiquitinated protein determination is disclosed by Okada et al., Journal of Biological Chemistry 274:23787–23793, 1999, incorporated herein in its entirety by reference.

Alternatively, an in vitro assay using labeled ubiquitin and determining the amount of label associated with SYK protein may be done to determine the level of SYK protein ubiquitination in a screen for bioactive agents capable of altering the level of SYK protein ubiquitination. Particularly preferred are high thoughput assays screening agents for their ability to alter the level of SYK ubiquitination. In one embodiment, labeled ubiquitin or polyubiquitin is combined with a SYK protein as well as a ubiquitin activating enzyme, a ubiquitin conjugating enzyme, and optionally a ubiquitin ligase, under conditions which provide for the ubiquitination of SYK protein, and therefore requiring that either the ubiquitin conjugating enzyme or the ubiquitin ligase be capable of conjugating ubiquitin to SYK. A ubiquitin-conjugated ubiquitin conjugating enzyme or a ubiquitin-conjugated ubiquitin ligase wherein ubiquitin is labeled may optionally replace ubiquitin, polyubiquitin, and ubiquitin activating enzyme in the combination. Also combined is a USP-25 protein and a candidate agent. The proteins combined herein may be recombinantly produced and collected proteins, purified proteins, or may simply be present in a cell lysate that is used in the assay. The amount of label associated with SYK protein is determined, for example in a high throughput screen using a scintillation counter to determine the amount of radioactively labeled ubiquitin associated with SYK protein in a sample. Alternatively, the amount of free labeled ubiquitin may be determined. The level of ubiquitin association with SYK in the presence and absence of candidate agent is determined to identify an agent as being able to increase or decrease the level of SYK protein ubiquitination.

Alternatively, SYK protein may be labeled and the amount of SYK protein associated with ubiquitin may be determined in such an assay.

In vitro assays for determining the inhibition of protein ubiquitination have been described. For example, U.S. Pat. No. 5,968,761 issued to Rolfe et al. sets forth in vitro methods for identifying inhibitors that prevent ubiquitination of a target protein. In addition, U.S. Pat. No. 5,976,849 issued to Hustad et al. provides similar methods.

In another embodiment, a ubiquitin-conjugated SYK protein wherein ubiquitin is labeled, is combined with a USP-25 protein and a candidate agent. The amount of ubiquitin association with SYK is compared in the presence and absence of candidate agent to identify an agent as being and able to increase or decrease the level of SYK protein ubiquitination.

Alternatively, SYK protein may be labeled and the amount of SYK protein associated with ubiquitin may be determined in such an assay.

SYK protein tyrosine kinase assays may be done using methods known in the art. For example Tartare-Deckert et al. disclose a method for determining SYK protein tyrosine kinase activity using the protein "VAV" as a SYK protein tyrosine kinase substrate (J. Biol. Chem., Mar. 21, 2001).

USP-25 binding to SYK may be determined using standard protein preparation, immunoprecipitation, and Western blotting techniques, as demonstrated in the present examples and discussed herein.

Ubiquitin-specific protease activity directed to ubiquitin-conjugated SYK protein may be assayed using standard protein preparation and immunoprecipitation techniques in conjunction with standard ubiquitin determining techniques which include Western blotting. Optionally, these assays may involve the production and collection of recombinant SYK protein as is known, using methods described herein in reference to recombinant USP-25 protein production. For example, a method for the determination of ubiquitin removal from a specific protein substrate is disclosed by Lin et al., Molecular and Cellular Biology, 20:6568–6578, 2000, incorporated herein in its entirety by reference. Preferably, the determination of ubiquitin-specific protease activity directed to ubiquitin-conjugated SYK protein is assayed using an in vitro assay on cell lysates to determine the amount of labeled ubiquitin associated with SYK protein or the amount of labeled SYK protein associated with ubiquitin, as discussed above.

Similar to the foregoing assays, assays for ubiquitin-like protein conjugated SYK may be done. Similarly, screens for agents that modulate SYK protein conjugation to ubiquitin-like protein may be done. Similarly, ubiquitin-like protein specific peptidase activity may be determined. Preferably, such methods involve the use of labeled SMT3/SUMO or labeled NEDD8/RUBY, or SMT3/SUMO or NEDD8/RUBY immunodetection.

Similarly, assays for ubiquitin conjugation calcineurin and UBC9 may be done. Similarly, assays for ubiquitin-like protein conjugation to calcineurin and UBC9 may be done. Similarly, assays for such conjugation to other USP-25 target proteins may be done.

Similarly, screens for agents that modulate such conjugation to calcineurin, UBC9, or other USP-25 target protein may be done. Similarly, screens involving the determination of calcineurin or UBC9 activity may be done. Methods for the determination of calcineurin activity are known (for example see Stankunas, supra; Baumgrass et. al., J. Biol. Chem. manuscript M103273200, 11 Oct. 2001), and methods for determining UBC9 activity are known (for example see Schwarz et. al., Proc. Nat'l. Acad. Sci., 95:560–564, 1998).

Release of intracellular calcium stores may be assayed using membrane permeant vital calcium sensing fluorescent dyes, as are well known in the art.

A preferred embodiment utilizes a cell proliferation assay. For example, B cells proliferate when activated. By "proliferation assay" herein is meant an assay that allows the determination that a cell population is either proliferating, i.e. replicating, or not replicating.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

The rate of loss of fluorescence is indicative of the rate of proliferation. An increase in proliferation rate above that of unstimulated cells is indicative of B cell activation.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook; chapter 15 in particular.

In general, inclusion dyes are provided to the cells at a concentration ranging from about 100 ng/ml to about 5 μg/ml, with from about 500 ng/ml to about 1 μg/ml being preferred. A wash step may or may not be used. In a preferred embodiment, a candidate bioactive agent is combined with the cells as described herein. The cells and the inclusion dye are incubated for some period of time, to allow cell division and thus dye dilution.

Without being bound by theory, it is recognized herein that USP-25 proteins are involved in the regulation of signal transduction in lymphocytes. Particularly, USP-25 proteins are recognized herein as being critical regulators of B cell and T-cell activation. As discussed above, the activation of specific signaling pathways in lymphocytes determines the quality, magnitude, and duration of immune responses. In transplantation, acute and chronic inflammatory diseases, and autoimmunity, it is these pathways that are responsible for the induction, maintenance and exacerbation of undesirable lymphocyte responses.

In a preferred embodiment, without being bound by theory, the present invention provides USP-25 proteins and nucleic acids, as well as agents that bind to them and/or modulate their activity, including and preferably small molecule chemical compositions as discussed herein, which are useful in the treatment of acute and chronic inflammatory diseases and autoimmune diseases, as well as in the treatment of a host receiving a transplant.

In a preferred embodiment, without being bound by theory, the present invention provides USP-25 proteins and nucleic acids, as well as agents that bind to them and/or modulate their activity, including and preferably small molecule chemical compositions as discussed herein, which are useful in the treatment of physiological states that lead to the presentation of some or all symptoms characteristic of acute inflammatory disease, chronic inflammatory disease, autoimmune disease, or response to transplantation.

In a preferred embodiment, without being bound by theory, the present invention provides USP-25 proteins and nucleic acids, as well as agents that bind to them and/or modulate their activity, including and preferably small molecule chemical compositions as discussed herein, which are useful as prophylactics directed to acute inflammatory disease, chronic inflammatory disease, autoimmune disease, and response to transplantation.

In a preferred embodiment, without being bound by theory, the present invention provides USP-25 proteins and nucleic acids, as well as agents that bind to them and/or modulate their activity, including and preferably small molecule chemical compositions as discussed herein, which are useful as prophylactics directed to physiological states that lead to the presentation of some or all symptoms characteristic of acute inflammatory disease, chronic inflammatory disease, autoimmune disease, or response to transplantation.

Without being bound by theory, it is recognized herein that USP-25 proteins play an important role in the regulation of lymphocyte proliferation. Accordingly, it is recognized herein that dysfunction or dysregulation of USP-25 proteins and nucleic acids, as well as USP-25 signaling pathways and molecules associated with USP-25 proteins and nucleic acids, can lead to deregulated cell proliferation, the hallmark of cancer. As USP-25 and the USP-25 interacting non-receptor tyrosine kinase protein SYK are both expressed in B and T cells in vivo, it is recognized herein, without being bound by theory, that USP-25 dysfunction or dysregulation results in B cell and T cell cancers (including lymphomas and leukemias).

Without being bound by theory, the present invention provides USP-25 proteins and nucleic acids, as well as agents that bind to them and/or modulate their activity, including and preferably small molecule chemical compositions as discussed herein, which are useful in the treatment of T cell and B cell cancers.

It is recognized in the art that signaling pathways involved in the regulation of cell proliferation frequently participate in, directly or indirectly, the regulation of cell survival and programmed cell death. It is further recognized in the art that the dysregulation of mechanisms of programmed cell death can lead to cancer, particularly in lymphocytes. For example, overexpression of Bcl-2, which is involved in normal cell survival through the inhibition of apoptosis, is thought to be responsible for the survival of excessive numbers of lymphocytes in a form of lymphoma.

Without being bound by theory, the present invention provides USP-25 proteins and nucleic acids, as well as agents binding to them or modulating their activity, including and preferably small molecule chemical compositions as discussed herein, which are useful in the treatment of disorders involving T cell and B cell survival and programmed cell death including cancer.

The proteins and nucleic acids provided herein can also be used for screening purposes wherein the protein-protein interactions of the USP-25 proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463. a preferred system is described in Ser. No. 09/050,863, filed Mar. 30, 1998 and Ser. No. 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding a USP-25 protein or a portion thereof, and the other encodes a test candidate. Only if the two expression products bind to one another will an indicator, such as a fluorescent protein, be expressed. Expression of the indicator indicates when a test candidate binds to the USP-25 protein, and identifies the candidate as being part of a T cell or B cell USP-25 signaling pathway. A test candidate so identified may then be used as bait to identify binding proteins that are also identified as being part of a T cell or B cell USP-25 signaling pathway. Additionally, USP-25 proteins may be used to identify new baits, or agents that bind to USP-25 proteins. Additionally, the two-hybrid system can be used wherein a test candidate is added in addition to the bait and the USP-25 protein encoding nucleic acids to determine agents which interfere with the binding of bait, such as SYK, to the USP-25 protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Expression in various cell types, and assays for USP-25 activity are described above. The activity assays can be performed to confirm the activity of USP-25 proteins which have already been identified by their sequence identity/similarity to USP-25, as well as to further confirm the activity of lead compounds identified as modulators of USP-25 activity.

The components provided herein for the assays provided herein may also be combined to form kits. The kits can be based on the use of the protein and/or the nucleic acid encoding the USP-25 proteins.

In one embodiment, other components are provided in the kit. Such components include one or more of packaging, instructions, antibodies, and labels. Additional assays such as those used in diagnostics are further described below.

In this way, bioactive agents are identified. Compounds with pharmacological activity are able to enhance or interfere with the activity of the USP-25 protein. The compounds having the desired pharmacological activity may be administered in a physiologically acceptable carrier to a host, as further described below.

The present discovery relating to the role of USP-25 proteins in leukocytes thus provides methods for inducing or preventing leukocyte activation, preferably lymphocyte activation. In a preferred embodiment, the USP-25 proteins, and particularly USP-25 protein fragments, are useful in the study or treatment of conditions which involve dysfunction or dysregulation of USP-25 protein activity, i.e. to diagnose, treat or prevent USP-25 associated disorders. Thus, "USP-25 associated disorders" or "disease states" or "physiological states associated with USP-25 dysfunction or dysregulation" include conditions involving insufficient, excessive, and inappropriate lymphocyte activation.

Thus, in one embodiment, methods for regulating lymphocyte activation in cells or organisms are provided. In one embodiment, the methods comprise administering to a cell or individual in need thereof, a USP-25 protein in a therapeutic amount. Alternatively, an anti-USP-25 antibody that reduces or eliminates the biological activity of the endogenous USP-25 protein is administered. Alternatively and preferably a USP-25 dominant negative protein variant is administered. In another preferred embodiment, a bioactive agent as identified by the methods provided herein is administered. In a further preferred embodiment, such an agent is a small molecule chemical composition which inhibits USP-25 activity. Alternatively, the methods comprise administering to a cell or individual a recombinant nucleic acid encoding an USP-25 protein. In one embodiment, nucleic acid encoding a USP-25 dominant negative variant protein is administered. In another embodiment, a USP-25 antisense nucleic acid is administered.

In one embodiment, the activity of USP-25 is increased. As will be appreciated by those in the art, this may be accomplished in any number of ways. In a preferred embodiment, the activity of USP-25 is increased by increasing the amount of USP-25 in the cell, for example by overexpressing the endogenous USP-25 or by administering a gene encoding a USP-25 protein, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety.

In one embodiment, the activity of USP-25 is decreased. As will be appreciated by those in the art, this may be accomplished in any number of ways. In a preferred embodiment, the activity of USP-25 is decreased by decreasing the amount of USP-25 mRNA in the cell, for example by expressing USP-25 antisense RNA. Alternatively, endogenous USP-25 activity is decreased by administering a dominant negative USP-25 protein or a gene encoding a dominant negative USP-25 protein. Alternatively, endogenous USP-25 activity is decreased by administering anti-USP-25 antibody or a gene encoding anti-USP-25 antibody or an epitope recognizing portion thereof. Known gene-therapy techniques may be used to administer these agents. In a preferred embodiment, the gene therapy techniques involve incorporation of the exogenous gene into the host genome using enhanced homologous recombination (EHR), for example as described in PCT/US93/03868, hereby incorporated by reference in its entirety.

Without being bound by theory, it appears that USP-25 protein is an important protein in leukocyte activation, particularly lymphocyte activation. Accordingly, disorders based on mutant or variant USP-25 genes may be determined. In one embodiment, the invention provides methods for identifying cells containing variant USP-25 genes comprising determining all or part of the sequence of at least one endogenous USP-25 gene in a cell. As will be appreciated by those in the art, this may be done using any number of sequencing techniques. In a preferred embodiment, the invention provides methods of identifying the USP-25 genotype of an individual comprising determining all or part of the sequence of at least one USP-25 gene of the individual. This is generally done in at least one tissue of the individual, and may include the evaluation of a number of tissues or different samples of the same tissue. The method may include comparing the sequence of the sequenced USP-25 gene to a known USP-25 gene, i.e. a wild-type gene.

The sequence of all or part of the USP-25 gene can then be compared to the sequence of a known USP-25 gene to determine if any differences exist. This can be done using any number of known sequence identity programs, such as Bestfit, etc. In a preferred embodiment, the presence of a difference in the sequence between the USP-25 gene of the patient and the known USP-25 gene is indicative of a disease state or a propensity for a disease state.

In one embodiment, the invention provides methods for diagnosing a USP-25 related condition in an individual. The methods comprise measuring the activity of USP-25 in a tissue from the individual or patient, which may include a measurement of the amount or specific activity of a USP-25 protein. This activity is compared to the activity of USP-25 from either an unaffected second individual or from an unaffected tissue from the first individual. When these activities are different, the first individual may be at risk for a USP-25 associated disorder. In this way, for example, monitoring of various disease conditions may be done, by monitoring the absolute USP-25 activity in a sample or the specific activity of a USP-25 protein from a sample. Similarly, activity levels may correlate with prognosis.

In one aspect, the expression levels of USP-25 protein genes are determined in different patient samples or cells for which either diagnosis or prognosis information is desired. Gene expression monitoring is done on genes encoding USP-25 proteins. In one aspect, the expression levels of USP-25 protein genes are determined for different cellular states, such as normal cells and cells undergoing apoptosis or transformation. By comparing USP-25 protein gene expression levels in cells in different states, information including both up- and down-regulation of USP-25 protein genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising sets of important USP-25 protein genes, such as those of the present invention, which can then be used in these screens. These methods can also be done on the protein basis; that is, protein expression levels of the USP-25 proteins can be evaluated for diagnostic purposes or to screen candidate agents. In addition, the USP-25 protein nucleic acid sequences can be administered for gene therapy purposes, including the administration of antisense nucleic acids, or the USP-25 proteins administered as therapeutic drugs.

USP-25 protein sequences bound to biochips include both nucleic acid and amino acid sequences as defined above. In a preferred embodiment, nucleic acid probes to USP-25 protein nucleic acids (both the nucleic acid sequences having the sequences outlined in the Figures and/or the complements thereof) are made. The nucleic acid probes attached to the biochip are designed to be substantially complementary to the USP-25 protein nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology 14:1675–1680 (1996), hereby expressly incorporated by reference. Other techniques include, but are not limited to, quantitative reverse transcriptase PCR, Northern analysis and RNase protection.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the USP-25 protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an USP-25 protein is detected by binding the digoxygenin with an anti-digoxygenin secondary antibody and developed with nitro blue tetrazolium and 5-bromo4-chloro-3-indoyl phosphate.

In another preferred method, expression of USP-25 protein is determined using in situ imaging techniques employing antibodies to USP-25 proteins. In this method cells are contacted with from one to many antibodies to the USP-25 protein(s). Following washing to remove non-specific antibody binding, the presence of the antibody or antibodies is detected. In one embodiment the antibody is detected by incubating with a secondary antibody that contains a detectable label. In another method the primary antibody to the USP-25 protein(s) contains a detectable label. In another preferred embodiment each one of multiple primary antibodies contains a distinct and detectable label. This method finds particular use in simultaneous screening for a plurality of USP-25 proteins. The label may be detected in a fluorometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblotting (Western blotting), immunoprecipitation, BIACORE technology, and the like.

In one embodiment, the USP-25 proteins of the present invention may be used to generate polyclonal and monoclonal antibodies to USP-25 proteins, which are useful as described herein. Similarly, the USP-25 proteins can be coupled, using standard technology, to affinity chromatography columns. These columns may then be used to purify USP-25 antibodies. In a preferred embodiment, the antibodies are generated to epitopes unique to the USP-25 protein; that is, the antibodies show little or no cross-reactivity to other proteins. These antibodies find use in a number of applications. For example, the USP-25 antibodies may be coupled to standard affinity chromatography columns and used to purify USP-25 proteins as further described below. The antibodies may also be used as blocking polypeptides, as outlined above, since they will specifically bind to the USP-25 protein.

The anti-USP-25 protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the USP-25 protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-USP-25 protein antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the USP-25 protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp.

59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against USP-25 protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-USP-25 protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature* 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.* 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwil al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

Bispecific antibodies are monoclonal, preferably human or humanized, antibodies that have binding specificities for at least two different antigens. In the present case, one of the binding specificities is for the USP-25 protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-USP-25 protein antibodies of the invention have various utilities. For example, anti-USP-25 protein antibodies may be used in diagnostic assays for an USP-25 protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-USP-25 protein antibodies also are useful for the affinity purification of USP-25 protein from recombinant cell culture or natural sources. In this process, the antibodies against USP-25 protein are immobilized on a suitable support, such a Sephadex resin or filter paper, using methods well known in the art. The immobilized antibody then is contacted with a sample containing the USP-25 protein to be purified, and thereafter the support is washed with a suitable solvent that will remove substantially all the material in the sample except the USP-25 protein, which is bound to the immobilized antibody. Finally, the support is washed with another suitable solvent that will release the USP-25 protein from the antibody.

The anti-USP-25 protein antibodies may also be used in treatment. In one embodiment, the genes encoding the antibodies are provided, such that the antibodies bind to and modulate the USP-25 protein within the cell.

In one embodiment, a therapeutically effective dose of an USP-25 protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for USP-25 protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the USP-25 protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100% wt.

The pharmaceutical compositions of the present invention comprise an USP-25 protein, agonist or antagonist (including antibodies and bioactive agents as described herein, most preferably small molecule chemical compositions as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of USP-25 protein related disorders with an antibody raised against a USP-25 protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an USP-25 protein antigen to which antibodies are raised. As appreciated by one of ordinary skill in the art, the USP-25 protein antigen may be provided by injecting an USP-25 protein against which antibodies are desired to be raised into a recipient, or contacting the recipient with an USP-25 protein nucleic acid, capable of expressing the USP-25 protein antigen, under conditions for expression of the USP-25 protein antigen.

In a preferred embodiment, a therapeutic compound is conjugated to an antibody, preferably an USP-25 protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis, cancer USP-25 protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against USP-25 proteins, or binding of a radionuclide to a chelating agent that has been covalently attached to the antibody.

In a preferred embodiment, USP-25 protein genes are administered as DNA vaccines, either single nucleic acids or combinations of USP-25 protein genes. Naked DNA vaccines are generally known in the art; see Brower, Nature Biotechnology 16:1304–1305 (1998). Methods for the use of nucleic acids as DNA vaccines are well known to one of ordinary skill in the art, and include placing an USP-25 protein gene or portion of an USP-25 protein nucleic acid under the control of a promoter for expression in a patient. The USP-25 protein gene used for DNA vaccines can encode full-length USP-25 proteins, but more preferably encodes portions of the USP-25 proteins including peptides derived from the USP-25 protein. In a preferred embodiment a patient is immunized with a DNA vaccine comprising a plurality of nucleotide sequences derived from a USP-25 protein gene. Similarly, it is possible to immunize a patient with a plurality of USP-25 protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing USP-25 proteins.

In a preferred embodiment, the DNA vaccines include a gene encoding an adjuvant molecule with the DNA vaccine. Such adjuvant molecules include cytokines that increase the immunogenic response to the USP-25 protein encoded by the DNA vaccine. Additional or alternative adjuvants are known to those of ordinary skill in the art and find use in the invention.

The examples described herein serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety. Moreover, all sequences displayed, cited by reference or accession number in the references are incorporated by reference herein.

EXAMPLES

Example 1

USP-25 Amino Acid Sequence Reveals Homology to Ubiquitin Specific Proteases or Isopeptidases which Remove Ubiquitin from their Substrates

As illustrated in FIG. 5, USP-25 possesses an ubiquitin-associated domain, an ubiquitin protease domain with a conserved catalytic cysteine residue and two conserved histidine residues, a tyrosine phosphorylation domain, a ubiquitin hydrolase motif, and a response regulatory protein domain.

FIG. 5 also depicts the sequence of a catalytically dead USP-25 variant protein in which the catalytic cysteine residue is replaced by a serine residue.

Example 2

Northern blot analysis was performed with RNA isolated from a variety of human tissues, including spleen and thymus, and a variety of human cell lines (data not shown). USP-25 mRNA appears to be ubiquitously expressed. However, the level of USP-25 expression is lower in spleen tissue than many other tissues, suggesting cells of the tissue (i.e. lymphocytes) may be more sensitive to inhibitory pharmacological agents, or lower doses of inhibitory pharmacological agents may be required to affect the cells of this tissue.

Example 3

Nucleic acids encoding catalytically dead mutant ("mutant" used interchangeably with "variant" herein) USP-25 and wildtype USP-25 proteins were introduced into B cell lines stably transfected with an NFAT promoter operatively fused to a luciferase gene. Following stimulation of the NFAT promoter reporter B cell lines with anti-IgM antibody (i.e. induction of B cell activation), the activity of the reporter gene (luciferase) was determined to indicate NFAT promoter activity. The results of the assays are depicted in FIG. 6.

In the absence of exogenous mutant or wildtype USP-25 protein, anti-IgM antibody induced an increase in NFAT promoter activity in B cells.

In the presence of wildtype USP-25 protein, anti-IgM antibody induced an increase in NFAT promoter activity in B cells.

In the presence of catalytically dead mutant USP-25 protein, the response of B cells to anti-IgM antibody was decreased as compared to the responses in the presence of wildtype USP-25 protein and in the absence of wildtype and mutant USP-25 protein.

Example 4

Jurkat T cells were transiently cotransfected with expression vectors encoding flag-tagged catalytically dead mutant USP-25 or wildtype USP-25 protein, and SYK protein. Cell lysates were prepared from transfected cells, and flag-tagged USP-25 or flag-tagged mutant USP-25 protein was immunoprecipitated using anti-flag antibody. Western blots were run with the immunoprecipitates using anti-SYK antibody to determine if SYK protein precipitated with flag-tagged USP-25 and flag-tagged mutant USP-25 proteins.

SYK protein was detected in Western blots run on anti-flag immunoprecipitates from cells transfected with wildtype USP-25 and mutant USP-25 vectors (data not shown). Thus, SYK associates with USP-25 in lymphocytes, and this association does not require USP-25 catalytic activity.

---

We claim:

1. A method for screening for a bioactive agent that modulates USP-25 protein ubiquitin-specific peptidase activity, comprising:
   a) combining a USP-25 protein, a USP-25 target protein which is conjugated to ubiquitin, and a candidate bioactive agent; and
   b) determining the level of ubiquitin-conjugated target protein in the presence and absence of said candidate bioactive agent;
   wherein said USP-25 protein comprises an amino acid sequence having at least about 95% identity to SEQ ID NO:2, wherein said USP-25 protein will bind to said USP-25 target protein, and wherein a difference in the level of ubiquitin-conjugated or ubiquitin-like protein-conjugated target protein in the presence and absence of said candidate bioactive agent indicates that said candidate bioactive agent modulates USP-25 protein ubiquitin-specific peptidase activity.

2. The method according to claim 1 wherein said USP-25 target protein is selected from the group consisting of UBC9, SYK and calcineurin.

3. A method for screening for a bioactive agent that modulates USP-25 protein ubiquitin-like protein specific peptidase activity, comprising:

a) combining:

a USP-25 protein, wherein said USP-25 protein comprises an amino acid sequence having at least about 95% identity to SEQ ID NO:2, and a candidate bioactive agent, and a USP-25 target protein selected from the group consisting of UBC9, SYK and calcineurin, wherein said USP-25 protein will bind to said USP-25 target protein, and wherein the USP-25 target protein is conjugated to a ubiquitin-like protein, wherein said ubiquitin-like protein is SMT3/SUMO or NEDD8/RUDY; and b) determining the level of ubiquitin-like protein-conjugated target protein in the presence and absence of said candidate bioactive agent;

wherein a difference in the level of ubiquitin-like protein-conjugated target protein in the presence and absence of said candidate bioactive agent indicates that said candidate bioactive agent modulates USP-25 protein ubiquitin-like protein specific peptidase activity.

4. The method according to claim 1 or claim 3, wherein said USP-25 protein comprises SEQ ID NO:2.

5. The method according to claim 1 or claim 3, wherein said USP-25 protein comprises an amino acid sequence having at least about 95% identity to a fragment of SEQ ID NO:2 wherein said USP-25 protein comprises a ubiquitin-specific peptidase domain.

6. A The method of claim 1 or 3, wherein said USP-25 protein is encoded by a nucleic acid sequence with at least 95% identity to SEQ ID NO:1.

7. The method according to claim 1 or 6, wherein said USP-25 protein is encoded by SEQ ID NO:1.

8. The method according to claim 6, wherein said USP-25 protein comprises an amino acid sequence having at least about 95% identity to an amino acid sequence encoded by a fragment of SEQ ID NO:1, wherein said USP-25 protein comprises a ubiquitin-specific peptidase domain.

* * * * *